(12) United States Patent
Glass et al.

(10) Patent No.: US 11,549,000 B2
(45) Date of Patent: Jan. 10, 2023

(54) CELLULAR GLYCOSAMINOGLYCAN COMPOSITIONS AND METHODS OF MAKING AND USING

(71) Applicant: TEGA THERAPEUTICS, INC., La Jolla, CA (US)

(72) Inventors: Charles Glass, San Diego, CA (US); Bryan Thacker, San Diego, CA (US); Jeffrey Esko, San Diego, CA (US)

(73) Assignee: TEGA Therapeutics, Inc., San Diego, CA (US)

( * ) Notice: Subject to any disclaimer, the term of this patent is extended or adjusted under 35 U.S.C. 154(b) by 266 days.

(21) Appl. No.: 16/063,670

(22) PCT Filed: Dec. 16, 2016

(86) PCT No.: PCT/US2016/067373
§ 371 (c)(1),
(2) Date: Jun. 18, 2018

(87) PCT Pub. No.: WO2017/106782
PCT Pub. Date: Jun. 22, 2017

(65) Prior Publication Data
US 2020/0332088 A1    Oct. 22, 2020

Related U.S. Application Data

(60) Provisional application No. 62/269,879, filed on Dec. 18, 2015.

(51) Int. Cl.
*C08L 5/00* (2006.01)
*A61K 31/737* (2006.01)
*C08B 37/00* (2006.01)

(52) U.S. Cl.
CPC ............ *C08L 5/00* (2013.01); *A61K 31/737* (2013.01); *C08B 37/0075* (2013.01)

(58) Field of Classification Search
None
See application file for complete search history.

(56) References Cited

U.S. PATENT DOCUMENTS

| | | | |
|---|---|---|---|
| 4,421,650 A | 12/1983 | Nagasawa et al. | |
| 5,023,175 A | 6/1991 | Hosoya et al. | |
| 5,104,856 A | 4/1992 | Esko et al. | |
| 7,009,039 B2 | 3/2006 | Yayon et al. | |
| 2003/0139333 A1 | 7/2003 | Pawliuk et al. | |
| 2008/0146522 A1 | 6/2008 | Coombe et al. | |
| 2009/0163435 A1 | 6/2009 | Bader et al. | |
| 2011/0165132 A1 | 7/2011 | Cool et al. | |
| 2012/0230964 A1 | 9/2012 | Cool et al. | |
| 2012/0295890 A1 | 11/2012 | Crawford et al. | |
| 2014/0298497 A1 | 10/2014 | Arock et al. | |
| 2017/0204362 A1 | 7/2017 | Holman et al. | |
| 2020/0038430 A1 | 2/2020 | Glass et al. | |

FOREIGN PATENT DOCUMENTS

| | | |
|---|---|---|
| EP | 0144019 A2 | 6/1985 |
| WO | WO-9014418 A1 | 11/1990 |
| WO | WO-9106303 A1 | 5/1991 |
| WO | WO-2004050673 A2 | 6/2004 |
| WO | WO-2007083274 A1 | 7/2007 |
| WO | WO-2008116889 A1 | 10/2008 |
| WO | WO-2011153458 A2 | 12/2011 |
| WO | WO-2014185858 A1 | 11/2014 |
| WO | WO-2016091268 A2 | 6/2016 |
| WO | WO-2016172766 A1 | 11/2016 |
| WO | WO-2017106782 A1 | 6/2017 |
| WO | WO-2018112434 A1 | 6/2018 |
| WO | WO-2021041711 A1 | 3/2021 |

OTHER PUBLICATIONS

Ledin, J Biol Chem Oct. 8, 2004;279(41):42732-41. (Year: 2004).*
Pan, Blood, Sep. 15, 2005, vol. 106, No. 6, pp. 1956-1964. (Year: 2005).*
Zcharia, The FASEB Journal, vol. 18, Feb. 2004, pp. 252-263. (Year: 2004).*
Hernaiz, Carbohydrate Polymers 48 (2002) 153-160. (Year: 2002).*
Galvis, Nat Chem Biol. Dec. 2007; 3(12):773-8. (Year: 2007).*
ESKO. Special Considerations for Proteoglycans and Glycosaminoglycans and Their Purification. Curr Protoc Mol Biol Chapter 17:Unit17.2.1-17.2.9 (2000).
PCT/US2020/048243 Invitation to Pay Additional Fees dated Dec. 2, 2020.
Saksela et al. Endothelial cell-derived heparan sulfate binds basic fibroblast growth factor and protects it from proteolytic degradation. J Cell Biol 107(2):743-751 (1988).
Vieira et al. Acharan sulfate, the new glycosaminoglycan from Achatina fulica Bowdich 1822. Structural heterogeneity, metabolic labeling and localization in the body, mucus and the organic shell matrix. Eur J Biochem. 271(4):845-54 (2004).
PCT/US2016/067373 International Preliminary Report on Patentability dated Jun. 28, 2018.
PCT/US2016/067373 International Search Report and Written Opinion dated Mar. 9, 2017.
PCT/US2017/066860 International Search Report and Written Opinion dated Apr. 25, 2018.
Gasimili et al. Bioengineering murine mastocytoma cells to produce anticoagulant heparin. Glycobiology 24(3):272-280 (2013).
Glass. Recombinant Heparin-New Opportunities. Frontiers in Medicine 5(341):1-14 (2018).
Jozaki et al.: Proliferative potential of murine peritoneal mast cells after degranulation induced by compound 48/80, substance P, tetradecanoylphorbol acetate, or calcium ionophore A23187. J Immunol 145(12):4252-4256 (1990).
Montgomery et al. Stable heparin-producing cell lines derived from the Furth murine mastocytoma. PNAS USA 89(23):11327-11331 (1992).
PCT/US2020/048243 International Search Report and Written Opinion dated Feb. 5, 2021.

(Continued)

*Primary Examiner* — Layla D Berry
(74) *Attorney, Agent, or Firm* — Wilson Sonsini Goodrich & Rosati

(57) ABSTRACT

Disclosed herein are substantially pure glycosaminoglycan compositions derived from genetically modified cells.

10 Claims, 9 Drawing Sheets

(56) References Cited

OTHER PUBLICATIONS

Shimada et al. Novel heparan sulfate assay by using automated high-throughput mass spectrometry: Application to monitoring and screening for mucopolysaccharidoses. Molecular Genetics and Metabolism 113(Iss. 1-2):92-99 (2014).
U.S. Appl. No. 16/470,164 Office Action dated Jun. 9, 2021.
Holmborn et al.: Heparan sulfate synthesized by mouse embryonic stem cells deficient in NDST1 and NDST2 is 6-O-sulfated but contains no N-sulfate groups. J Biol Chem. 279(41):42355-42358 doi:10.1074/jbc.C400373200 (2004).
Tian et al.: Loss of CHSY1, a secreted FRINGE enzyme, causes syndromic brachydactyly in humans via increased NOTCH signaling. Am J Hum Genet. 87(6):768-778 doi:10.1016/j.ajhg.2010.11.005 (2010).
Oldberg et al.: Cell-surface heparan sulfate. Isolation and characterization of a proteoglycan from rat liver membranes. J Biol Chem. 254(17):8505-8510 (1979).
Sugahara et al.: Heparin and heparan sulfate biosynthesis. IUBMB Life 54(4):163-175 doi:10.1080/15216540214928 (2002).
U.S. Appl. No. 16/470,164 Final Office Action dated Jan. 18, 2022.
Merry et al.: The molecular phenotype of heparan sulfate in the Hs2st-/- mutant mouse. J Biol Chem. 276(38):35429-35434 doi:10.1074/jbc.M100379200 (2001).
U.S. Appl. No. 16/470,164 Non-Final Office Action dated Oct. 28, 2022.

\* cited by examiner

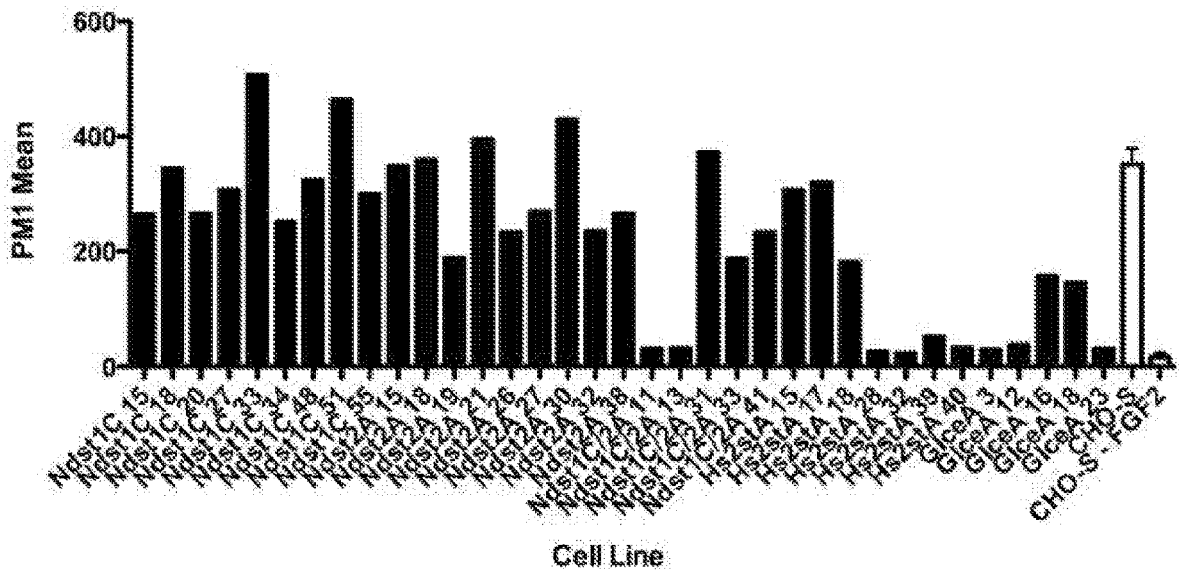

FIG. 9

```
Query    1  MLQLWKVVRPARQLELHRLILLLIGFSLVSMGFLAYYVSTSPKAKEPLPLPLGDCSSSGA   60
            MLQLWKVVRPARQLELHRLILLLIGFSLVSMGFLAYYVSTSPKAKEPLPLPLGDCSSSGA
Sbjct    1  MLQLWKVVRPARQLELHRLILLLIGFSLVSMGFLAYYVSTSPKAKEPLPLPLGDCSSSGA   60

Query   61  AGPGPARPPVPPRPPRPPETTRTEPVVLVFVESAYSQLGQEIVAILESSRFRYSTELAPG  120
            AGPGPARPPVPPRPPRPPETTRTEPVVLV        LGQEIVAILESSRFRYSTELAPG
Sbjct   61  AGPGPARPPVPPRPPRPPETTRTEPVVLV--------LGQEIVAILESSRFRYSTELAPG  112

Query  121  RGDMPTLTDHTHGRYVLVIYENLLKYVNLDSWSRELLDRYCVEYGVGIIGFFRAHEHSLL  180
            RGDMPTLTDHTHGRYVLVIYENLLKYVNLDSWSRELLDRYCVEYGVGIIGFFRAHEHSLL
Sbjct  113  RGDMPTLTDHTHGRYVLVIYENLLKYVNLDSWSRELLDRYCVEYGVGIIGFFRAHEHSLL  172

Query  181  SAQLKGFPLFLHSNLGLRDYQVNPSAPLLHLTRPSRLEPGPLPGDDWTIFQSNHSTYEPV  240
            SAQLKGFPLFLHSNLGLRDYQVNPSAPLLHLTRPSRLEPGPLPGDDWTIFQSNHSTYEPV
Sbjct  173  SAQLKGFPLFLHSNLGLRDYQVNPSAPLLHLTRPSRLEPGPLPGDDWTIFQSNHSTYEPV  232

Query  241  LLASHRPAELPVPGPVLRRARLPTVVQDLGLHDGIQRVLFGHGLSFWLHKLVFVDAVAYL  300
            LLASHRPAELPVPGPVLRRARLPTVVQDLGLHDGIQRVLFGHGLSFWLHKLVFVDAVAYL
Sbjct  233  LLASHRPAELPVPGPVLRRARLPTVVQDLGLHDGIQRVLFGHGLSFWLHKLVFVDAVAYL  292

Query  301  TGKRLCLDLDRYILVDIDDIFVGKEGTRMKVADVE  335
            TGKRLCLDLDRYILVDIDDIFVGKEGTRMKVADVE
Sbjct  293  TGKRLCLDLDRYILVDIDDIFVGKEGTRMKVADVE  327
```

FIG. 10A

```
Hs2stA5

Query  1
MGLLRIMMPPKLQLLAVVAFAVAMLFLENQIQKLEESRAKLERAIARHEVREIEQRHTMD   60

MGLLRIMMPPKLQLLAVVAFAVAMLFLENQIQKLEESRAKLERAIARHEVREIEQRHTMD
Sbjct  1
MGLLRIMMPPKLQLLAVVAFAVAMLFLENQIQKLEESRAKLERAIARHEVREIEQRHTMD   60

Query  61
GPRQDAAVDEEEDIVIIYNRVPKTASTSFTNIAYDLCAKNRYHVLHINTTKNNPVMSLQD
120

GPRQDAAVDEEEDIVIIYNRVPKTASTSFTNIAYDLCAKNRYHVLHINTTKNNPVMSLQD
Sbjct  61
GPRQDAAVDEEEDIVIIYNRVPKTASTSFTNIAYDLCAKNRYHVLHINTTKNNPVMSLQD
120

Query  121
QVRFVKNITTWNEMKPGFYHGHISYLDFAKFGVKKKPIYINVIRDPIERLVSYYYFLRFG
180

QVRFVKNITTWNEMKPGFYHGHISYLDFAKFGVKKKPIYINVIRDPIERLVSYYYFLRFG
Sbjct  121
QVRFVKNITTWNEMKPGFYHGHISYLDFAKFGVKKKPIYINVIRDPIERLVSYYYFLRFG
180

Query  181    DDYRPGLRRRKQGDKKTFD...
              DDYRPGLRRRK   +K
Sbjct  181    DDYRPGLRRRKTRRQKDL*  198
```

FIG. 10B

CELLULAR GLYCOSAMINOGLYCAN COMPOSITIONS AND METHODS OF MAKING AND USING

CROSS-REFERENCE

This application is a U.S. National Phase of International Application No. PCT/US2016/067373, filed Dec. 16, 2016, which claims the benefit of U.S. Application Ser. No. 62/269,879, filed Dec. 18, 2015, each of which is herein incorporated by reference in its entirety.

BACKGROUND

Glycosaminoglycans such as heparan sulfate, chondroitin sulfate, keratan sulfate, and hyaluronic acid play important roles in cellular and tissue specific physiology, pathophysiology and development because of their specific binding to a wide variety of proteins. These proteins include enzymes, extracellular signaling molecules, chemokines, lipid- or membrane-binding proteins, adhesion proteins and pathogenic proteins giving glycosaminoglycans important biological roles in inflammatory processes, cell growth and differentiation, hematology, cell-cell and cell-matrix interactions, lipid transport and clearance/metabolism, and host defense and viral infection.

SUMMARY OF THE INVENTION

Disclosed herein are compositions comprising a heparan sulfate derived from a genetically modified cell line, wherein the compositions are substantially free from chondroitin sulfate, dermatan sulfate, keratan sulfate, and/or hyaluronic acid. In some embodiments, the composition is derived from a cell line genetically modified to be deficient for one or more genes recited in Table 1 or Table 2. In some embodiments, the composition is derived from a cell line genetically modified to be deficient for one or more of chondroitin sulfate synthase 1 (ChSy), Chondroitin Sulfate N-Acetylgalactosaminyltransferase 2 (CSGaNAcT2), Chondroitin Polymerizing Factor (ChPF), heparan sulfate 2-O-sulphotransferase (HS2ST), glucuronic acid epimerase (GLCE), heparan sulfate N-deacetylase/sulfotransferase-1 (HSNDST1), heparan sulfate N-deacetylase/sulfotransferase-2 (HSNDST2), Sulfatase 1 (Sulf1), Sulfatase 2 (Sulf2), Beta-glucuronidase (GUSB), Galactosamine-6 sulfatase (GALNS), Alpha-L-iduronidase (IDUA), Sulfamidase (SGSH), N-acetyltransferase (AANAT, ARD1A, GNPNAT1, HGSNAT, MAK10, NAT1, NAT2, NAT5, NAT6, NAT8, NAT8L, NAT9, NAT10, NAT11, NAT12, NAT13, NAT14, NAT14), Uronate-2-sulfatase (IDS), Alpha-N-acetylglucosaminidase (NAGLU), PAPS synthase (PAPSS1, PAPSS2), Xylosyltransferase 1 (XYLT1), Xylosyltransferase 2 (XYLT2), Galactosyltransferase 1 (B4GALT1), Galactosyltransferase 2 (B4GALT2), Glucuronyltransferase 1 (UDPGT), Exostosin-Like Glycosyltransferase 3 (EXTL3), Exostosin Glycosyltransferase 1 (EXT1), Exostosin Glycosyltransferase 2 (EXT2), Heparanase (HPSE), Glypican 1 (GPC1), Glypican 2 (GPC2), Glypican 3 (GPC3), Glypican 4 (GPC4), Glypican 5 (GPC5), Glypican 6 (GPC6), Syndecan 1 (SDC1), Syndecan 2 (SDC2), Syndecan 3 (SDC3), Syndecan 4 (SDC4), Betaglycan (BGCAN/TGFBR3), CD44V3 (CD44V3), Neuropillin 1 (NRP1), Serglycin (SRGN), Perlecan (PLC), Agrin (AGRN), or Collagen 18 (COL18A1). In some embodiments, the composition is derived from a cell line genetically modified to be deficient for chondroitin sulfate synthase 1 (ChSy). In some embodiments, the composition is derived from cells that do not produce chondroitin sulfate. In some embodiments, the composition is derived from a cell line genetically modified to be transgenic for one or more genes recited in Table 1 or Table 2. In some embodiments, the composition is derived from a cell line genetically modified to be transgenic for one or more of heparan sulfate N-deacetylase/sulfotransferase-3 (HSNDST3), heparan sulfate N-deacetylase/sulfotransferase-4 (HSNDST4), heparan sulfate 6-O-sulfotransferase 1 (HS6ST1), heparan sulfate 6-O-sulfotransferase 2 (HS6ST2), heparan sulfate 6-O-sulfotransferase 3 (HS6ST3), heparan sulfate 6-O-sulfotransferase (HS6ST4), heparan sulfate (glucosamine) 3-O-sulfotransferase 1 a (HS3ST1A), heparan sulfate (glucosamine) 3-O-sulfotransferase 1 b (HS3ST1B), heparan sulfate (glucosamine) 3-O-sulfotransferase 12 (HS3ST2), heparan sulfate (glucosamine) 3-O-sulfotransferase 3a or 3b (HS3ST3a or 3b), heparan sulfate (glucosamine) 3-O-sulfotransferase 3 (HS3ST4), heparan sulfate (glucosamine) 3-O-sulfotransferase 5 (HS3ST5), heparan sulfate (glucosamine) 3-O-sulfotransferase 6 (HS3ST6), Beta-glucuronidase (GUSB), Galactosamine-6 sulfatase (GALNS), Alpha-L-iduronidase (IDUA), Sulfamidase (SGSH), N-acetyltransferase (HGSNAT), Uronate-2-sulfatase (IDS), Alpha-N-acetylglucosaminidase (NAGLU), PAPS synthase (PAPSS1, PAPSS2), Xylosyltransferase 1 (XYLT1), Xylosyltransferase 2 (XYLT2), Galactosyltransferase 1 (B4GALT1), Galactosyltransferase 2 (B4GALT2), Glucuronyltransferase 1 (UDPGT), Exostosin-Like Glycosyltransferase 3 (EXTL3), Exostosin Glycosyltransferase 1 (EXT1), Exostosin Glycosyltransferase 2 (EXT2), Heparanase (HPSE), Glypican 1 (GPC1), Glypican 2 (GPC2), Glypican 3 (GPC3), Glypican 4 (GPC4), Glypican 5 (GPC5), Glypican 6 (GPC6), Syndecan 1 (SDC1), Syndecan 2 (SDC2), Syndecan 3 (SDC3), Syndecan 4 (SDC4), Betaglycan (BGCAN/TGFBR3), CD44V3 (CD44V3), Neuropillin 1 (NRP1), Serglycin (SRGN), Perlecan (PLC), Agrin (AGRN), or Collagen 18 (COL18A1). In some embodiments, the composition is derived from a cell line genetically modified to be deficient in Chsy1. In some embodiments, the composition is derived from a cell line genetically modified to be deficient in Chsy1 and Hs2st. In some embodiments, the composition is derived from a cell line genetically modified to be deficient in Chsy1 and Glce. In some embodiments, the composition is derived from a cell line genetically modified to be deficient in Chsy1 and Hsndst1. In some embodiments, the composition is derived from a cell line genetically modified to be deficient in Chsy1 and Hsndst2. In some embodiments, the composition is derived from a cell line genetically modified to be deficient in Chsy1, Hsndst1, and Hsndst2. In some embodiments, the composition is derived from a cell line genetically modified to be deficient in Chsy1 and Hsndst3. In some embodiments, the composition is derived from a cell line genetically modified to be deficient in Chsy1 and Hsndst4. In some embodiments, the composition is derived from a cell line genetically modified to be deficient in Chsy1 and Sulf1. In some embodiments, the composition is derived from a cell line genetically modified to be deficient in Chsy1 and Sulf2. In some embodiments, the composition is derived from a cell line genetically modified to be deficient in Chsy1, Sulf1 and Sulf2. In some embodiments, the composition is derived from a cell line genetically modified to be deficient in Chsy1, Hsndst1, and Hsndst2 and modified to be transgenic for Hsndst3. In some embodiments, the composition is derived from a cell line genetically modified to be deficient in Chsy1, Hsndst1, and Hsndst2 and modified to be transgenic for Hsndst4. In some embodiments, the composition is derived from a cell line genetically modified to be deficient in Chsy1 and modified to be transgenic for Hs6st1. In some embodiments, the composition is derived from a cell line genetically modified to be deficient in Chsy1 and modified to be transgenic for Hs6st2. In some embodiments, the composition is derived from a cell line genetically modified to be deficient in Chsy1 and modified to be transgenic for Hs6st3. In some embodiments, the composition is derived from a cell line genetically modified to be deficient in Chsy1, Hsndst1, and Hsndst2 and modified to be transgenic for Hs6st1 and Hs6st2. In some embodiments, the composition is derived from a cell line genetically modified to be deficient in Chsy1 and modified to be transgenic for Hs3st1. In some embodiments, the composition is derived from a cell line genetically modified to be deficient in Chsy1 and modified to be transgenic for Hs3st2. In some embodiments, the composition is derived from a cell line genetically modified to be deficient in Chsy1 and modified to be transgenic for Hs3st3a. In some embodiments, the composition is derived from a cell line genetically modified to be deficient in Chsy1 and modified to be transgenic for Hs3st3b. In some embodiments, the composition is derived from a cell line genetically modified to be deficient in Chsy1 and modified to be transgenic for Hs3st4. In some embodiments, the composition is derived from a cell line genetically modified to be deficient in Chsy1 and modified to be transgenic for Hs3st5. In some embodiments, the composition is derived from a cell line genetically modified to be deficient in Chsy1 and modified to be transgenic for Hs3st6. In some embodiments, the composition is derived from a cell line genetically modified to be deficient in Chsy1 and modified to be transgenic for Hs6st1, Hs6st2, and Hs3st1. In some embodiments, the composition is derived from a cell line genetically modified to be deficient in Chsy1 and modified to be transgenic for Hs6st1, Hs6st2, and Hs3st2. In some embodiments, the composition is derived from a cell line genetically modified to be deficient in Chsy1 and modified to be transgenic for Hs6st1, Hs6st2, and Hs3st3a or Hs3st3b. In some embodiments, the composition is derived from a cell line genetically modified to be deficient in Chsy1 and modified to be transgenic for Hs6st1, Hs6st2, and Hs3st4. In some embodiments, the composition is derived from a cell line genetically modified to be deficient in Chsy1 and modified to be transgenic for Hs6st1, Hs6st2, and Hs3st5. In some embodiments, the composition is derived from a cell line genetically modified to be deficient in Chsy1 and modified to be transgenic for Hs6st1, Hs6st2, and Hs3st6. In some embodiments, the composition is derived from a cell line genetically modified to be deficient in Chsy1, Hsndst1, and Hsndst2 and modified to be transgenic for Hsndst3 and Hs6st1. In some embodiments, the composition is derived from a cell line genetically modified to be deficient in Chsy1, Hsndst1, and Hsndst2 and modified to be transgenic for Hsndst3 and Hs6st2. In some embodiments, the composition is derived from a cell line genetically modified to be deficient in Chsy1, Hsndst1, and Hsndst2 and modified to be transgenic for Hsndst3 and Hs6st3. In some embodiments, the composition is derived from a cell line genetically modified to be deficient in Chsy1, Hsndst1, and Hsndst2 and modified to be transgenic for Hsndst4 and Hs6st1. In some embodiments, the composition is derived from a cell line genetically modified to be deficient in Chsy1, Hsndst1, and Hsndst2 and modified to be transgenic for Hsndst4 and Hs6st2. In some embodiments, the composition is derived from a cell line genetically modified to be deficient in Chsy1, Hsndst1, and Hsndst2 and modified to be transgenic for Hsndst4 and Hs6st3. In some embodiments, the composition is derived from a cell line genetically modified to be deficient in Chsy1, Hsndst1, and Hsndst2 and modified to be transgenic for Hsndst3 and Hs3st1. In some embodiments, the composition is derived from a cell line genetically modified to be deficient in Chsy1, Hsndst1, and Hsndst2 and modified to be transgenic for Hsndst3 and Hs3st2. In some embodiments, the composition is derived from a cell line genetically modified to be deficient in Chsy1, Hsndst1, and Hsndst2 and modified to be transgenic for Hsndst3 and Hs3st3a. In some embodiments, the composition is derived from a cell line genetically modified to be deficient in Chsy1, Hsndst1, and Hsndst2 and modified to be transgenic for Hsndst3 and Hs3st3b. In some embodiments, the composition is derived from a cell line genetically modified to be deficient in Chsy1, Hsndst1, and Hsndst2 and modified to be transgenic for Hsndst3 and Hs3st4. In some embodiments, the composition is derived from a cell line genetically modified to be deficient in Chsy1, Hsndst1, and Hsndst2 and modified to be transgenic for Hsndst3 and Hs3st5. In some embodiments, the composition is derived from a cell line genetically modified to be deficient in Chsy1, Hsndst1, and Hsndst2 and modified to be transgenic for Hsndst3 and Hs3st6. In some embodiments, the composition is derived from a cell line genetically modified to be deficient in Chsy1, Hsndst1, and Hsndst2 and modified to be transgenic for Hsndst4 and Hs3st1. In some embodiments, the composition is derived from a cell line genetically modified to be deficient in Chsy1, Hsndst1, and Hsndst2 and modified to be transgenic for Hsndst4 and Hs3st2. In some embodiments, the composition is derived from a cell line genetically modified to be deficient in Chsy1, Hsndst1, and Hsndst2 and modified to be transgenic for Hsndst4 and Hs3st3a. In some embodiments, the composition is derived from a cell line genetically modified to be deficient in Chsy1, Hsndst1, and Hsndst2 and modified to be transgenic for Hsndst4 and Hs3st3b. In some embodiments, the composition is derived from a cell line genetically modified to be deficient in Chsy1, Hsndst1, and Hsndst2 and modified to be transgenic for Hsndst4 and Hs3st4. In some embodiments, the composition is derived from a cell line genetically modified to be deficient in Chsy1, Hsndst1, and Hsndst2 and modified to be transgenic for Hsndst4 and Hs3st5. In some embodiments, the composition is derived from a cell line genetically modified to be deficient in Chsy1, Hsndst1, and Hsndst2 and modified to be transgenic for Hsndst4 and Hs3st6. In some embodiments, the composition is derived from a cell line genetically modified to be deficient in Chsy1, Hsndst1, and Hsndst2 and modified to be transgenic for Hsndst3, Hs6st1/2, and Hs3st1. In some embodiments, the composition is derived from a cell line genetically modified to be deficient in Chsy1, Hsndst1, and Hsndst2 and modified to be transgenic for Hsndst3, Hs6st1/2, and Hs3st2. In some embodiments, the composition is derived from a cell line genetically modified to be deficient in Chsy1, Hsndst1, and Hsndst2 and modified to be transgenic for Hsndst3, Hs6st1/2, and Hs3st3a. In some embodiments, the composition is derived from a cell line genetically modified to be deficient in Chsy1, Hsndst1, and Hsndst2 and modified to be transgenic for Hsndst3, Hs6st1/2, and Hs3st3b. In some embodiments, the composition is derived from a cell line genetically modified to be deficient in Chsy1, Hsndst1, and Hsndst2 and modified to be transgenic for Hsndst3, Hs6st1/2, and Hs3st4. In some embodiments, the composition is derived from a cell line genetically modified to be deficient in Chsy1, Hsndst1, and Hsndst2 and modified to be transgenic for Hsndst3, Hs6st1/2, and Hs3st5. In some embodiments, the composition is derived from a cell line genetically modified to be deficient in Chsy1, Hsndst1, and Hsndst2 and modified to be transgenic for Hsndst3, Hs6st1/2, and Hs3st6. In some embodiments, the composition is derived from a cell line genetically modified to be deficient in Chsy1, Hsndst1, and Hsndst2 and modified to be transgenic for Hsndst4, Hs6st1/2, and Hs3st1. In some embodiments, the composition is derived from a cell line genetically modified to be deficient in Chsy1, Hsndst1, and Hsndst2 and modified to be transgenic for Hsndst4, Hs6st1/2, and Hs3st2. In some embodiments, the composition is derived from a cell line genetically modified to be deficient in Chsy1, Hsndst1, and Hsndst2 and modified to be transgenic for Hsndst4, Hs6st1/2, and Hs3st3a. In some embodiments, the composition is derived from a cell line genetically modified to be deficient in Chsy1, Hsndst1, and Hsndst2 and modified to be transgenic for Hsndst4, Hs6st1/2, and Hs3st3b. In some embodiments, the composition is derived from a cell line genetically modified to be deficient in Chsy1, Hsndst1, and Hsndst2 and modified to be transgenic for Hsndst4, Hs6st1/2, and Hs3st4. In some embodiments, the composition is derived from a cell line genetically modified to be deficient in Chsy1, Hsndst1, and Hsndst2 and modified to be transgenic for Hsndst4, Hs6st1/2, and Hs3st5. In some embodiments, the composition is derived from a cell line genetically modified to be deficient in Chsy1, Hsndst1, and Hsndst2 and modified to be transgenic for Hsndst4, Hs6st1/2, and Hs3st6. In some embodiments, the composition comprises a heparan sulfate with a defined pattern of sulfation. In some embodiments, the heparan sulfate is at least 95% free of protein and nucleic acid contamination. In some embodiments, the heparan sulfate is at least 95% free of chondroitin sulfate. In some embodiments, the heparan sulfate is at least 99% free of protein and nucleic acid. In some embodiments, the heparan sulfate is at least 99% free of chondroitin sulfate.

Also provided herein are compositions comprising a chondroitin sulfate derived from a genetically modified cell line, wherein the compositions are substantially free from heparan sulfate, dermatan sulfate, keratan sulfate, and/or hyaluronic acid. In some embodiments, the composition is derived from a cell line genetically modified to be deficient for one or more genes recited in Table 4 or Table 5. In some embodiments, the composition is derived from a cell line genetically modified to be deficient for one or more of GaNAc transferase 1 (CsGalNAcT1), GalNAc transferase 2 (CSGalNAcT2), Chondroitin sulfate synthase 1 (Chsy1), Chondroitin sulfate synthase 3 (Chsy3), Chondroitin sulfate polymerizing factor (Chpf), Chondroitin sulfate polymerizing factor (Chpf2), Chondroitn 4-O-sulfotransferase 1 (Chst11), Chondroitin 4-O-sulfotransferase 2 (Chst12), Chondroitin 4-O-sulfotransferase 3 (Chst13), Chondroitin 4-sulfate 6-O-sulfotransferase (Chst15), Chondroitin 6 sulfotransferase-1 (Chst3), Chondroitin 6-O-sulfotransferase 2 (Chst7), Dermatan sulfate glucuronyl C5 epimerase 1 (Dse), Dermatan sulfate glucuronyl C5 epimerase-like (Dsel), Dermatan sulfate 4-O-sulfotransferase (Chst14), Aggrecan (CSPG1) (Agc1), Versican/PG-M (CSPG2) (Vcan), Neurocan (CSPG3) (Ncan), Brevican (BCAN) (Bcan), Epiphycan (Dspg3) (Epyc), Procollagen, type IX, alpha 2 (Col9a2), DSD-1-proteoglycan, Phosphacan (Ptprz1), Thrombomodulin (Thbd), Endocan (Esm1), Leprecan (Prolyl 3-hydroxylase 1) (Lepre1), Decorin (Dcn), Biglycan (Bgn), Testican 1 (Spock1; osteonectin1) (Spock1), Testican 2 (Spock2, osteonectin2 (Spock2), Testican 2 (Spock3; osteonectn3) (Spock3), Proteoglycan-4 (Lubricin) (Prg4), NG2 (CSPG4) (Cspg4), Invariant chain (Cd74), and CD44 (Cd44). In some embodiments, the composition is derived from cells that do not produce heparan sulfate, keratan sulfate, dermatan sulfate, and/or hyaluronic acid. In some embodiments, the composition is derived from a cell line genetically modified to be transgenic for one or more genes recited in Table 4 or Table 5. In some embodiments, the composition is derived from a cell line genetically modified to be transgenic for one or more of GaNAc transferase 1 (CsGalNAcT1), GaNAc transferase 2 (CSGaNAcT2), Chondroitin sulfate synthase 1 (GcAT and GaNAcT activities) (Chsy1), Chondroitin sulfate synthase 3 (Chsy3), Chondroitin sulfate polymerizing factor (Chpf), Chondroitin sulfate polymerizing factor (Chpf2), Chondroitn 4-O-sulfotransferase 1 (Chst11), Chondroitin 4-O-sulfotransferase 2 (Chst12), Chondroitin 4-O-sulfotransferase 3 (Chst13), Chondroitin 4-sulfate 6-O-sulfotransferase (Chst15), Chondroitin 6 sulfotransferase-1 (Chst3), Chondroitin 6-O-sulfotransferase 2 (Chst7), Dermatan sulfate glucuronyl C5 epimerase 1 (Dse), Dermatan sulfate glucuronyl C5 epimerase-like (Dsel), Dermatan sulfate 4-O-sulfotransferase (Chst14), Aggrecan (CSPG1) (Agc1), Versican/PG-M (CSPG2) (Vcan), Neurocan (CSPG3) (Ncan), Brevican (BCAN) (Bcan), Epiphycan (Dspg3) (Epyc), Procollagen, type IX, alpha 2 (Col9a2), DSD-1-proteoglycan, Phosphacan (Ptprz1), Thrombomodulin (Thbd), Endocan (Esm1), Leprecan (Prolyl 3-hydroxylase 1) (Lepre1), Decorin (Dcn), Biglycan (Bgn), Testican 1 (Spock1; osteonectin1) (Spock1), Testican 2 (Spock2, osteonectin2 (Spock2), Testican 2 (Spock3; osteonectn3) (Spock3), Proteoglycan-4 (Lubricin) (Prg4), NG2 (CSPG4) (Cspg4), Invariant chain (Cd74), and CD44 (Cd44). In some embodiments, the composition comprises a chondroitin sulfate with a defined pattern of sulfation. In some embodiments, the chondroitin sulfate is at least 95% free of protein and nucleic acid contamination. In some embodiments, the chondroitin sulfate is at least 95% free of heparan sulfate, dermatan sulfate, keratan sulfate, and/or hyaluronic acid. In some embodiments, the chondroitin sulfate is at least 99% free of protein and nucleic acid contamination. In some embodiments, the chondroitin sulfate is at least 99% free of heparan sulfate, dermatan sulfate, keratan sulfate, and/or hyaluronic acid.

Further provided herein are compositions comprising a dermatan sulfate derived from a genetically modified cell line, wherein the compositions are substantially free from heparan sulfate, chondroitin sulfate, keratan sulfate, and/or hyaluronic acid. In some embodiments, the composition is derived from a cell line genetically modified to be deficient for one or more genes recited in Table 4 or Table 5. In some embodiments, the composition is derived from a cell line genetically modified to be deficient for one or more of GaNAc transferase 1 (CsGalNAcT1), GalNAc transferase 2 (CSGalNAcT2), Chondroitin sulfate synthase 1 (GcAT and GalNAcT activities) (Chsy1), Chondroitin sulfate synthase 3 (Chsy3), Chondroitin sulfate polymerizing factor (Chpf), Chondroitin sulfate polymerizing factor (Chpf2), Chondroitn 4-O-sulfotransferase 1 (Chst11), Chondroitin 4-O-sulfotransferase 2 (Chst12), Chondroitin 4-O-sulfotransferase 3 (Chst13), Chondroitin 4-sulfate 6-O-sulfotransferase (Chst15), Chondroitin 6 sulfotransferase-1 (Chst3), Chondroitin 6-O-sulfotransferase 2 (Chst7), Dermatan sulfate glucuronyl C5 epimerase 1 (Dse), Dermatan sulfate glucuronyl C5 epimerase-like (Dsel), Dermatan sulfate 4-O-sulfotransferase (Chst14), Aggrecan (CSPG1) (Agc1), Versican/PG-M (CSPG2) (Vcan), Neurocan (CSPG3) (Ncan), Brevican (BCAN) (Bcan), Epiphycan (Dspg3) (Epyc), Procollagen, type IX, alpha 2 (Col9a2), DSD-1-proteoglycan, Phosphacan (Ptprz1), Thrombomodulin (Thbd), Endocan (Esm1), Leprecan (Prolyl 3-hydroxylase 1) (Lepre1), Decorin (Den), Biglycan (Bgn), Testican 1 (Spock1; osteonectin1) (Spock1), Testican 2 (Spock2, osteonectin2 (Spock2), Testican 2 (Spock3; osteonectn3) (Spock3), Proteoglycan-4 (Lubricin) (Prg4), NG2 (CSPG4) (Cspg4), Invariant chain (Cd74), and CD44 (Cd44). In some embodiments, the composition is derived from cells that do not produce heparan sulfate, keratan sulfate, chondroitin sulfate, and/or hyaluronic acid. In some embodiments, the composition is derived from a cell line genetically modified to be transgenic for one or more genes recited in Table 4 or Table 5. In some embodiments, the composition is derived from a cell line genetically modified to be transgenic for one or more of GaNAc transferase 1 (CsGaNAT1), GalNAc transferase 2 (CSGalNAcT2), Chondroitin sulfate synthase 1 (GcAT and GaNAcT activities) (Chsy1), Chondroitin sulfate synthase 3 (Chsy3), Chondroitin sulfate polymerizing factor (Chpf), Chondroitin sulfate polymerizing factor (Chpf2), Chondroitn 4-O-sulfotransferase 1 (Chst11), Chondroitin 4-O-sulfotransferase 2 (Chst12), Chondroitin 4-O-sulfotransferase 3 (Chst13), Chondroitin 4-sulfate 6-O-sulfotransferase (Chst15), Chondroitin 6 sulfotransferase-1 (Chst3), Chondroitin 6-O-sulfotransferase 2 (Chst7), Dermatan sulfate glucuronyl C5 epimerase 1 (Dse), Dermatan sulfate glucuronyl C5 epimerase-like (Dsel), Dermatan sulfate 4-O-sulfotransferase (Chst14), Aggrecan (CSPG1) (Agc1), Versican/PG-M (CSPG2) (Vcan), Neurocan (CSPG3) (Ncan), Brevican (BCAN) (Bcan), Epiphycan (Dspg3) (Epyc), Procollagen, type IX, alpha 2 (Col9a2), DSD-1-proteoglycan, Phosphacan (Ptprz1), Thrombomodulin (Thbd), Endocan (Esm1), Leprecan (Prolyl 3-hydroxylase 1) (Lepre1), Decorin (Den), Biglycan (Bgn), Testican 1 (Spock1; osteonectin1) (Spock1), Testican 2 (Spock2, osteonectin2 (Spock2), Testican 2 (Spock3; osteonectn3) (Spock3), Proteoglycan-4 (Lubricin) (Prg4), NG2 (CSPG4) (Cspg4), Invariant chain (Cd74), and CD44 (Cd44). In some embodiments, the composition comprises a dermatan sulfate with a defined pattern of sulfation. In some embodiments, the dermatan sulfate is at least 95% free of protein and nucleic acid contamination. In some embodiments, the dermatan sulfate is at least 95% free of heparan sulfate, chondroitin sulfate, keratan sulfate, and/or hyaluronic acid. In some embodiments, the dermatan sulfate is at least 99% free of protein and nucleic acid contamination. In some embodiments, the dermatan sulfate is at least 99% free of heparan sulfate, chondroitin sulfate, keratan sulfate, and/or hyaluronic acid.

Also provided herein, are compositions comprising a keratan sulfate derived from a genetically modified cell line, wherein the compositions are substantially free from heparan sulfate, dermatan sulfate, chondroitin sulfate, and/or hyaluronic acid. In some embodiments, the composition is derived from cells that do not produce heparan sulfate, keratan sulfate, chondroitin sulfate, dermatan sulfate, and/or hyaluronic acid. In some embodiments, the composition comprises a keratan sulfate with a defined pattern of sulfation. In some embodiments, the keratan sulfate is at least 95% free of protein and nucleic acid contamination. In some embodiments, the keratan sulfate is at least 95% free of heparan sulfate, chondroitin sulfate, dermatan sulfate, and/or hyaluronic acid. In some embodiments, the keratan sulfate is at least 99% free of protein and nucleic acid contamination. In some embodiments, the keratan sulfate is at least 99% free of heparan sulfate, chondroitin sulfate, dermatan sulfate, and/or hyaluronic acid.

Further provided herein are compositions comprising a hyaluronic acid derived from a genetically modified cell line, wherein the compositions are substantially free from heparan sulfate, dermatan sulfate, chondroitin sulfate, and/or keratan sulfate. In some embodiments, the composition is derived from cells that do not produce heparan sulfate, keratan sulfate, chondroitin sulfate, dermatan sulfate, and/or keratan sulfate. In some embodiments, the hyaluronic acid is at least 95% free of protein and nucleic acid contamination. In some embodiments, the hyaluronic acid is at least 95% free of heparan sulfate, chondroitin sulfate, dermatan sulfate, and/or keratan sulfate. In some embodiments, the hyaluronic acid is at least 99% free of protein and nucleic acid contamination. In some embodiments, the hyaluronic acid is at least 99% free of heparan sulfate, chondroitin sulfate, dermatan sulfate, and/or keratan sulfate.

Also provided herein are pharmaceutical compositions comprising any one of the compositions of any one of the above embodiments and a pharmaceutically acceptable carrier or excipient.

Further provided herein are compositions comprising a cell deficient in one or more genes recited in Tables 1, 2, 4, or 5. In some embodiments, the cell is deficient in one or more of chondroitin sulfate synthase 1 (ChSy), Chondroitin Sulfate N-Acetylgalactosaminyltransferase 2 (CSGalNAcT2), Chondroitin Polymerizing Factor (ChPF), heparan sulfate 2-O-sulphotransferase (HS2ST), glucuronic acid epimerase (GLCE), heparan sulfate N-deacetylase/sulfotransferase-1 (HSNDST1), heparan sulfate N-deacetylase/sulfotransferase-2 (HSNDST2), Sulfatase 1 (Sulf1), Sulfatase (Sulf2), Beta-glucuronidase (GUSB), Galactosamine-6 sulfatase (GALNS), Alpha-L-iduronidase (IDUA), Sulfamidase (SGSH), N-acetyltransferase (AANAT, ARD1A, GNPNAT1, HGSNAT, MAK10, NAT1, NAT2, NAT5, NAT6, NAT8, NAT8L, NAT9, NAT10, NAT11, NAT12, NAT13, NAT14, NAT14), Uronate-2-sulfatase (IDS), Alpha-N-acetylglucosaminidase (NAGLU), PAPS synthase (PAPSS1, PAPSS2), Xylosyltransferase 1 (XYLT1), Xylosyltransferase 2 (XYLT2), Galactosyltransferase 1 (B4GALT1), Galactosyltransferase 2 (B4GALT2), Glucuronyltransferase 1 (UDPGT), Exostosin-Like Glycosyltransferase 3 (EXTL3), Exostosin Glycosyltransferase 1 (EXT1), Exostosin Glycosyltransferase 2 (EXT2), Heparanase (HPSE), Glypican 1 (GPC1), Glypican 2 (GPC2), Glypican 3 (GPC3), Glypican 4 (GPC4), Glypican 5 (GPC5), Glypican 6 (GPC6), Syndecan 1 (SDC1), Syndecan 2 (SDC2), Syndecan 3 (SDC3), Syndecan 4 (SDC4), Betaglycan (BGCAN/TGFBR3), CD44V3 (CD44V3), Neuropillin 1 (NRP1), Serglycin (SRGN), Perlecan (PLC), Agrin (AGRN), Collagen 18 (COL18A1), GalNAc transferase 2 (CSGalNAcT2), Chondroitin sulfate synthase 1 (Chsy1), Chondroitin sulfate synthase 3 (Chsy3), Chondroitin sulfate polymerizing factor (Chpf), Chondroitin sulfate polymerizing factor (Chpf2), Chondroitn 4-O-sulfotransferase 1 (Chst11), Chondroitin 4-O-sulfotransferase 2 (Chst12), Chondroitin 4-O-sulfotransferase 3 (Chst13), Chondroitin 4-sulfate 6-O-sulfotransferase (Chst15), Chondroitin 6 sulfotransferase-1 (Chst3), Chondroitin 6-O-sulfotransferase 2 (Chst7), Dermatan sulfate glucuronyl C5 epimerase 1 (Dse), Dermatan sulfate glucuronyl C5 epimerase-like (Dsel), Dermatan sulfate 4-O-sulfotransferase (Chst14), Aggrecan (CSPG1) (Agc1), Versican/PG-M (CSPG2) (Vcan), Neurocan (CSPG3) (Ncan), Brevican (BCAN) (Bcan), Epiphycan (Dspg3) (Epyc), Procollagen, type IX, alpha 2 (Col9a2), DSD-1-proteoglycan, Phosphacan (Ptprz1), Thrombomodulin (Thbd), Endocan (Esm1), Leprecan (Prolyl 3-hydroxylase 1) (Lepre1), Decorin (Dcn), Biglycan (Bgn), Testican 1 (Spock1; osteonectin1) (Spock1), osteonectin2 (Spock2), Testican 2 (Spock3; osteonectn3) (Spock3), Proteoglycan-4 (Lubricin) (Prg4), NG2 (CSPG4)

(Cspg4), or Invariant chain (Cd74). In some embodiments, the cell is deficient in chondroitin sulfate synthase 1 (ChSy1). In some embodiments, the cell is deficient in chondroitin sulfate. In some embodiments, the cell is deficient in heparan sulfate. In some embodiments, the cell is deficient in dermatan sulfate. In some embodiments, the cell is deficient in keratan sulfate. In some embodiments, the cell is deficient in hyaluronic acid. In some embodiments, the cell is transgenic for one or more genes recited in Tables 1, 2, 4 or 5. In some embodiments, the cell is transgenic for one or more of chondroitin sulfate synthase 1 (ChSy), Chondroitin Sulfate N-Acetylgalactosaminyltransferase 2 (CSGalNAcT2), Chondroitin Polymerizing Factor (ChPF), heparan sulfate 2-O-sulphotransferase (HS2ST), glucuronic acid epimerase (GLCE), heparan sulfate N-deacetylase/sulfotransferase-1 (HSNDST1), heparan sulfate N-deacetylase/sulfotransferase-2 (HSNDST2), Sulfatase 1 (Sulf1), Sulfatase (Sulf2), Beta-glucuronidase (GUSB), Galactosamine-6 sulfatase (GALNS), Alpha-L-iduronidase (IDUA), Sulfamidase (SGSH), N-acetyltransferase (AANAT, ARD1A, GNPNAT1, HGSNAT, MAK10, NAT1, NAT2, NAT5, NAT6, NAT8, NAT8L, NAT9, NAT10, NAT11, NAT12, NAT13, NAT14, NAT14), Uronate-2-sulfatase (IDS), Alpha-N-acetylglucosaminidase (NAGLU), PAPS synthase (PAPSS1, PAPSS2), Xylosyltransferase 1 (XYLT1), Xylosyltransferase 2 (XYLT2), Galactosyltransferase 1 (B4GALT1), Galactosyltransferase 2 (B4GALT2), Glucuronyltransferase 1 (UDPGT), Exostosin-Like Glycosyltransferase 3 (EXTL3), Exostosin Glycosyltransferase 1 (EXT1), Exostosin Glycosyltransferase 2 (EXT2), Heparanase (HPSE), Glypican 1 (GPC1), Glypican 2 (GPC2), Glypican 3 (GPC3), Glypican 4 (GPC4), Glypican 5 (GPC5), Glypican 6 (GPC6), Syndecan 1 (SDC1), Syndecan 2 (SDC2), Syndecan 3 (SDC3), Syndecan 4 (SDC4), Betaglycan (BGCAN/TGFBR3), CD44V3 (CD44V3), Neuropillin 1 (NRP1), Serglycin (SRGN), Perlecan (PLC), Agrin (AGRN), Collagen 18 (COL18A1), GalNAc transferase 2 (CSGalNAcT2), Chondroitin sulfate synthase 1 (Chsy1), Chondroitin sulfate synthase 3 (Chsy3), Chondroitin sulfate polymerizing factor (Chpf), Chondroitin sulfate polymerizing factor (Chpf2), Chondroitn 4-O-sulfotransferase 1 (Chst11), Chondroitin 4-O-sulfotransferase 2 (Chst12), Chondroitin 4-O-sulfotransferase 3 (Chst13), Chondroitin 4-sulfate 6-O-sulfotransferase (Chst15), Chondroitin 6 sulfotransferase-1 (Chst3), Chondroitin 6-O-sulfotransferase 2 (Chst7), Dermatan sulfate glucuronyl C5 epimerase 1 (Dse), Dermatan sulfate glucuronyl C5 epimerase-like (Dsel), Dermatan sulfate 4-O-sulfotransferase (Chst14), Aggrecan (CSPG1) (Agc1), Versican/PG-M (CSPG2) (Vcan), Neurocan (CSPG3) (Ncan), Brevican (BCAN) (Bcan), Epiphycan (Dspg3) (Epyc), Procollagen, type IX, alpha 2 (Col9a2), DSD-1-proteoglycan, Phosphacan (Ptprz1), Thrombomodulin (Thbd), Endocan (Esm1), Leprecan (Prolyl 3-hydroxylase 1) (Lepre1), Decorin (Den), Biglycan (Bgn), Testican 1 (Spock1; osteonectin1) (Spock1), osteonectin2 (Spock2), Testican 2 (Spock3; osteonectn3) (Spock3), Proteoglycan-4 (Lubricin) (Prg4), NG2 (CSPG4) (Cspg4), or Invariant chain (Cd74). In some embodiments, the cell is genetically modified to be deficient in Chsy1. In some embodiments, the cell is genetically modified to be deficient in Chsy1 and Hs2st. In some embodiments, the cell is genetically modified to be deficient in Chsy1 and Glce. In some embodiments, the cell is genetically modified to be deficient in Chsy1 and Hsndst1. In some embodiments, the cell is genetically modified to be deficient in Chsy1 and Hsndst2. In some embodiments, the cell is genetically modified to be deficient in Chsy1, Hsndst1, and Hsndst2. In some embodiments, the cell is genetically modified to be deficient in Chsy1 and Hsndst3. In some embodiments, the cell is genetically modified to be deficient in Chsy1 and Hsndst4. In some embodiments, the cell is genetically modified to be deficient in Chsy1 and Sulf1. In some embodiments, the cell is genetically modified to be deficient in Chsy1 and Sulf2. In some embodiments, the cell is genetically modified to be deficient in Chsy1, Sulf1 and Sulf2. In some embodiments, the cell is genetically modified to be deficient in Chsy1, Hsndst1, and Hsndst2 and modified to be transgenic for Hsndst3. In some embodiments, the cell is genetically modified to be deficient in Chsy1, Hsndst1, and Hsndst2 and modified to be transgenic for Hsndst4. In some embodiments, the cell is genetically modified to be deficient in Chsy1 and modified to be transgenic for Hs6st1. In some embodiments, the cell is genetically modified to be deficient in Chsy1 and modified to be transgenic for Hs6st2. In some embodiments, the cell is genetically modified to be deficient in Chsy1 and modified to be transgenic for Hs6st3. In some embodiments, the cell is genetically modified to be deficient in Chsy1, Hsndst1, and Hsndst2 and modified to be transgenic for Hs6st1 and Hs6st2. In some embodiments, the cell is genetically modified to be deficient in Chsy1 and modified to be transgenic for Hs3st1. In some embodiments, the cell is genetically modified to be deficient in Chsy1 and modified to be transgenic for Hs3st2. In some embodiments, the cell is genetically modified to be deficient in Chsy1 and modified to be transgenic for Hs3st3a. In some embodiments, the cell is genetically modified to be deficient in Chsy1 and modified to be transgenic for Hs3st3b. In some embodiments, the cell is genetically modified to be deficient in Chsy1 and modified to be transgenic for Hs3st4. In some embodiments, the cell is genetically modified to be deficient in Chsy1 and modified to be transgenic for Hs3st5. In some embodiments, the cell is genetically modified to be deficient in Chsy1 and modified to be transgenic for Hs3st6. In some embodiments, the cell is genetically modified to be deficient in Chsy1 and modified to be transgenic for Hs6st1, Hs6st2, and Hs3st1. In some embodiments, the cell is genetically modified to be deficient in Chsy1 and modified to be transgenic for Hs6st1, Hs6st2, and Hs3st2. In some embodiments, the cell is genetically modified to be deficient in Chsy1 and modified to be transgenic for Hs6st1, Hs6st2, and Hs3st3a or Hs3st3b. In some embodiments, the cell is genetically modified to be deficient in Chsy1 and modified to be transgenic for Hs6st1, Hs6st2, and Hs3st4. In some embodiments, the cell is genetically modified to be deficient in Chsy1 and modified to be transgenic for Hs6st1, Hs6st2, and Hs3st5. In some embodiments, the cell is genetically modified to be deficient in Chsy1 and modified to be transgenic for Hs6st1, Hs6st2, and Hs3st6. In some embodiments, the cell is genetically modified to be deficient in Chsy1, Hsndst1, and Hsndst2 and modified to be transgenic for Hsndst3 and Hs6st1. In some embodiments, the cell is genetically modified to be deficient in Chsy1, Hsndst1, and Hsndst2 and modified to be transgenic for Hsndst3 and Hs6st2. In some embodiments, the cell is genetically modified to be deficient in Chsy1, Hsndst1, and Hsndst2 and modified to be transgenic for Hsndst3 and Hs6st3. In some embodiments, the cell is genetically modified to be deficient in Chsy1, Hsndst1, and Hsndst2 and modified to be transgenic for Hsndst4 and Hs6st1. In some embodiments, the cell is genetically modified to be deficient in Chsy1, Hsndst1, and Hsndst2 and modified to be transgenic for Hsndst4 and Hs6st2. In some embodiments, the cell is genetically modified to be deficient in Chsy1, Hsndst1, and Hsndst2 and modified to be transgenic for Hsndst4 and Hs6st3. In some embodiments, the cell is genetically modified to be deficient in Chsy1, Hsndst1, and Hsndst2 and modified to be transgenic for Hsndst3 and Hs3st1. In some embodiments, the cell is genetically modified to be deficient in Chsy1, Hsndst1, and Hsndst2 and modified to be transgenic for Hsndst3 and Hs3st2. In some embodiments, the cell is genetically modified to be deficient in Chsy1, Hsndst1, and Hsndst2 and modified to be transgenic for Hsndst3 and Hs3st3a. In some embodiments, the cell is genetically modified to be deficient in Chsy1, Hsndst1, and Hsndst2 and modified to be transgenic for Hsndst3 and Hs3st3b. In some embodiments, the cell is genetically modified to be deficient in Chsy1, Hsndst1, and Hsndst2 and modified to be transgenic for Hsndst3 and Hs3st4. In some embodiments, the cell is genetically modified to be deficient in Chsy1, Hsndst1, and Hsndst2 and modified to be transgenic for Hsndst3 and Hs3st5. In some embodiments, the cell is genetically modified to be deficient in Chsy1, Hsndst1, and Hsndst2 and modified to be transgenic for Hsndst3 and Hs3st6. In some embodiments, the cell is genetically modified to be deficient in Chsy1, Hsndst1, and Hsndst2 and modified to be transgenic for Hsndst4 and Hs3st1. In some embodiments, the cell is genetically modified to be deficient in Chsy1, Hsndst1, and Hsndst2 and modified to be transgenic for Hsndst4 and Hs3st2. In some embodiments, the cell is genetically modified to be deficient in Chsy1, Hsndst1, and Hsndst2 and modified to be transgenic for Hsndst4 and Hs3st3a. In some embodiments, the cell is genetically modified to be deficient in Chsy1, Hsndst1, and Hsndst2 and modified to be transgenic for Hsndst4 and Hs3st3b. In some embodiments, the cell is genetically modified to be deficient in Chsy1, Hsndst1, and Hsndst2 and modified to be transgenic for Hsndst4 and Hs3st4. In some embodiments, the cell is genetically modified to be deficient in Chsy1, Hsndst1, and Hsndst2 and modified to be transgenic for Hsndst4 and Hs3st5. In some embodiments, the cell is genetically modified to be deficient in Chsy1, Hsndst1, and Hsndst2 and modified to be transgenic for Hsndst4 and Hs3st6. In some embodiments, the cell is genetically modified to be deficient in Chsy1, Hsndst1, and Hsndst2 and modified to be transgenic for Hsndst3, Hs6st1/2, and Hs3st1. In some embodiments, the cell is genetically modified to be deficient in Chsy1, Hsndst1, and Hsndst2 and modified to be transgenic for Hsndst3, Hs6st1/2, and Hs3st2. In some embodiments, the cell is genetically modified to be deficient in Chsy1, Hsndst1, and Hsndst2 and modified to be transgenic for Hsndst3, Hs6st1/2, and Hs3st3a. In some embodiments, the cell is genetically modified to be deficient in Chsy1, Hsndst1, and Hsndst2 and modified to be transgenic for Hsndst3, Hs6st1/2, and Hs3st3b. In some embodiments, the cell is genetically modified to be deficient in Chsy1, Hsndst1, and Hsndst2 and modified to be transgenic for Hsndst3, Hs6st1/2, and Hs3st4. In some embodiments, the cell is genetically modified to be deficient in Chsy1, Hsndst1, and Hsndst2 and modified to be transgenic for Hsndst3, Hs6st1/2, and Hs3st5. In some embodiments, the cell is genetically modified to be deficient in Chsy1, Hsndst1, and Hsndst2 and modified to be transgenic for Hsndst3, Hs6st1/2, and Hs3st6. In some embodiments, the cell is genetically modified to be deficient in Chsy1, Hsndst1, and Hsndst2 and modified to be transgenic for Hsndst4, Hs6st1/2, and Hs3st1. In some embodiments, the cell is genetically modified to be deficient in Chsy1, Hsndst1, and Hsndst2 and modified to be transgenic for Hsndst4, Hs6st1/2, and Hs3st2. In some embodiments, the cell is genetically modified to be deficient in Chsy1, Hsndst1, and Hsndst2 and modified to be transgenic for Hsndst4, Hs6st1/2, and Hs3st3a. In some embodiments, the cell is genetically modified to be deficient in Chsy1, Hsndst1, and Hsndst2 and modified to be transgenic for Hsndst4, Hs6st1/2, and Hs3st3b. In some embodiments, the cell is genetically modified to be deficient in Chsy1, Hsndst1, and Hsndst2 and modified to be transgenic for Hsndst4, Hs6st1/2, and Hs3st4. In some embodiments, the cell is genetically modified to be deficient in Chsy1, Hsndst1, and Hsndst2 and modified to be transgenic for Hsndst4, Hs6st1/2, and Hs3st5. In some embodiments, the cell is genetically modified to be deficient in Chsy1, Hsndst1, and Hsndst2 and modified to be transgenic for Hsndst4, Hs6st1/2, and Hs3st6. In some embodiments, the cell produces a heparan sulfate composition substantially free from chondroitin sulfate, dermatan sulfate, keratan sulfate, and/or hyaluronic acid. In some embodiments, the cell produces a chondroitin sulfate composition substantially free from heparan sulfate, dermatan sulfate, keratan sulfate, and/or hyaluronic acid. In some embodiments, the cell produces a dermatan sulfate composition substantially free from chondroitin sulfate, heparan sulfate, keratan sulfate, and/or hyaluronic acid. In some embodiments, the cell produces a keratan sulfate composition substantially free from chondroitin sulfate, dermatan sulfate, heparan sulfate, and/or hyaluronic acid. In some embodiments, the cell produces a hyaluronic acid composition substantially free from chondroitin sulfate, dermatan sulfate, keratan sulfate, and/or heparan sulfate. In some embodiments, the cell produces a heparan sulfate, chondroitin sulfate, dermatan sulfate, keratan sulfate, and/or hyaluronic acid with a defined pattern of sulfation. In some embodiments, the cell produces a heparan sulfate, chondroitin sulfate, dermatan sulfate, keratan sulfate, and/or hyaluronic acid that is at least 95% free from protein and nucleic acid contamination. In some embodiments, the cell produces a heparan sulfate, chondroitin sulfate, dermatan sulfate, keratan sulfate, and/or hyaluronic acid that is at least 99% free from protein and nucleic acid contamination. In some embodiments, the cell is a CHO cell, a mouse embryonic fibroblast, a 293 cell, a HeLa cell, a human fibroblast, a human embryonic stem cell, a stem cell, a an F9 cell, a human cardiac-derived progenitor cell (hCMPC), a tumor cell, or other animal cell. In some embodiments, the cell is from a mammal. In some embodiments, the cell is from a human.

Also provided herein, are methods of preparation of a substantially pure glycosaminoglycan selected from the group consisting of heparan sulfate, chondroitin sulfate, dermatan sulfate, keratan sulfate, and hyaluronic acid comprising use of any one of the cell lines of any one of the above embodiments, wherein the method comprises the steps: (a) growing any one of the cell lines of any one of the above embodiments, using an appropriate growth media, (b) isolating the growth media from the cells by centrifugation. In some embodiments, the glycosaminoglycan is heparan sulfate. In some embodiments, the heparan sulfate is substantially free from chondroitin sulfate, dermatan sulfate, keratan sulfate, and/or hyaluronic acid. In some embodiments, the glycosaminoglycan is chondroitin sulfate. In some embodiments, the chondroitin sulfate is substantially free from heparan sulfate, dermatan sulfate, keratan sulfate, and/or hyaluronic acid. In some embodiments, the glycosaminoglycan is dermatan sulfate. In some embodiments, the dermatan sulfate is substantially free from chondroitin sulfate, heparan sulfate, keratan sulfate, and/or hyaluronic acid. In some embodiments, the glycosaminoglycan is keratan sulfate. In some embodiments, the keratan sulfate is substantially free from chondroitin sulfate, dermatan sulfate, heparan sulfate, and/or hyaluronic acid. In some embodiments, the glycosaminoglycan is hyaluronic acid. In some embodiments, the hyaluronic acid is substantially free from chondroitin sulfate, dermatan sulfate, keratan sulfate, and/or heparan sulfate. In some embodiments, the method comprises fractionating the mixture by ion exchange column. In some embodiments, the method comprises removing contaminating nucleic acids by nuclease digestion. In some embodiments, the method comprises removing contaminating proteins by protease digestion. In some embodiments, the method comprises fractionating the resulting product by ion exchange. In some embodiments, the method comprises desalting. In some embodiments, the method does not require the use of an enzyme. In some embodiments, the method does not require the use of a chondroitinase. In some embodiments, the glycosaminoglycan is at least 95% free from protein and nucleic acid contamination. In some embodiments, the glycosaminoglycan is at least 99% free from protein and nucleic acid contamination.

Also provided herein are methods of making a cell line capable of producing a substantially pure glycosaminoglycan selected from the group consisting of heparan sulfate, chondroitin sulfate, dermatan sulfate, keratan sulfate, and hyaluronic acid comprising genetically modifying a cell line to be transgenic or deficient for a gene of Tables 1, 2, 4 or 5. In some embodiments, the glycosaminoglycan is heparan sulfate. In some embodiments, the heparan sulfate is substantially free from chondroitin sulfate, dermatan sulfate, keratan sulfate, and/or hyaluronic acid. In some embodiments, the glycosaminoglycan is chondroitin sulfate. In some embodiments, the chondroitin sulfate is substantially free from heparan sulfate, dermatan sulfate, keratan sulfate, and/or hyaluronic acid. In some embodiments, the glycosaminoglycan is dermatan sulfate. In some embodiments, the dermatan sulfate is substantially free from chondroitin sulfate, heparan sulfate, keratan sulfate, and/or hyaluronic acid. In some embodiments, the glycosaminoglycan is keratan sulfate. In some embodiments, the keratan sulfate is substantially free from chondroitin sulfate, dermatan sulfate, heparan sulfate, and/or hyaluronic acid. In some embodiments, the glycosaminoglycan is hyaluronic acid. In some embodiments, the hyaluronic acid is substantially free from chondroitin sulfate, dermatan sulfate, keratan sulfate, and/or heparan sulfate.

Also provided herein are kits comprising any one of the cells of any one of the above embodiments and instructions for use in preparing a substantially pure glycosaminoglycan selected from the group consisting of heparan sulfate, chondroitin sulfate, dermatan sulfate, keratan sulfate, and hyaluronic acid. In some embodiments, the kit comprises instructions for any of the methods of any one of the above embodiments.

Further provided herein are methods of treating a thrombosis, an inflammation, a cancer, a microbial infection, a neurodegenerative disorder or a wound in an individual in need thereof comprising administering an effective amount of any of the compositions of any one of the above embodiments or a pharmaceutical composition thereof. In some embodiments, the thrombosis comprises, venous thrombosis, deep vein thrombosis, portal vein thrombosis, renal vein thrombosis, jugular vein thrombosis, Budd-Chiari syndrome, Paget-Schroetter disease, Cerebral venous sinus thrombosis, Cavernous sinus thrombosis, arterial thrombosis, stroke, myocardial infarction or Hepatic artery thrombosis. In some embodiments, the inflammation comprises, rheumatoid arthritis, juvenile rheumatoid arthritis, osteoarthritis, psoriatic arthritis, multiple sclerosis (MS), encephalomyelitis, myasthenia gravis, systemic lupus erythematosus (SLE), asthma, allergic asthma, autoimmune thyroiditis, atopic dermatitis, eczematous dermatitis, psoriasis, Sjögren's Syndrome, Crohn's disease, aphthous ulcer, iritis, conjunctivitis, keratoconjunctivitis, ulcerative colitis (UC), inflammatory bowel disease (IBD), cutaneous lupus erythematosus, scleroderma, vaginitis, proctitis, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, interstitial lung fibrosis, Hashimoto's thyroiditis, autoimmune polyglandular syndrome, insulin-dependent diabetes mellitus (IDDM, type I diabetes), insulin-resistant diabetes mellitus (type 2 diabetes), immune-mediated infertility, autoimmune Addison's disease, pemphigus vulgaris, pemphigus foliaceus, dermatitis herpetiformis, autoimmune alopecia, vitiligo, autoimmune hemolytic anemia, autoimmune thrombocytopenic purpura, pernicious anemia, Guillain-Barre syndrome, stiff-man syndrome, acute rheumatic fever, sympathetic ophthalmia, Goodpasture's syndrome, systemic necrotizing vasculitis, antiphospholipid syndrome or an allergy, Behcet's disease, X-linked lymphoproliferative syndrome (SH2D1A/SAP deficiency), hyper IgE syndrome or Graft vs. Host Disease (GVHD). In some embodiments, the cancer comprises Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, or Wilms' tumor. In some embodiments, the microbial infection comprises a viral infection, a bacterial infection or a parasitic infection. In some embodiments, the neurodegenerative disorder comprises Alzheimer's disease, Parkinson's disease, Huntington's disease, Amyotrophic lateral sclerosis, Dementia, Transmissible spongiform encephalopathy, Dentatorubropallidoluysian atrophy, Spinal and bulbar muscular atrophy, Spinocerebellar ataxia Type 1, Spinocerebellar ataxia Type 2, Spinocerebellar ataxia Type 3, Spinocerebellar ataxia Type 6, Spinocerebellar ataxia Type 7, or Spinocerebellar ataxia Type 17. In some embodiments, the wound comprises an incision, a laceration, an abrasion, an avulsion, a puncture wound, a penetration wound, a gunshot wound, a hematoma, or a crush injury.

Also provided herein are compositions of any one of the above embodiments or the pharmaceutical compositions thereof for use in treating a thrombosis, an inflammation, a cancer, a microbial infection, a neurodegenerative disorder or a wound.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5A shows a portion of the GAG was incubated with chondroitinase or heparin lyases in a UV transparent plate and the resulting change in absorbance was measured. FIG. 5B shows a portion of the GAG was digested exhaustively with chondroitinase or heparin lyases. The remaining heparan sulfate or chondroitin sulfate was purified on DEAE-Sephacel and quantified by carbazole assay.

FIG. 9 shows screening colonies for altered HS structure by FGF2 binding. Clonal populations derived from limiting dilution cloning were incubated with FGF2 to identify cell lines with altered HS synthesis. A representative experiment is shown. In all, approximately 50 colonies of each targeted gene were screened.

FIG. 10A shows amino acid sequences of NDST2 in the NDST1/NDST2 double KO of clone ChA27 aligned with the unmodified sequence. Eight amino acids are missing in the KO. Amino acid sequences were obtained from DNA sequence analyses of PCR products amplified using primers flanking the CRISPR/Cas genetic target site.

FIG. 10B shows amino acid sequences of HS2ST in the HS2ST KO of clone ChA27 aligned with the unmodified sequence. A one base pair insertion forms a premature stop codon at the position of amino acid 198. Amino acid sequences were obtained from DNA sequence analyses of PCR products amplified using primers flanking the CRISPR/Cas genetic target site.

DETAILED DESCRIPTION OF THE INVENTION

Figure 1:
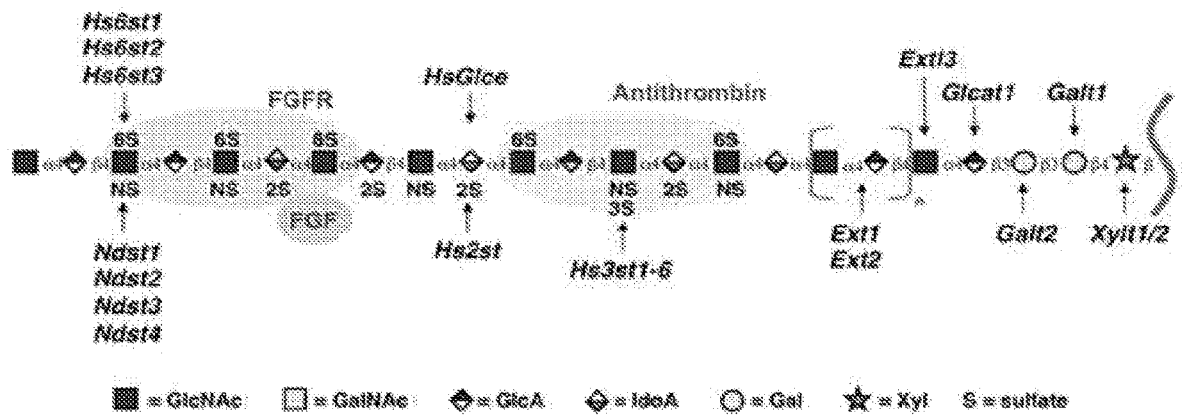
FIG. 1 shows a schematic of a HS chain illustrating binding sites for antithrombin and FGF/FGFR. The various genes required for HS biosynthesis are indicated in italics. Xylt, xylosyltransferase; Galt, galactosyltransferase; Ext, exostosins, GlcNAc and GlcA transferases; Ndst, GlcNAc N-deacetylase/N-sulfotransferase; Hs6st, glucosaminyl 6-O-sulfotransferase; Hs3st, glucosaminyl 3-O-sulfotransferae; Hs2st, uronyl 2-O-sulfotransferase; HsGlce, uronyl C5 epimerase.

Glycosaminoglycans (GAGs) display heterogeneity in mass, disaccharide composition and pattern of sulfation which originates in their synthesis by cellular enzymes. GAGs are classified into four groups based on their core disaccharide structure: heparan sulfate (HS), chondroitin sulfate (CS)/dermatan sulfate (DS), keratan sulfate (KS), and hyaluronic acid (HA). Proteins are further modified (i.e., glycosylated) in the cell with various diverse GAGs thereby creating proteoglycans.

Disclosed herein are GAGs purified from genetically modified cells that comprise uniform compositions of at least one specific GAG that is substantially free from one or more contaminating GAGs. In some embodiments, the composition is a heparan sulfate that is substantially free of contamination from one or more GAGs selected from a chondroitin sulfate, dermatan sulfate, a keratan sulfate and a hyaluronic acid. In some embodiments, the composition is a chondroitin sulfate/dermatan sulfate that is substantially free of contamination from one or more GAGs selected from a heparan sulfate, a keratan sulfate and a hyaluronic acid. In some embodiments, the composition is a keratan sulfate that is substantially free of contamination from one or more GAGs selected from a heparan sulfate, a chondroitin sulfate, dermatan sulfate, and a hyaluronic acid. In some embodiments, the composition is a hyaluronic acid that is substantially free of contamination from one or more GAGs selected from a heparan sulfate, a chondroitin sulfate dermatan sulfate, and a keratan keratan sulfate.

GAGs are modified from their core disaccharide chain to create diversity within each type of GAG. Modifications include sulfation, deacetylation, and epimerization. Also disclosed herein are GAGs that comprise a specific GAG with a defined pattern of sulfation. In some embodiments the GAG comprises one or more of a GAG selected from a heparan sulfate, a chondroitin sulfate, a dermatan sulfate, and a keratan sulfate, each of which has a defined pattern of sulfation. In some embodiments the GAG comprises one or more of a GAG selected from a heparan sulfate, a chondroitin sulfate, a dermatan sulfate, and a keratan sulfate each of which has a defined pattern of epimerization. In some embodiments the GAG is a heparan sulfate with a defined pattern of sulfation. In some embodiments, the GAG is a heparan sulfate with a defined pattern of epimerization.

Heparan Sulfate Compositions

Heparan sulfate plays important roles in cellular and tissue specific physiology, pathophysiology and development because heparan sulfate specifically binds to a wide variety of proteins. In some embodiments proteins include enzymes, extracellular signaling molecules, chemokines, lipid- or membrane-binding proteins, adhesion proteins and pathogenic proteins. In some embodiments, the heparan sulfate of the compositions and methods disclosed herein can be used to affect inflammatory processes, stem cell differentiation, normal and cancer cell growth and differentiation, blood cell differentiation, cell-cell and cell-matrix interactions, lipid transport and clearance/metabolism, host defense and viral and bacterial infection.

Diversity in heparan sulfate compositions or patterns of modification is introduced into short oligomeric regions along the heparan sulfate chains via modifications. In some embodiments, these modifications create specific protein binding sites on the heparan sulfate. In some embodiments, the modifications include adding sulfate groups four to or more positions on carbohydrate residues within the disaccharides and epimerization of glucuronic acid residues to create iduronic acid. In yet other embodiments, these modifications do not run to completion, thereby creating heparan sulfate chains that contain a wide variety of oligomeric structures. In some cases, specific protein binding to oligosaccharides on the heparan sulfate chains is determined by the degree and pattern of sulfation within the oligosaccharide.

Heparan sulfate is composed of linear chains of repeating disaccharides (glucuronic acid beta 1-4 linked to N-acetylglucosamine) that are polydisperse ranging from 5 to 50 kDa with an average molecular weight of 30 kDa. Certain positions in the sugar residues can be modified including N-deacetylation or N-deacetylation and N-sulfation at position C2 of N-acetylglucosamine residues resulting in glucosamine or N-sulfated glucosamine. Glucosamine residues can also be O-sulfated at positions 3 and 6 although 3-O-sulfation is rare and much more prevalent in pharmaceutical heparin. The C2 position of glucuronic acid can be O-sulfated although this is much more common upon prior epimerization of glucuronic acid to iduronic acid. Epimerization also changes the linkage between the iduronic acid and the subsequent residue from beta 1-4 to alpha 1-4 and this modification is also much more prevalent in heparin. Heparan sulfate consist of up to 100 disaccharide units where the disaccharide units are modified to varying degrees throughout the heparan sulfate chains. Particular sub-regions of the chains are highly sulfated where as other regions are moderately sulfated or unsulfated. The step-by-step mechanism establishing overall level and pattern of these modifications in vivo are not well understood however O-sulfation and epimerization typically follow N-sulfation.

Provided in certain embodiments herein are heparan sulfate compositions with specific patterns of modification derived from cell lines capable of specific heparan sulfate biosynthesis. In various embodiments, specific heparan sulfate biosynthesis, as used herein, includes, by way of non-limiting example, (1) increasing or decreasing in cell lines via genetic modification (a) heparan sulfate polymerization; (b) heparan sulfate sulfation; (c) epimerization of uronic acid groups in heparan sulfate; (d) heparan sulfate phosphorylation and/or (e) deacetylation of GlcNAc groups in heparan sulfate; and/or (2) promotion of (a) heparan sulfate bond cleavage; (b) bond cleavage of the linker region connecting heparan sulfate to a core protein; (c) bond cleavage between heparan sulfate and the linker region; (d) sulfation (e.g., N-sulfation and/or O-sulfation) of heparan sulfate; (e) acetylation of GlcN groups in heparan sulfate; (f) deacetylation of GlcNAc groups in heparan sulfate; (g) heparan sulfate phosphorylation, and/or (h) epimerization of uronic acid groups in heparan sulfate. In specific embodiments, the genetic modification of cell lines inhibits sulfation of heparan sulfate. In specific embodiments, the genetic modification of cell lines increases sulfation of heparan sulfate. In yet other embodiments, the genetic modification of cell lines inhibits epimerization of heparan sulfate. In specific embodiments, the genetic modification of cell lines increases epimerization of heparan sulfate.

In some embodiments, the heparan sulfate composition is derived from a cell line with a genetic modification that modulates (e.g., increases or inhibits) glycosyltransferases. In some embodiments, the heparan sulfate composition is derived from a cell line with a genetic modification that inhibits the synthesis of the linkage region suitable for connecting heparan sulfate to a core protein, the initiation of heparan sulfate synthesis, the synthesis of heparan sulfate, or a combination thereof. In some embodiments, the heparan sulfate composition is derived from a cell line with a genetic modification that modulates (e.g., increases or inhibits) one or more of a heparan sulfate xylosyltransferases, a heparan sulfate galactosyltransferase, a heparan sulfate glucuronosyltransferase, a heparan sulfate N-acetylglucosamine transferase, or combinations thereof. In more specific embodiments, the genetic modification of cell lines modulates (e.g., increases or decreases) one or more of xylosyltransferase I, xylosyltransferase II, galactosyltransferase I, galactosyltransferase II, glucuronosyltransferase I, glucuronosyltransferase II, N-acetylglucosamine transferase I, N-acetylglucosamine transferase II, or a combination thereof.

In certain embodiments, the heparan sulfate composition is derived from a cell line with genetic modifications that modulate sulfation, specifically a cell line that is genetically modified for one or more sulfotransferase. In specific embodiments, the heparan sulfate composition is derived from a cell line that is genetically modified, by way of non-limiting example, to modulate (e.g., inhibit or increase) one or more of a heparan sulfate O-sulfotransferase, a heparan sulfate N-sulfotransferase, or a combination thereof. In more specific embodiments, the genetically modified cell line modulates (e.g., inhibits or increases) a heparan sulfate O-sulfotransferase such as, by way of non-limiting example, one or more of a 6-O sulfotransferase (of a glucosamine group), a 3-O sulfotransferase (of a glucosamine group), a 2-O sulfotransferase (of a uronic acid moiety, e.g., glucuronic acid or iduronic acid), a 6-O sulfotransferase (of a galactose in the linkage tetrasaccharide), or a combination thereof. In some embodiments, genetically modified cell lines modulate 2-O phosphorylation of the xylose in the linkage tetrasaccharide.

In certain embodiments, the heparan sulfate composition is derived from a genetically modified cell line that alters or disrupts the nature (e.g., alters or disrupts the N-acetylation, N-sulfation, the 2-O sulfation, the 3-O sulfation, and the 6-O sulfation content of heparan sulfate, epimerization of heparan sulfate, chain length of heparan sulfate (or a combination thereof) of heparan sulfate compared to endogenous heparan sulfate in an amount sufficient to create a heparan sulfate composition with altered or disrupted heparan sulfate binding of protein ligands, heparan sulfate-dependent signaling pathways, or a combination thereof. In specific embodiments, the genetically modified cell line alters the nature of the heparan sulfate such that it alters heparan sulfate signaling. In other specific embodiments, the genetically modified cell line alters the nature of the heparan sulfate such that it alters heparan sulfate binding to proteins. In more specific embodiments, the genetically modified cell line alters the nature of the heparan sulfate such that it alters heparan sulfate binding and heparan sulfate signaling. In some embodiments, the genetically modified cell line alters the nature of the heparan sulfate such that it alters the binding, signaling, or a combination thereof of any protein (including polypeptides) subject to heparan sulfate binding, signaling or a combination thereof, in the absence of a heparan sulfate inhibitor. In some embodiments, the protein is, by way of non-limiting example, a growth factor. In specific embodiments, the growth factor is, by way of non-limiting example, fibroblast growth factor (FGF) or vascular endothelia growth factor (VEGF).

Although heparin-binding consensus sequences have been identified in some proteins, the mechanisms of binding are variable. From the standpoint of heparan sulfate, the degree of sulfation and the sulfation pattern can increase the affinity of short oligomeric regions for certain amino acid sequences (typically involving basic amino acids), both chemically (ionic) and geometrically.

Many of the functions ascribed to heparan sulfate have been deduced by binding and competition studies with commercial heparin, which is available in abundant quantities and can be broken down into fragments or chemically modified. However, heparin is a fractionated highly sulfated form of heparan sulfate derived from porcine entrails and has high antithrombin binding capacity and anticoagulant activity. The high degree of sulfation endows heparin with strong cation exchange properties and does not mimic naturally occurring heparan sulfate, which has a much lower degree of sulfation and generally lacks anticoagulant activity. Attempts to obtain heparin-like molecules by synthetic or chemoenzymatic methods have advanced significantly over the last decade, but most of the available material is based on the structure of heparin and consists of oligosaccharides ranging from dp2-dp12, which does not duplicate the length or compositional diversity of naturally occurring HS. In most cases, the templates used to guide oligosaccharide assembly are based on a few characterized binding sites for known ligands. Furthermore, short oligomeric sequences do not replicate the organization of sulfated domains on longer heparan sulfate chains.

Chondroitin Sulfate Compositions

Chondroitin sulfate is a sulfated glycosaminoglycan (GAG) composed of a chain of alternating sugars (N-acetyl-galactosamine and glucuronic acid). Chondroitin sulfate chains are unbranched polysaccharides of variable length containing two alternating monosaccharides: D-glucuronic acid (GlcA) and N-acetyl-D-galactosamine (GalNAc). Some GlcA residues are epimerized into L-iduronic acid (IdoA); the resulting disaccharide is then referred to as dermatan sulfate. It is usually found attached to proteins as part of a proteoglycan. A chondroitin sulfate chain can have over 100 individual sugars, each of which can be sulfated in variable positions and quantities. Chondroitin sulfate chains are linked to hydroxyl groups on serine residues of certain proteins. Exactly how proteins are selected for attachment of glycosaminoglycans is not understood. Glycosylated serines are often followed by a glycine and have neighboring acidic residues, but this motif does not always predict glycosylation. Attachment of the GAG chain begins with four monosaccharides in a fixed pattern: Xyl-Gal-Gal-GlcA. Each sugar is attached by a specific enzyme, allowing for multiple levels of control over GAG synthesis. Xylose is attached to proteins in the endoplasmic reticulum, while the rest of the sugars are attached to the chain in the Golgi apparatus. Each monosaccharide may be left unsulfated, sulfated once, or sulfated twice. In the most common scenario, the hydroxyls of the 4 and 6 positions of the N-acetyl-galactosamine are sulfated, with some chains having the 2 position of glucuronic acid. Sulfation is mediated by specific sulfotransferases. Sulfation in these different positions confers specific biological activities to chondroitin GAG chains.

Chondroitin sulfate is a major component of extracellular matrix, and is important in maintaining the structural integrity of the tissue. This function is typical of the large aggregating proteoglycans: aggrecan, versican, brevican, and neurocan, collectively termed the lecticans.

As part of aggrecan, chondroitin sulfate is a major component of cartilage. The tightly packed and highly charged sulfate groups of chondroitin sulfate generate electrostatic repulsion that provides much of the resistance of cartilage to compression. Loss of chondroitin sulfate from the cartilage is a major cause of osteoarthritis. The effect of chondroitin sulfate in patients with osteoarthritis is likely the result of a number of reactions including its anti-inflammatory activity, the stimulation of the synthesis of proteoglycans and hyaluronic acid, and the decrease in catabolic activity of chondrocytes inhibiting the synthesis of proteolytic enzymes, nitric oxide, and other substances that contribute to damage cartilage matrix and cause death of articular chondrocytes. Chondroitin sulfate has been found to reduce IL-10-induced nuclear factor-kB (NF-κB) translocation in chondrocytes.

Chondroitin sulfate readily interacts with proteins in the extracellular matrix due to its negative charges. These interactions are important for regulating a diverse array of cellular activities. The lecticans are a major part of the brain extracellular matrix, where the chondroitin sugar chains function to stabilize normal brain synapses as part of perineuronal nets. The levels of chondroitin sulfate proteoglycans are vastly increased after injury to the central nervous system where they act to prevent regeneration of damaged nerve endings. Although these functions are not as well characterized as those of heparan sulfate, new roles continue to be discovered for the chondroitin sulfate proteoglycans.

In cortical development, chondroitin sulfate is expressed by the Sub Plate and acts as a stop signal for neurons migrating from the Ventricular Zone. Neurons stopping here may then be programmed for further migration to specific layers in the cortical plate.

Chondroitin's functions depend largely on the properties of the overall proteoglycan of which it is a part. These functions can be broadly divided into structural and regulatory roles. However, this division is not absolute, and some proteoglycans have both structural and regulatory roles.

Provided in certain embodiments herein are chondroitin sulfate compositions with specific patterns of modification derived from cell lines capable of specific chondroitin sulfate biosynthesis. In various embodiments, specific chondroitin sulfate biosynthesis, as used herein, includes, by way of non-limiting example, (1) increasing or decreasing in cell lines via genetic modification (a) chondroitin sulfate polymerization; (b) chondroitin sulfate sulfation; (c) chondroitin sulfate phosphorylation and/or (d) deacetylation of GlcNAc groups in chondroitin sulfate; and/or (2) promotion of (a) chondroitin sulfate bond cleavage; (b) bond cleavage of the linker region connecting chondroitin sulfate to a core protein; (c) bond cleavage between chondroitin sulfate and the linker region; (d) sulfation (e.g., N-sulfation and/or O-sulfation) of chondroitin sulfate; (e) acetylation of GalN groups in chondroitin sulfate; (f) deacetylation of GlcNAc groups in chondroitin sulfate; and/or (g) chondroitin sulfate phosphorylation. In specific embodiments, the genetic modification of cell lines inhibits sulfation of chondroitin sulfate. In specific embodiments, the genetic modification of cell lines increases sulfation of chondroitin sulfate. In some embodiments, the genetic modification of cell lines inhibits epimerization of chondroitin sulfate. In some embodiments, the genetic modification of cell lines increases epimerization of chondroitin sulfate.

In some embodiments, the chondroitin sulfate composition is derived from a cell line with a genetic modification that modulates (e.g., increases or inhibits) glycosyltransferases. In some embodiments, the chondroitin sulfate composition is derived from a cell line with a genetic modification that inhibits the synthesis of the linkage region suitable for connecting chondroitin sulfate to a core protein, the initiation of chondroitin sulfate synthesis, the synthesis of chondroitin sulfate, or a combination thereof. In some embodiments, the chondroitin sulfate composition is derived from a cell line with a genetic modification that modulates (e.g., increases or inhibits) one or more of a chondroitin sulfate GaNAc transferases, a chondroitin sulfate galactosyltransferase, a chondroitin sulfate glucuronosyltransferase, a chondroitin sulfate N-acetylglucosamine synthase, a chondroitin sulfate polymerizing factor, or combinations thereof. In more specific embodiments, the genetic modification of cell lines modulates (e.g., increases or decreases) one or more of GaNAc transferase 1, GaNAc transferase 2, Chondroitin sulfate synthase 1, Chondroitin sulfate synthase 2, Chondroitin sulfate synthase 3, Chondroitin sulfate polymerizing factor, Chondroitin sulfate polymerizing factor 2, or a combination thereof.

In certain embodiments, the chondroitin sulfate composition is derived from a cell line with genetic modifications that modulate sulfation, specifically a cell line that is genetically modified for one or more sulfotransferase. In specific embodiments, the chondroitin sulfate composition is derived from a cell line that is genetically modified, by way of non-limiting example, to modulate (e.g., inhibit or increase) a chondroitin sulfate O-sulfotransferase. In more specific embodiments, the genetically modified cell line modulates (e.g., inhibits or increases) a chondroitin sulfate O-sulfotransferase such as, by way of non-limiting example, one or more of a chondroitin 4-O-sulfotransferase 1, chondroitin 4-O-sulfotransferase 2, chondroitin 4-O-sulfotransferase 3, chondroitin 4-O-sulfotransferase 5, chondroitin 6-O sulfotransferase, chondroitin 6-Osulfotransferase 2, or a combination thereof. In some embodiments, genetically modified cell lines modulate 2-O phosphorylation of the xylose in the linkage tetrasaccharide.

In certain embodiments, the chondroitin sulfate composition is derived from a genetically modified cell line that alters or disrupts the nature (e.g., alters or disrupts the N-acetylation, the 4-O sulfation, and the 6-O sulfation content of chondroitin sulfate, epimerization of chondroitin sulfate, chain length of chondroitin sulfate (or a combination thereof) of chondroitin sulfate in an amount sufficient to create a chondroitin sulfate composition with altered or disrupted chondroitin sulfate binding of protein ligands, chondroitin sulfate-dependent signaling pathways, or a combination thereof. In specific embodiments, the genetically modified cell line alters the nature of the chondroitin sulfate such that it alters chondroitin sulfate signaling. In other specific embodiments, the genetically modified cell line alters the nature of the chondroitin sulfate such that it alters chondroitin sulfate binding to proteins. In more specific embodiments, the genetically modified cell line alters the nature of the chondroitin sulfate such that it alters chondroitin sulfate binding and chondroitin sulfate signaling. In some embodiments, the genetically modified cell line alters the nature of the chondroitin sulfate such that it alters the binding, signaling, or a combination thereof of any protein (including polypeptides) subject to chondroitin sulfate binding, signaling or a combination thereof, in the absence of a chondroitin sulfate inhibitor.

Dermatan Sulfate Compositions

Dermatan sulfate is a modified form of chondroitin sulfate in which a portion of the D-glucuronate residues are epimerized to L-iduronates. Dermatan sulfate is mostly found in skin, but is also present in blood vessels, heart valves, tendons, and lungs. Dermatan sulfate is thought to have roles in physiological processes including but not limited to coagulation, cardiovascular disease, carcinogenesis, infection, wound repair, and fibrosis. Abnormal accumulation of dermatan sulfate is observed in mucopolysaccharidosis disorders and in cardiovascular mitral valve degeneration including mitral valve prolapse and mitral valve insufficiency.

Provided in certain embodiments herein are dermatan sulfate compositions with specific patterns of modification derived from cell lines capable of specific dermatan sulfate biosynthesis. In various embodiments, specific dermatan sulfate biosynthesis, as used herein, includes, by way of non-limiting example, (1) increasing or decreasing in cell lines via genetic modification (a) dermatan sulfate polymerization; (b) dermatan sulfate sulfation; (c) epimerization of glucuronic acid groups in dermatan sulfate; (d) dermatan sulfate phosphorylation and/or (e) deacetylation of GlcNAc groups in dermatan sulfate; and/or (2) promotion of (a) dermatan sulfate bond cleavage; (b) bond cleavage of the linker region connecting dermatan sulfate to a core protein; (c) bond cleavage between dermatan sulfate and the linker region; (d) sulfation (e.g., N-sulfation and/or O-sulfation) of dermatan sulfate; (e) acetylation of GalN groups in dermatan sulfate; (f) deacetylation of GlcNAc groups in dermatan sulfate; (g) dermatan sulfate phosphorylation, and/or (h) epimerization of glucuronic acid groups in dermatan sulfate. In specific embodiments, the genetic modification of cell lines inhibits sulfation of dermatan sulfate. In specific embodiments, the genetic modification of cell lines increases sulfation of dermatan sulfate. In yet other embodiments, the genetic modification of cell lines inhibits epimerization of dermatan sulfate. In specific embodiments, the genetic modification of cell lines increases epimerization of dermatan sulfate.

In some embodiments, the dermatan sulfate composition is derived from a cell line with a genetic modification that modulates (e.g., increases or inhibits) glycosyltransferases. In some embodiments, the dermatan sulfate composition is derived from a cell line with a genetic modification that inhibits the synthesis of the linkage region suitable for connecting dermatan sulfate to a core protein, the initiation of dermatan sulfate synthesis, the synthesis of dermatan sulfate, or a combination thereof. In some embodiments, the dermatan sulfate composition is derived from a cell line with a genetic modification that modulates (e.g., increases or inhibits) one or more of a chondroitin sulfate GaNAc transferases, a chondroitin sulfate galactosyltransferase, a chondroitin sulfate glucuronosyltransferase, a chondroitin sulfate N-acetylglucosamine synthase, a chondroitin sulfate polymerizing factor, or combinations thereof. In more specific embodiments, the genetic modification of cell lines modulates (e.g., increases or decreases) one or more of GaNAc transferase 1, GaNAc transferase 2, Chondroitin sulfate synthase 1, Chondroitin sulfate synthase 2, Chondroitin sulfate synthase 3, Chondroitin sulfate polymerizing factor, Chondroitin sulfate polymerizing factor 2, or a combination thereof.

In certain embodiments, the dermatan sulfate composition is derived from a cell line with genetic modifications that modulate sulfation, specifically a cell line that is genetically modified for one or more sulfotransferase. In specific embodiments, the dermatan sulfate composition is derived from a cell line that is genetically modified, by way of non-limiting example, to modulate (e.g., inhibit or increase) a dermatan sulfate O-sulfotransferase. In more specific embodiments, the genetically modified cell line modulates (e.g., inhibits or increases) a dermatan sulfate O-sulfotransferase such as, by way of non-limiting example, dermatan sulfate 4-O-sulfotransferase. In some embodiments, the genetically modified cell line modulates (e.g., inhibits or increases) a dermatan sulfate epimerase, such as, by way of non-limiting examples dermatan sulfate glucuronyl C5 epimerase 1, dermatan sulfate glucuronyl C5 epimerase-like, or combinations thereof. In some embodiments, genetically modified cell lines modulate 2-0 phosphorylation of the xylose in the linkage tetrasaccharide.

In certain embodiments, the dermatan sulfate composition is derived from a genetically modified cell line that alters or disrupts the nature (e.g., alters or disrupts the N-acetylation, the 4-O sulfation, and the 6-O sulfation content of dermatan sulfate, epimerization of dermatan sulfate, chain length of dermatan sulfate (or a combination thereof) of dermatan sulfate compared to naturally occurring dermatan sulfate in an amount sufficient to create a dermatan sulfate composition with altered or disrupted dermatan sulfate binding of protein ligands, dermatan sulfate-dependent signaling pathways, or a combination thereof. In specific embodiments, the genetically modified cell line alters the nature of the dermatan sulfate such that it alters dermatan sulfate signaling. In other specific embodiments, the genetically modified cell line alters the nature of the dermatan sulfate such that it alters dermatan sulfate binding to proteins. In more specific embodiments, the genetically modified cell line alters the nature of the dermatan sulfate such that it alters dermatan sulfate binding and dermatan sulfate signaling. In some embodiments, the genetically modified cell line alters the nature of the dermatan sulfate such that it alters the binding, signaling, or a combination thereof of any protein (including polypeptides) subject to dermatan sulfate binding, signaling or a combination thereof, in the absence of a dermatan sulfate inhibitor.

Keratan Sulfate Compositions

Keratan sulfate (KS), also called keratosulfate, is any of several sulfated glycosaminoglycans (structural carbohydrates) that have been found especially in the cornea, cartilage, and bone. It is also synthesized in the central nervous system where it participates both in development and in the glial scar formation following an injury. Keratan sulfates are large, highly hydrated molecules which in joints can act as a cushion to absorb mechanical shock.

Like other glycosaminoglycans, keratan sulfate is a linear polymer that consists of a repeating disaccharide unit. Keratan sulfate occurs as a proteoglycan in which keratan sulfate chains are attached to cell-surface or extracellular matrix proteins, termed core proteins. Keratan sulfate core proteins include Lumican, Keratocan, Mimecan, Fibromodulin, PRELP, Osteoadherin and Aggrecan. The basic repeating disaccharide unit within keratan sulfate is –3Galβ1-4GcNAcβ1-. This can be sulfated at carbon position 6 (C6) of either or both the Gal or GlcNAc monosaccharides. However, the detailed primary structure of specific keratan sulfate types are best considered to be composed of three regions: 1) linkage region, at one end of which the keratan sulfate chain is linked to the core protein, 2) a repeat region, composed of the –3Galβ1-4GlcNAcβ1– repeating disaccharide unit, and 3) a chain capping region, occurring at the opposite end of the keratan sulfate chain to the protein linkage region. The monosaccharide mannose is found within the linkage region of keratan sulfate type I (KSI). Disaccharides within the repeating region of KSII may be fucosylated and N-Acetylneuraminic acid caps the end of all keratan sulfate type II (KSII) chains and up to 70% of KSI type chains.

Provided in certain embodiments herein are keratan sulfate compositions with specific patterns of modification derived from cell lines capable of specific keratan sulfate biosynthesis. In various embodiments, specific keratan sulfate biosynthesis, as used herein, includes, by way of non-limiting example, (1) increasing or decreasing in cell lines via genetic modification (a) keratan sulfate polymerization; (b) keratan sulfate sulfation; (c) epimerization of groups in keratan sulfate; (d) keratan sulfate phosphorylation and/or (e) deacetylation of groups in keratan sulfate; and/or (2) promotion of (a) keratan sulfate bond cleavage; (b) bond cleavage of the linker region connecting keratan sulfate to a core protein; (c) bond cleavage between keratan sulfate and the linker region; (d) sulfation (e.g., N-sulfation and/or O-sulfation) of keratan sulfate; (e) acetylation of groups in keratan sulfate; (f) deacetylation of groups in keratan sulfate; (g) keratan sulfate phosphorylation, and/or (h) epimerization of groups in keratan sulfate. In specific embodiments, the genetic modification of cell lines inhibits sulfation of keratan sulfate. In specific embodiments, the genetic modification of cell lines increases sulfation of keratan sulfate. In yet other embodiments, the genetic modification of cell lines inhibits epimerization of keratan sulfate. In specific embodiments, the genetic modification of cell lines increases epimerization of keratan sulfate.

In some embodiments, the keratan sulfate composition is derived from a cell line with a genetic modification that modulates (e.g., increases or inhibits) glycosyltransferases. In some embodiments, the keratan sulfate composition is derived from a cell line with a genetic modification that inhibits the synthesis of the linkage region suitable for connecting keratan sulfate to a core protein, the initiation of keratan sulfate synthesis, the synthesis of keratan sulfate, or a combination thereof.

In certain embodiments, the keratan sulfate composition is derived from a cell line with genetic modifications that modulate sulfation, specifically a cell line that is genetically modified for one or more sulfotransferase. In some embodiments, the genetically modified cell line modulates (e.g., inhibits or increases) a keratan sulfate epimerase.

In certain embodiments, the keratan sulfate composition is derived from a genetically modified cell line that alters or disrupts the nature (e.g., alters or disrupts the N-acetylation, the 4-O sulfation, and the 6-O sulfation content of keratan sulfate, epimerization of keratan sulfate, chain length of keratan sulfate (or a combination thereof) of keratan sulfate compared to naturally occurring keratan sulfate in an amount sufficient to create a keratan sulfate composition with altered or disrupted keratan sulfate binding of protein ligands, keratan sulfate-dependent signaling pathways, or a combination thereof. In specific embodiments, the genetically modified cell line alters the nature of the keratan sulfate such that it alters keratan sulfate signaling. In other specific embodiments, the genetically modified cell line alters the nature of the keratan sulfate such that it alters keratan sulfate binding to proteins. In more specific embodiments, the genetically modified cell line alters the nature of the keratan sulfate such that it alters keratan sulfate binding and keratan sulfate signaling. In some embodiments, the genetically modified cell line alters the nature of the keratan sulfate such that it alters the binding, signaling, or a combination thereof of any protein (including polypeptides) subject to keratan sulfate binding, signaling or a combination thereof, in the absence of a keratan sulfate inhibitor.

Hyaluronic Acid Compositions

Hyaluronic acid, also called hyaluronan, is an anionic, nonsulfated glycosaminoglycan distributed widely throughout connective, epithelial, and neural tissues. It is unique among glycosaminoglycans in that it is nonsulfated, forms in the plasma membrane instead of the Golgi apparatus, and can be very large, with its molecular weight often reaching the millions. One of the chief components of the extracellular matrix, hyaluronan contributes significantly to cell proliferation and migration, and may also be involved in the progression of some malignant tumors.

Hyaluronan is the only glycosaminoglycan synthesized in the cytoplasm at the plasma membrane, where the growing polymer is extruded into the extracellular environment. Accordingly, hyaluronan can have an indefinite and very large degree of polymerization, typically in the range of $10^4$ disaccharides (~$3.7 \times 10^6$ D as the sodium salt) and with an end-to-end length of approximately 10 μm (~1 nm/disaccharide). Thus, a single molecule of hyaluronan could stretch about halfway around the circumference of a typical mammalian cell. The carboxyl groups on the glucuronic acid residues (pKa 4-5) are predominantly negatively charged at physiological pH and ionic strength, making hyaluronan polyanionic. The anionic nature of hyaluronan together with spatial restrictions around the glycosidic bonds confer a relatively stiff, random coil structure to individual hyaluronan molecules in most biological settings. Hyaluronan chains occupy a large hydrodynamic volume such that individual molecules of high molecular weight in a 3-5 mg/ml physiological solution occupy essentially all of the solvent. This arrangement creates a size-selective barrier in which small molecules can diffuse freely, whereas larger molecules are partially or completely excluded. Such a solution would have a swelling pressure and exhibit high viscosity with viscoelastic properties, conditions found in the vitreous humor of the human eye and in joints. Hyaluronan in synovial fluids of articular joints is essential for distributing load during joint motion and for protecting the cartilaginous surfaces. Thus, in both eye and joint tissues, the physical properties of hyaluronan relate directly to tissue function.

Provided in certain embodiments herein are hyaluronan compositions with specific patterns of modification derived from cell lines capable of specific hyaluronan biosynthesis. In various embodiments, specific hyaluronan biosynthesis, as used herein, includes, by way of non-limiting example, (1) increasing or decreasing in cell lines via genetic modification (a) hyaluronan polymerization; (b) hyaluronan phosphorylation and/or (c) deacetylation of groups in hyaluronan; and/or (2) promotion of (a) hyaluronan bond cleavage; (b) hyaluronan of the linker region connecting hyaluronan to a core protein; (c) bond cleavage between hyaluronan and the linker region; (d) acetylation of groups in hyaluronan; (e) deacetylation of groups in hyaluronan; and/or (f) hyaluronan phosphorylation.

In some embodiments, the hyaluronan composition is derived from a cell line with a genetic modification that modulates (e.g., increases or inhibits) glycosyltransferases. In some embodiments, the hyaluronan composition is derived from a cell line with a genetic modification that inhibits the synthesis of the linkage region suitable for connecting hyaluronan to a core protein, the initiation of hyaluronan synthesis, the synthesis of hyaluronan, or a combination thereof.

In certain embodiments, the hyaluronan composition is derived from a genetically modified cell line that alters or disrupts the nature of hyaluronan compared to naturally occurring hyaluronan in an amount sufficient to create a hyaluronan composition with altered or disrupted hyaluronan binding of protein ligands, hyaluronan-dependent signaling pathways, or a combination thereof. In specific embodiments, the genetically modified cell line alters the nature of the hyaluronan such that it alters hyaluronan signaling. In other specific embodiments, the genetically modified cell line alters the nature of the hyaluronan such that it alters hyaluronan binding to proteins. In more specific embodiments, the genetically modified cell line alters the nature of the hyaluronan such that it alters hyaluronan binding and hyaluronan signaling. In some embodiments, the genetically modified cell line alters the nature of the hyaluronan such that it alters the binding, signaling, or a combination thereof of any protein (including polypeptides) subject to hyaluronan binding, signaling or a combination thereof, in the absence of a hyaluronan inhibitor.

Cellular Production

Although all animal cells make glycosaminoglycans such as heparan sulfate, chondroitin sulfate, dermatan sulfate, keratan sulfate, and hyaluronic acid, the size, composition, disaccharide composition and distribution of the sulfated domains vary significantly. The different arrangements of the disaccharide subunits and the sulfated domains are important, because they determine the protein ligand binding characteristics and therefore the biological properties of the chains. Glycosaminoglycans such as heparan sulfate, chondroitin sulfate, dermatan sulfate, keratan sulfate, and hyaluronic acid from cultured cells display the relevant size, disaccharide composition and distribution of sulfated domains similar to what is seen in animal tissues. Cellular expression facilitates the production of glycosaminoglycans such as heparan sulfate, chondroitin sulfate, dermatan sulfate, keratan sulfate, and hyaluronic acid in a reproducible manner at a scale that will allow investigators to examine the biological properties of glycosaminoglycans such as heparan sulfate, chondroitin sulfate, dermatan sulfate, keratan sulfate, and hyaluronic acid and to fractionate and identify biologically relevant sequences, which can then serve as models for synthesis of biologically relevant oligosaccharides.

Cell surface and extracellular matrix glycosaminoglycan structures, such as heparan sulfate, chondroitin sulfate, keratan sulfate, and hyaluronic acid, vary widely but reproducibly in tissue, development stage, and pathophysiologic specific manners. For example, the heparan sulfate chains are synthesized and subsequently modified by over 25 specific enzymes in the heparan sulfate biosynthetic pathway (FIG. 1). In turn, the different heparan sulfate compositions in different cell types and tissues are the result of different expression patterns of the enzymes in the heparan sulfate biosynthetic pathway. Disclosed herein are methods and resultant compositions by engineering the composition of the cell surface and secreted glycosaminoglycan chains in cell cultures, for example Chinese Hamster Ovary (CHO) cells, by altering the expression pattern of the biosynthetic enzymes by transfection or mutation. Accordingly, disclosed herein are cells engineered to produce glycosaminoglycans such as heparan sulfate, chondroitin sulfate, dermatan sulfate, keratan sulfate, and hyaluronic acid with reproducible composition, sulfation patterns and ligand binding properties. Also disclosed herein are methods of production of gram scale of glycosaminoglycans such as heparan sulfate, chondroitin sulfate, dermatan sulfate, keratan sulfate, and hyaluronic acid compositions at decreased cost.

Described herein is the use of a cellular expression system to produce glycosaminoglycans such as heparan sulfate, chondroitin sulfate, dermatan sulfate, keratan sulfate, and hyaluronic acid in various compositions or defined sulfation patterns in a reproducible manner at a scale that will allow investigators to examine the biological properties of the glycosaminoglycan. In some embodiments, the cellular expression system comprises a genetically modified cell from which a heparan sulfate composition with a defined pattern of sulfation is derived. In some embodiments, the genetically modified cell is deficient in one or more genes that encode an enzyme that modifies a heparan sulfate chain. In some embodiments the genetically modified cell is transgenic for one or more genes that encode an enzyme that modifies a heparan sulfate chain. In some embodiments, the gene encodes an enzyme that modifies a heparan sulfate chain selected from one or more of a sulfatase, an N-deacetylase, a synthase, an acetylgalactosaminyltransferase, a polymerizing factor, a sulphotransferase, an epimerase, an N-deacetylase/sulfotransferase, a sulfatase, a beta-glucuronidase, an iduronidase, a sulfamidase, an N-acetyltransferase, an N-acetylglucosaminidase, a xylosyltransferase, a galactosyltransferase, a glucuronyltransferase, a heparanase. In some embodiments, the gene encodes a proteoglycan core protein, such as any membrane proteoglycan (e.g., a glypican, a syndecan, or any secreted proteoglycan (e.g. serglycin, perlecan, collagen XVIII, or agrin). In some embodiments the gene is selected from chondroitin sulfate synthase 1 or 3, (ChSy), chondroitin sulfate N-acetylgalactosaminyltransferase 2 (CSGaNAcT2), chondroitin polymerizing factor (ChPF), heparan sulfate 2-O-sulfotransferase (Hs2st), glucuronic acid epimerase (Glce), heparan sulfate N-deacetylase/sulfotransferase-1, 2, 3, or 4 (Ndst1-4), 6-O-sufotransferase 1,2,3 (Hs6st1-3), 3-O-sulfotransferase1, 2, 3, 4, 5, 6 (Hs3st1-6), sulfatase 1 (Sulf1), sulfatase (Sulf2), beta-glucuronidase (Gusb), galactosamine-6 sulfatase (GaNs), alpha-L-iduronidase (idua), sulfamidase (Sgsh), glucosamine N-acetyltransferase (HGSNAT), uronate-2-sulfatase (Ids), alpha-N-acetylglucosaminidase (Naglu), PAPS synthase (PAPSS1, PAPSS2), xylosyltransferase 1 (Xylt1), xylosyltransferase 2 (Xylt2), galactosyltransferase 1 (B4galt1), galactosyltransferase 2 (B4galt2), glucuronyltransferase 1 (Glcat1), exostosin-like glycosyltransferase 3 (Ext13), exostosin glycosyltransferase 1 (Ext1), exostosin glycosyltransferase 2 (Ext2), heparanase (Hpse), glypican 1 (Gpc1), glypican 2 (Gpc2), lypican 3 (Gpc3), glypican 4 (Gpc4), glypican 5 (Gpc5), glypican 6 (Gpc6), syndecan 1 (Sdc1), syndecan 2 (Sdc2), syndecan 3 (Sdc3), syndecan 4 (Sdc4), betaglycan (Ggcan/Tgfbr3), cd44v3 (Cd44v3), neuropillin 1 (Nrp1), CD47 (Cd47), serglycin (Srgn), perlecan (plc), agrin (Agrn), and collagen 18 (Col18a1).

Described herein is the use of a cellular expression system to produce glycosaminoglycans such as heparan sulfate, chondroitin sulfate, dermatan sulfate, keratan sulfate, and hyaluronic acid in various compositions or defined sulfation patterns in a reproducible manner at a scale that will allow investigators to examine the biological properties of the glycosaminoglycan. In some embodiments, the cellular expression system comprises a genetically modified cell from which a chondroitin sulfate composition with a defined pattern of sulfation is derived. In some embodiments, the genetically modified cell is deficient in one or more genes that encode an enzyme that modifies a chondroitin sulfate chain. In some embodiments the genetically modified cell is transgenic for one or more genes that encode an enzyme that modifies a chondroitin sulfate chain. In some embodiments, the gene encodes an enzyme that modifies a chondroitin sulfate chain selected from one or more of a GaNAc transferase, a chondroitin sulfate synthase, a chondroitin sulfate polymerizing factor, a sulfotransferase, or an epimerase. In some embodiments, the gene encodes a proteoglycan core protein, such as any proteoglycan (e.g., an aggrecan, a versican, a neurocan, a brevican, an epiphycan, a procollagen type IX, alpha 2, a DSD-1 proteoglycan, a phosphacan, a thrombomodulin, an endocan, a leprecan, a decorin, a biglycan, a testican 1, a testican 2, a lubricin, a NG2, an invariant chain, or a CD44). In some embodiments the gene is selected from GalNAc transferase 1 (CsGaNAcT1), GaNAc transferase 2 (CSGaNAcT2), Chondroitin sulfate synthase 1 (GcAT and GaNAcT activities) (Chsy1), Chondroitin sulfate synthase 3 (Chsy3), Chondroitin sulfate polymerizing factor (Chpf), Chondroitin sulfate polymerizing factor (Chpf2), Chondroitn 4-O-sulfotransferase 1 (Chst11), Chondroitin 4-O-sulfotransferase 2 (Chst12), Chondroitin 4-O-sulfotransferase 3 (Chst13), Chondroitin 4-sulfate 6-O-sulfotransferase (Chst15), Chondroitin 6 sulfotransferase-1 (Chst3), Chondroitin 6-O-sulfotransferase 2 (Chst7), Dermatan sulfate glucuronyl C5 epimerase 1 (Dse), Dermatan sulfate glucuronyl C5 epimerase-like (Dsel), Dermatan sulfate 4-O-sulfotransferase (Chst14), Aggrecan (CSPG1) (Agc1), Versican/PG-M (CSPG2) (Vcan), Neurocan (CSPG3) (Ncan), Brevican (BCAN) (Bcan), Epiphycan (Dspg3) (Epyc), Procollagen, type IX, alpha 2 (Col9a2), DSD-1-proteoglycan, Phosphacan (Ptprz1), Thrombomodulin (Thbd), Endocan (Esm1), Leprecan (Prolyl 3-hydroxylase 1) (Leprel), Decorin (Dcn), Biglycan (Bgn), Testican 1 (Spock1; osteonectin1) (Spock1), Testican 2 (Spock2, osteonectin2 (Spock2), Testican 2 (Spock3; osteonectn3) (Spock3), Proteoglycan-4 (Lubricin) (Prg4), NG2 (CSPG4) (Cspg4), Invariant chain (Cd74), and CD44 (Cd44).

Disclosed herein are compositions comprising glycosaminoglycans such as heparan sulfate, chondroitin sulfate, dermatan sulfate, keratan sulfate, and hyaluronic acid derived from genetically modified cell lines. The genetically modified cell lines are cell lines comprising a population of cells. In some embodiments, the cells are selected from a 293T cell, a 3T3 cell, a 4T1 cell, a 721 cell, an 9L cell, an A2780 cell, an A2780ADR cell, an A2780cis cell, an A172 cell, an A20 cell, an A253 cell, an A431 cell, an A-549 cell, an ALC cell, a B16 cell, a B35 cell, a BCP-1 cell, a BEAS-2B cell, a bEnd.3 cell, a BHK-21 cell, a BR 293 cell, a BxPC3 cell, a C2C12 cell, a C3H-10T1/2 cell, a C6/36 cell, a C6 cell, a Cal-27 cell, a CGR8 cell, a CHO cell, a COR-L23 cell, a COR-L23/CPR cell, a COR-L23/5010 cell, a COR-L23/R23 cell, a COS-7 cell, a COV-434 cell, a CML T1 cell, a CMT cell, a CT26 cell, a D17 cell, a DH82 cell, a DU145 cell, a DuCaP cell, a E14Tg2a cell, a EL4 cell, a EM2 cell, a EM3 cell, a EMT6/AR1 cell, a EMT6/AR10.0 cell, a FM3 cell, a H1299 cell, a H69 cell, a HB54 cell, a HB55 cell, a HCA2 cell, a HEK-293 cell, a HeLa cell, a Hepalc1c7 cell, a High Five cell, a HL-60 cell, a HMEpC cell, a HT-29 cell, a HUVEC cell, a Jurkat cell, a J558L cell, a JY cell, a K562 cell, a KBM-7 cell, a Ku812 cell, a KCL22 cell, a KG1 cell, a KYO1 cell, a LNCap cell, a Ma-Mel cell, a MC-38 cell, a MCF-7 cell, a MCF-10A cell, a MDA-MB-231 cell, a MDA-MB-157 cell, a MDA-MB-361 cell, a MDCK II cell, a MG63 cell, a MOR/0.2R cell, a MONO-MAC 6 cell, a MRC5 cell, a MTD-1A cell, a MyEnd cell, a NCI-H69/CPR cell, a NCI-H69/LX10 cell, a NCI-H69/LX20 cell, a NCI-H69/LX4 cell, a NIH-3T3 cell, a NALM-1 cell, a NW-145 cell, a OPCN/OPCT cell, a Peer cell, a PNT-1A/PNT 2 cell, a PTK2 cell, a Raji cell, a RBL cell, a RenCa cell, a RIN-5F cell, a RMA/RMAS cell, a S2 cell, a Saos-2 cell, a Sf21 cell, a Sf9 cell, a SiHa cell, a SKBR3 cell, a SKOV-3 cell, a T2 cell, a T-47D cell, a T84 cell, a U373 cell, a U87 cell, a U937 cell, a VCaP cell, a Vero cell, a WM39 cell, a WT-49 cell, a X63 cell, a YAC-1 cell, a YAR cell, or other animal cell described in the ATCC catalog. In some cases, the cell is an animal cell. In some cases the cell is a mammalian cell. In some cases, the cell is a mouse cell, a rat cell, a non-human primate cell, or a human cell.

The genetically modified cell lines are created by methods including but not limited to RNAi; CRISPR/Cas; transgenic cells; cells from transgenic animals; cells from knockout animals; transfection with plasmid; or infection with retrovirus, adenovirus, adeno-associated virus or lentivirus.

In some cases the genetically modified cell lines are genetically deficient in one or more genes, or one or more target genes. Cell lines that are genetically deficient are made by multiple techniques known by those of skill in the art. In some cases the cells are transformed or transfected with a plasmid or virus that expresses an RNAi or shRNA that reduces or eliminates expression of the targeted gene. In some cases the cells are transfected with a double stranded siRNA that reduces or eliminates expression of the targeted gene. In some cases, the genetically modified cell line is created when the target gene is eliminated from the genome of the cell line using the CRISPR/Cas system. In some cases, the cell line is derived from a genetically modified animal that is deficient for the targeted gene or a knockout animal.

In some cases, the genetically modified cell lines are transgenic for one or more genes, or one or more target genes. Transgenic cell lines are made by multiple techniques known by those of skill in the art. In some cases, the cells are transformed or transfected with a plasmid or virus that expresses the gene. In some cases, the cells are infected with a virus, such as a retrovirus, lentivirus, adenovirus, adeno-associated virus, or other virus that infects animal cell, that expresses the target gene. In some cases, the transgene replaces the endogenous gene in the cell line creating a "knock-in" cell line. In some cases, CRISPR/Cas technology is used to create a "knock-in" cell line. In some cases, the transgenic cells are derived from an animal that is transgenic for the target gene.

Also described herein are research compositions used in biomedical and pharmaceutical research. In some cases, research compositions include but are not limited to extracellular matrix, microarrays, libraries of structures in 96-well plates, ligand-binding assays, ligand binding competition assays, intro and in vivo biological experiments. In some cases, extracellular matrix compositions are used for culture of cells.

Methods of Producing Glycosaminoglycan Compositions

Disclosed herein are glycosaminoglycans such as heparan sulfate, chondroitin sulfate, dermatan sulfate, keratan sulfate, and hyaluronic acid compositions comprising defined patterns of modification derived from genetically modified cell lines described herein. Methods of purification of glycosaminoglycans such as heparan sulfate, chondroitin sulfate, dermatan sulfate, keratan sulfate, and hyaluronic acid compositions from cultured cells are known by those of skill in the art. In some embodiments, the compositions are purified from the cell culture media. In some embodiments, the compositions are purified from lysed cells. In some embodiments, the compositions are purified using a chromatography column. In some embodiments, the compositions are purified using an ion exchange column such as an anion exchange column. In some embodiments, the compositions are purified using an affinity column. In some embodiments, the compositions are purified using a size exclusion column. In some embodiments, the compositions are purified from contaminating proteins and/or nucleic acids using enzymes such as a protease and/or a nuclease or enzymes that digest DS, KS, CS, HS or hyaluronic acid (HA). In some embodiments, the compositions are purified from contaminating salt using a size exclusion column. Cell lines can be grown under standard cell culture conditions with or without serum (preferably without). To increase production, different growth medias and additives can be used. To increase production, the cells can be grown in bioreactors of which there are different sizes and a number of different types including but not limited to vats, hollow fibers, and plastic disposable. Production in bioreactors can be increased by using different growth medias and additives as well as by adjusting growth condition parameters such as oxygen levels and pH. Purification methods for small and large scale production are similar but increased for larger scale with larger reagent volumes and/or column resin volumes.

In some embodiments, the processes described herein comprise further treatment steps to purify the glycosaminoglycans, such as heparan sulfate, chondroitin sulfate, dermatan sulfate, keratan sulfate, and hyaluronic acid compositions. For example, in some embodiments, the glycosaminoglycan compositions are purified from a sample that is homogenized. In specific embodiments homogenization is achieved in any suitable manner including, by way of non-limiting example, with a basic solution (e.g., 0.1 N NaOH), sonication, tissue grinding, or other chemical agents).

In some embodiments, glycosaminoglycans such as heparan sulfate, chondroitin sulfate, dermatan sulfate, keratan sulfate, and hyaluronic acid compositions, described herein are purified using any suitable purification technique. In certain embodiments, purification techniques include electrophoresis, chromatography, column chromatography, gas chromatography, high performance liquid chromatography, thin layer chromatography, ion exchange chromatography, gel chromatography, molecular sieve chromatography, affinity chromatography, exclusion, filtration, precipitation, osmosis, recrystallization, fluorous phase purification, distillation, extraction, chromatofocusing, or the like.

In another non-limiting example, the cells or conditioned media comprising the heparin and/or heparan sulfate compositions are extracted using chilled guanidine HCl/Zwittergent extraction buffer with 10 mM EDTA, protease inhibitors (10 mM NEM, 1 mM PMSF, 1 µg/ml pepstatin A, and 0.5 µg/ml leupeptin). Extracted samples are centrifuged to remove insoluble residue. The pellet is optionally re-extracted and centrifuged. Heparin and/or heparan sulfate is purified from the extract by anion-exchange chromatography on a DEAE-Sephacel column in a bind and elute procedure. Eluted heparin and/or heparan sulfate compositions are desalted using a sephadex G-25 gel filtration and subsequently lyophilized and rehydrated in a physiologically acceptable buffer. Additional details and alternative purification procedures are found in Esko, J. Special Considerations for Proteoglycans and Glycosaminoglycans and Their Purification. 2000. Curr. Protoc. Mol. Biol. 22:17.2.1-17.2.9, which is hereby incorporated by reference in its entirety.

In some embodiments, heparin and/or heparan sulfate compositions, are naturally found attached to a core protein (together forming a proteoglycan). In certain embodiments, a purification process used herein is a process that includes a protocol that cleaves a core protein from a heparin and/or heparan sulfate (e.g., treatment with a protease, such as a non-specific protease (e.g., Pronase) to cleave the proteins; or by chemical means (beta-elimination chemistry)). In other embodiments, a purification process described herein does not include a protocol that cleaves a heparin and/or heparan sulfate from a core protein. In some embodiments, heparin and/or heparan sulfate compositions are further purified using enzymes including but not limited to DNase, RNase, chondroitinase ABC, hyaluronidase, and combinations thereof.

Pharmaceutical Compositions

Disclosed herein are pharmaceutical compositions comprising one or more glycosaminoglycans such as heparan sulfate, chondroitin sulfate, keratan sulfate, and hyaluronic acid compositions with a defined pattern of modification derived from genetically modified cell lines as described herein and one or more pharmaceutically acceptable carriers or excipients. In certain embodiments, pharmaceutical compositions are formulated in a conventional manner using one or more physiologically acceptable carriers including, e.g., excipients and auxiliaries which facilitate processing of the active compounds into preparations which are suitable for pharmaceutical use. In certain embodiments, proper formulation is dependent upon the route of administration chosen. A summary of pharmaceutical compositions described herein is found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

A pharmaceutical composition, as used herein, refers to a mixture of one or more glycosaminoglycans such as heparan sulfate, chondroitin sulfate, keratan sulfate, and hyaluronic acid compositions with defined patterns of modification described herein, with other chemical components, such as carriers, stabilizers, diluents, dispersing agents, suspending agents, thickening agents, and/or excipients. In certain instances, the pharmaceutical composition facilitates administration of the glycosaminoglycans such as heparan sulfate, chondroitin sulfate, keratan sulfate, and hyaluronic acid compositions with a defined pattern of modification to an individual or cell. In certain embodiments of practicing the methods of treatment or use provided herein, therapeutically effective amounts of glycosaminoglycans such as heparan sulfate, chondroitin sulfate, keratan sulfate, and hyaluronic acid compositions with a defined pattern of modification described herein are administered in a pharmaceutical composition to an individual having a disease, disorder, or condition to be treated. In specific embodiments, the individual is a human. As discussed herein, the glycosaminoglycans such as heparan sulfate, chondroitin sulfate, keratan sulfate, and hyaluronic acid compositions with a defined pattern of modification described herein are either utilized singly or in combination with one or more additional therapeutic agents.

In certain embodiments, one or more glycosaminoglycans such as heparan sulfate, chondroitin sulfate, keratan sulfate, and hyaluronic acid compositions with defined patterns of modification described herein are combined with one or more other active pharmaceutical ingredients. In some cases, one or more glycosaminoglycans such as heparan sulfate, chondroitin sulfate, keratan sulfate, and hyaluronic acid compositions with defined patterns of modification described herein act as an excipient in the pharmaceutical composition with the other active pharmaceutical ingredients. In some cases, one or more glycosaminoglycans such as heparan sulfate, chondroitin sulfate, keratan sulfate, and hyaluronic acid compositions with defined patterns of modification described herein act as an adjuvant in the pharmaceutical composition. In some cases, one or more glycosaminoglycans such as heparan sulfate, chondroitin sulfate, keratan sulfate, and hyaluronic acid compositions with defined patterns of modification described herein enhance the activity of the other components of the pharmaceutical composition. In some embodiments, the other component is a protein, a nucleic acid, a lipid, or a small molecule.

In certain embodiments, the pharmaceutical formulations described herein are administered to an individual in any manner, including one or more of multiple administration routes, such as, by way of non-limiting example, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound described herein are optionally manufactured in a conventional manner, such as, by way of example only, by means of conventional mixing, dissolving, granulating, dragee-making, levigating, emulsifying, encapsulating, entrapping or compression processes.

In certain embodiments, a pharmaceutical compositions described herein includes one or more glycosaminoglycans such as heparan sulfate, chondroitin sulfate, keratan sulfate, and hyaluronic acid compositions with a defined pattern of modification described herein, as an active ingredient in free-acid or free-base form, or in a pharmaceutically acceptable salt form. In some embodiments, the compounds described herein are utilized in a crystalline or lyophilized form. In certain embodiments, an active metabolite or prodrug of a compound described herein is utilized. In some situations, a compound described herein exists as different stereoisomers. All stereoisomers are included within the scope of the compounds presented herein. In certain embodiments, a compound described herein exists in an unsolvated or solvated form, wherein solvated forms comprise any pharmaceutically acceptable solvent, e.g., water, ethanol, and the like. The solvated forms of the glycosaminoglycans such as heparan sulfate, chondroitin sulfate, keratan sulfate, and hyaluronic acid compositions with a defined pattern of modification presented herein are also considered to be disclosed herein.

A "carrier" includes, in some embodiments, a pharmaceutically acceptable excipient and is selected on the basis of compatibility with glycosaminoglycans such as heparan sulfate, chondroitin sulfate, keratan sulfate, and hyaluronic acid compositions with a defined pattern of modification disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Moreover, in certain embodiments, the pharmaceutical compositions described herein are formulated as a dosage form. As such, in some embodiments, provided herein is a dosage form comprising glycosaminoglycans such as heparan sulfate, chondroitin sulfate, keratan sulfate, and hyaluronic acid compositions with a defined pattern of modification described herein, suitable for administration to an individual. In certain embodiments, suitable dosage forms include, by way of non-limiting example, aqueous oral dispersions, liquids, gels, syrups, elixirs, slurries, suspensions, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

The pharmaceutical solid dosage forms described herein optionally include an additional therapeutic compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In some aspects, using coating procedures, such as those described in Remington's Pharmaceutical Sciences, 20th Edition (2000), a film coating is provided around the formulation of the glycosaminoglycans such as heparan sulfate, chondroitin sulfate, keratan sulfate, and hyaluronic acid compositions with a defined pattern of modification. In one embodiment, a glycosaminoglycans such as heparan sulfate, chondroitin sulfate, keratan sulfate, and hyaluronic acid compositions with a defined pattern of modification described herein is in the form of a particle and some or all of the particles of the compound are coated. In certain embodiments, some or all of the particles of a glycosaminoglycans such as heparan sulfate, chondroitin sulfate, keratan sulfate, and hyaluronic acid compositions with a defined pattern of modification described herein are microencapsulated. In some embodiment, the particles of the glycosaminoglycans such as heparan sulfate, chondroitin sulfate, keratan sulfate, and hyaluronic acid compositions with a defined pattern of modification described herein are not microencapsulated and are uncoated.

In certain embodiments, the pharmaceutical composition described herein is in unit dosage forms suitable for single administration of precise dosages. In unit dosage form, the formulation is divided into unit doses containing appropriate quantities of one or more therapeutic compound. In some embodiments, the unit dosage is in the form of a package containing discrete quantities of the formulation. Non-limiting examples are packaged tablets or capsules, and powders in vials or ampoules. Aqueous suspension compositions are optionally packaged in single-dose non-reclosable containers. In some embodiments, multiple-dose re-closeable containers are used. In certain instances, multiple dose containers comprise a preservative in the composition. By way of example only, formulations for parenteral injection are presented in unit dosage form, which include, but are not limited to ampoules, or in multi dose containers, with an added preservative.

Methods of Treatment

In addition to applications in research, heparan sulfate and other glycosaminoglycans and proteoglycans have potential applications as functional ingredients in pharmaceutical or nutraceutical preparations across a range of medical treatments including thrombosis, inflammation, cancer, microbial infections, neurodegenerative disorders and wound healing among others. Pharmaceutical heparin is a widely used, commercially prepared fraction therapeutically used for its anticoagulant properties in treatments and for prevention of thrombotic disorders. Heparin has a number of negative attributes however, including a propensity to cause thrombocytopenia and hemorrhagic bleeding. This may be reduced by engineering cells to produce a heparan sulfate/heparin composition that retains significant antithrombin binding but with reduced platelet factor 4 (PF4) binding. Heparin also has a natural high structural diversity, which can result in significant oscillations in the therapeutic dosage window. A defined heparan sulfate composition produced by genetically modified cell lines would provide a clear advantage and improvement over the currently available treatments.

A number of novel heparan sulfate/heparin structures have been prepared from marine invertebrate organisms. Initial characterizations have identified unique anticoagulant properties that appear to be associated with significantly reduced bleeding effects and other advantages compared to heparin. One unique invertebrate structure that resembles heparan sulfate and heparin termed acharan sulfate (AS) has been isolated from the pulmonate gastropod (snail) *A. fulica*. Despite a lower sulfation content and simple structure, AS presents a multitude of medicinal properties including bFGF mitogenicity, anticoagulation, anti-angiogenesis in models of inflammation, immunostimulant, hypoglycemic, hypolipidemic, tumor suppression, antibacterial, and an aid to wound healing, among others. Some of these novel compositions may entail new enzymes and other factors, however, once understood, cells may be engineered to produce adequate quantities of these structures to take advantage of the medical applications on a commercial basis.

Therefore, disclosed herein are methods of treating disease in subjects in need thereof by administering an effective amount of one or more glycosaminoglycans such as heparan sulfate, chondroitin sulfate, keratan sulfate, and hyaluronic acid compositions with defined modification patterns described herein. In some embodiments, the disease comprises one or more of thrombosis, inflammation, cancer, microbial infections, neurodegenerative disorders, wound healing, and other diseases with known association with glycosaminoglycans and/or heparan sulfate, that would be known by one of skill in the art.

In some embodiments, the compositions or pharmaceutical compositions disclosed herein are administered to the subject by any route known in the art, found to be effective in treating thrombosis, inflammation, cancer, microbial infections, neurodegenerative disorders and wound healing among others. In some embodiments, the compositions or pharmaceutical compositions disclosed herein are administered orally, rectally, sublingually, sublabially, buccally, epidurally, entracerebrally, intracerebroventricalarly, topically, transdermally, nasally, intraarterially, intraarticularly, intracardiacally, intradermally, subcutaneously, intralesionally, intramuscular, intraocularly, intraosseously, intraperitoneally, intrathecally, intravenously, transmucosally, or any other route of administration known by one of skill in the art.

Treatment of Thrombosis

In some embodiments, there is provided a method of treating thrombosis in a subject in need thereof comprising administering to the subject an effective amount of one or more glycosaminoglycans such as heparan sulfate, chondroitin sulfate, keratan sulfate, and hyaluronic acid compositions with defined modification patterns described herein. In some embodiments, the thrombosis comprises, venous thrombosis, deep vein thrombosis, portal vein thrombosis, renal vein thrombosis, jugular vein thrombosis, Budd-Chiari syndrome, Paget-Schroetter disease, Cerebral venous sinus thrombosis, Cavernous sinus thrombosis, arterial thrombosis, stroke, myocardial infarction, Hepatic artery thrombosis, acute coronary syndrome atrial fibrillation, or pulmonary embolism. In some embodiments, treatment of the thrombosis reduces swelling, pain, tenderness, skin discoloration, shortness of breath, chest pain, rapid heart rate, cough, or other symptom of thrombosis. In some embodiments, the method prevents or eliminates a blood clot. In some embodiments, the method prevents or eliminates a blood clot without causing heparin-induced thrombocytopenia.

Treatment of Inflammation

In some embodiments, there is provided a method of treating inflammation in a subject in need thereof comprising administering to the subject an effective amount of one or more glycosaminoglycans such as heparan sulfate, chondroitin sulfate, keratan sulfate, and hyaluronic acid compositions with defined modification patterns described herein. In some embodiments, the inflammation comprises rheumatoid arthritis, juvenile rheumatoid arthritis, osteoarthritis, psoriatic arthritis, multiple sclerosis (MS), encephalomyelitis, myasthenia gravis, systemic lupus erythematosus (SLE), asthma, allergic asthma, autoimmune thyroiditis, atopic dermatitis, eczematous dermatitis, psoriasis, Sjögren's Syndrome, Crohn's disease, aphthous ulcer, iritis, conjunctivitis, keratoconjunctivitis, ulcerative colitis (UC), inflammatory bowel disease (IBD), cutaneous lupus erythematosus, scleroderma, vaginitis, proctitis, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, interstitial lung fibrosis, Hashimoto's thyroiditis, autoimmune polyglandular syndrome, insulin-dependent diabetes mellitus (IDDM, type I diabetes), insulin-resistant diabetes mellitus (type 2 diabetes), immune-mediated infertility, autoimmune Addison's disease, pemphigus vulgaris, pemphigus *foliaceus*, dermatitis herpetiformis, autoimmune alopecia, vitiligo, autoimmune hemolytic anemia, autoimmune thrombocytopenic purpura, pernicious anemia, Guillain-Barre syndrome, stiff-man syndrome, acute rheumatic fever, sympathetic ophthalmia, Goodpasture's syndrome, systemic necrotizing vasculitis, antiphospholipid syndrome or an allergy, Behcet's disease, X-linked lymphoproliferative syndrome (SH2D1A/SAP deficiency), hyper IgE syndrome or Graft vs. Host Disease (GVHD). In some embodiments, treatment of the inflammation reduces pain, redness, swelling, loss of joint function, fever, chills, fatigue, headache, loss of appetite, muscle stiffness, or other symptom associated with inflammation or inflammatory disease.

Treatment of Cancer

In some embodiments, there is provided a method of treating cancer in a subject in need thereof comprising administering to the subject an effective amount of one or more glycosaminoglycans such as heparan sulfate, chondroitin sulfate, keratan sulfate, and hyaluronic acid compositions with defined modification patterns described herein. In some embodiments, the cancer comprises Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, or other type of cancer. In some embodiments, the cancer comprises a metastasis of one or more of the above cancers.

Efficacy in treating cancer in particular may be measured by any suitable metric. In some embodiments, therapeutic efficacy is measured based on an effect of treating a proliferative disorder, such as cancer. In general, therapeutic efficacy of the methods and compositions of the invention, with regard to the treatment of a proliferative disorder (e.g. cancer, whether benign or malignant), may be measured by the degree to which the methods and compositions promote inhibition of tumor cell proliferation, the inhibition of tumor vascularization, the eradication of tumor cells, and/or a reduction in the size of at least one tumor such that a human is treated for the proliferative disorder. Several parameters to be considered in the determination of therapeutic efficacy are discussed herein. The proper combination of parameters for a particular situation can be established by the clinician. The progress of the inventive method in treating cancer (e.g., reducing tumor size or eradicating cancerous cells) can be ascertained using any suitable method, such as those methods currently used in the clinic to track tumor size and cancer progress. In some embodiments, the primary efficacy parameter used to evaluate the treatment of cancer preferably is a reduction in the size of a tumor. Tumor size can be determined using any suitable technique, such as measurement of dimensions, or estimation of tumor volume using available computer software, such as FreeFlight software developed at Wake Forest University that enables accurate estimation of tumor volume. Tumor size can be determined by tumor visualization using, for example, CT, ultrasound, SPECT, spiral CT, MRI, photographs, and the like. In embodiments where a tumor is surgically resected after completion of the therapeutic period, the presence of tumor tissue and tumor size can be determined by gross analysis of the tissue to be resected, and/or by pathological analysis of the resected tissue.

Desirably, the growth of a tumor is stabilized (i.e., one or more tumors do not increase more than 1%, 5%, 10%, 15%, or 20% in size, and/or do not metastasize) as a result of treatment. In some embodiments, a tumor is stabilized for at least about 1, 2, 3, 4, 5, 6, 7, 8, 9, 10, 11, 12, or more weeks.

In some embodiments, a tumor is stabilized for at least about 1, 2, 3, 4, 5, 6, 7, 8, 9, 10, 11, 12, or more months. In some embodiments, a tumor is stabilized for at least about 1, 2, 3, 4, 5, 6, 7, 8, 9, 10, or more years. In some embodiments, the size of a tumor is reduced at least about 5% (e.g., at least about 10%, 15%, 20%, or 25%). In some embodiments, tumor size is reduced at least about 30% (e.g., at least about 35%, 40%, 45%, 50%, 55%, 60%, or 65%). In some embodiments, tumor size is reduced at least about 70% (e.g., at least about 75%, 80%, 85%, 90%, or 95%). In some embodiments, the tumor is completely eliminated, or reduced below a level of detection. In some embodiments, a subject remains tumor free (e.g. in remission) for at least about 1, 2, 3, 4, 5, 6, 7, 8, 9, 10, 11, 12, or more weeks following treatment. In some embodiments, a subject remains tumor free for at least about 1, 2, 3, 4, 5, 6, 7, 8, 9, 10, 11, 12, or more months following treatment. In some embodiments, a subject remains tumor free for at least about 1, 2, 3, 4, 5, 6, 7, 8, 9, 10, or more years after treatment.

When a tumor is subject to surgical resection following completion of the therapeutic period, the efficacy of the inventive method in reducing tumor size can be determined by measuring the percentage of resected tissue that is necrotic (i.e., dead). In some embodiments, a treatment is therapeutically effective if the necrosis percentage of the resected tissue is greater than about 20% (e.g., at least about 30%, 40%, 50%, 60%, 70%, 80%, 90%, or 100%), more preferably about 90% or greater (e.g., about 90%, 95%, or 100%). Most preferably, the necrosis percentage of the resected tissue is about 100%, that is, no tumor tissue is present or detectable.

A number of secondary parameters can be employed to determine the efficacy of the inventive method. Examples of secondary parameters include, but are not limited to, detection of new tumors, detection of tumor antigens or markers (e.g., CEA, PSA, or CA-125), biopsy, surgical downstaging (i.e., conversion of the surgical stage of a tumor from unresectable to resectable), PET scans, survival, disease progression-free survival, time to disease progression, quality of life assessments such as the Clinical Benefit Response Assessment, and the like, all of which can point to the overall progression (or regression) of cancer in a human. Biopsy is particularly useful in detecting the eradication of cancerous cells within a tissue. Radioimmunodetection (RAID) is used to locate and stage tumors using serum levels of markers (antigens) produced by and/or associated with tumors ("tumor markers" or "tumor-associated antigens"), and can be useful as a pre-treatment diagnostic predicate, a post-treatment diagnostic indicator of recurrence, and a post-treatment indicator of therapeutic efficacy. Examples of tumor markers or tumor-associated antigens that can be evaluated as indicators of therapeutic efficacy include, but are not limited to, carcinembryonic antigen (CEA) prostate-specific antigen (PSA), CA-125, CA19-9, ganglioside molecules (e.g., GM2, GD2, and GD3), MART-1, heat shock proteins (e.g., gp96), sialyl Tn (STn), tyrosinase, MUC-1, HER-2/neu, c-erb-B2, KSA, PSMA, p53, RAS, EGF-R, VEGF, MAGE, and gp100. Other tumor-associated antigens are known in the art. RAID technology in combination with endoscopic detection systems also efficiently distinguishes small tumors from surrounding tissue.

In some embodiments, the treatment of cancer in a human patient is evidenced by one or more of the following results: (a) the complete disappearance of a tumor (i.e., a complete response), (b) about a 25% to about a 50% reduction in the size of a tumor for at least four weeks after completion of the therapeutic period as compared to the size of the tumor before treatment, (c) at least about a 50% reduction in the size of a tumor for at least four weeks after completion of the therapeutic period as compared to the size of the tumor before the therapeutic period, and (d) at least a 2% decrease (e.g., about a 5%, 10%, 20%, 30%, 40%, 50%, 60%, 70%, 80% or 90% decrease) in a specific tumor-associated antigen level at about 4-12 weeks after completion of the therapeutic period as compared to the tumor-associated antigen level before the therapeutic period. While at least a 2% decrease in a tumor-associated antigen level is preferred, any decrease in the tumor-associated antigen level is evidence of treatment of a cancer in a patient. For example, with respect to unresectable, locally advanced pancreatic cancer, treatment can be evidenced by at least a 10% decrease in the CA19-9 tumor-associated antigen level at 4-12 weeks after completion of the therapeutic period as compared to the CA19-9 level before the therapeutic period. Similarly, with respect to locally advanced rectal cancer, treatment can be evidenced by at least a 10% decrease in the CEA tumor-associated antigen level at 4-12 weeks after completion of the therapeutic period as compared to the CEA level before the therapeutic period.

With respect to quality of life assessments, such as the Clinical Benefit Response Criteria, the therapeutic benefit of the treatment in accordance with the invention can be evidenced in terms of pain intensity, analgesic consumption, and/or the Karnofsky Performance Scale score. The Karnofsky Performance Scale allows patients to be classified according to their functional impairment. The Karnofsky Performance Scale is scored from 0-100. In general, a lower Karnofsky score is predictive of a poor prognosis for survival. Thus, the treatment of cancer in a human patient alternatively, or in addition, is evidenced by (a) at least a 50% decrease (e.g., at least a 60%, 70%, 80%, 90%, or 100% decrease) in pain intensity reported by a patient, such as for any consecutive four week period in the 12 weeks after completion of treatment, as compared to the pain intensity reported by the patient before treatment, (b) at least a 50% decrease (e.g., at least a 60%, 70%, 80%, 90%, or 100% decrease) in analgesic consumption reported by a patient, such as for any consecutive four week period in the 12 weeks after completion of treatment as compared to the analgesic consumption reported by the patient before treatment, and/or (c) at least a 20 point increase (e.g., at least a 30 point, 50 point, 70 point, or 90 point increase) in the Karnofsky Performance Scale score reported by a patient, such as for any consecutive four week period in the 12 weeks after completion of the therapeutic period as compared to the Karnofsky Performance Scale score reported by the patient before the therapeutic period.

The treatment of a proliferative disorder (e.g. cancer, whether benign or malignant) in a human patient desirably is evidenced by one or more (in any combination) of the foregoing results, although alternative or additional results of the referenced tests and/or other tests can evidence treatment efficacy.

In some embodiments, tumor size is reduced preferably without significant adverse events in the subject. Adverse events are categorized or "graded" by the Cancer Therapy Evaluation Program (CTEP) of the National Cancer Institute (NCI), with Grade 0 representing minimal adverse side effects and Grade 4 representing the most severe adverse events. The NCI toxicity scale (published April 1999) and Common Toxicity Criteria Manual (updated August 1999) is available through the NCI, e.g., or in the Investigator's Handbook for participants in clinical trials of investigational agents sponsored by the Division of Cancer Treatment and Diagnosis, NCI (updated March 1998). Desirably, methods described herein are associated with minimal adverse events, e.g. Grade 0, Grade 1, or Grade 2 adverse events, as graded by the CTEP/NCI. However, reduction of tumor size, although preferred, is not required in that the actual size of a tumor may not shrink despite the eradication (such as in necrosis) of tumor cells. Eradication of cancerous cells is sufficient to realize a therapeutic effect. Likewise, any reduction in tumor size is sufficient to realize a therapeutic effect.

Detection, monitoring, and rating of various cancers in a human are further described in Cancer Facts and Figures 2001, American Cancer Society, New York, N.Y. Accordingly, a clinician can use standard tests to determine the efficacy of the various embodiments of the inventive method in treating cancer. However, in addition to tumor size and spread, the clinician also may consider quality of life and survival of the patient in evaluating efficacy of treatment.

Treatment of Microbial Infection

In some embodiments, there is provided a method of treating a microbial infection in a subject in need thereof comprising administering to the subject an effective amount of one or more glycosaminoglycan and/or heparan sulfate compositions with defined modification patterns described herein. In some embodiments the microbial infection comprises a bacterial infection. In some embodiments, the bacterial infection is a *Bacillus* such as a *Bacillus anthracis* or a *Bacillus cereus*; a *Bartonella* such as a *Bartonella henselae* or a *Bartonella quintana*; a *Bordetella* such as a *Bordetella pertussis*; a *Borrelia* such as a *Borrelia burgdorferi*, a *Borrelia garinii*, a *Borrelia afzelii*, a *Borrelia recurrentis*; a *Brucella* such as a *Brucella abortus*, a *Brucella canis*, a *Brucella melitensis* or a *Brucella suis*; a *Campylobacter* such as a *Campylobacter jejuni*; a *Chlamydia* or *Chlamydophila* such as *Chlamydia pneumoniae, Chlamydia trachomatis, Chlamydophila psittaci*; a *Clostridium* such as a *Clostridium botulinum*, a *Clostridium difficile*, a *Clostridium perfringens*, a *Clostridium tetani*; a *Corynebacterium* such as a *Corynebacterium diphtheriae*; an *Enterococcus* such as a *Enterococcus faecalis* or a *Enterococcus faecium*; a *Escherichia* such as a *Escherichia coli*; a *Francisella* such as a *Francisella tularensis*; a *Haemophilus* such as a *Haemophilus influenzae*; a *Helicobacter* such as a *Helicobacter pylori*; a *Legionella* such as a *Legionella pneumophila*; a *Leptospira* such as a *Leptospira interrogans*, a *Leptospira santarosai*, a *Leptospira weilii* or a *Leptospira noguchii*; a *Listeria* such as a *Listeria monocytogenes*; a *Mycobacterium* such as a *Mycobacterium leprae*, a *Mycobacterium tuberculosis* or a *Mycobacterium ulcerans*; a *Mycoplasma* such as a *Mycoplasma pneumoniae*; a *Neisseria* such as a *Neisseria gonorrhoeae* or a *Neisseria meningitidis*; a *Pseudomonas* such as a *Pseudomonas aeruginosa*; a *Rickettsia* such as a *Rickettsia rickettsii*; a *Salmonella* such as a *Salmonella typhi* or a *Salmonella typhimurium*; a *Shigella* such as a *Shigella sonnei*; a *Staphylococcus* such as a *Staphylococcus aureus*, a *Staphylococcus epidermidis*, a *Staphylococcus saprophyticus*; a *Streptococcus* such as a *Streptococcus agalactiae*, a *Streptococcus pneumoniae*, a *Streptococcus pyogenes*; a *Treponema* such as a *Treponema pallidum*; a *Vibrio* such as a *Vibrio cholerae*; a *Yersinia* such as a *Yersinia pestis*, a *Yersinia enterocolitica* or a *Yersinia pseudotuberculosis*. In some embodiments, the microbial infection comprises a viral infection. In some embodiments, the viral infection comprises a Adenoviridae such as, an Adenovirus; a Herpesviridae such as a Herpes simplex, type 1, a Herpes simplex, type 2, a Varicella-zoster virus, an Epstein-barr virus, a Human cytomegalovirus, a Human herpesvirus, type 8; a Papillomaviridae such as a Human papillomavirus; a Polyomaviridae such as a BK virus or a JC virus; a Poxviridae such as a Smallpox; a Hepadnaviridae such as a Hepatitis B virus; a Parvoviridae such as a Human bocavirus or a Parvovirus; a Astroviridae such as a Human astrovirus; a Caliciviridae such as a Norwalk virus; a Picornaviridae such as a coxsackievirus, a hepatitis A virus, a poliovirus, a rhinovirus; a Coronaviridae such as a Severe acute respiratory syndrome virus; a Flaviviridae such as a Hepatitis C virus, a yellow fever virus, a dengue virus, a West Nile virus; a Togaviridae such as a Rubella virus; a Hepeviridae such as a Hepatitis E virus; a Retroviridae such as a Human immunodeficiency virus (HIV); a Orthomyxoviridae such as an Influenza virus; a Arenaviridae such as a Guanarito virus, a Junin virus, a Lassa virus, a Machupo virus, a Sabia virus; a Bunyaviridae such as a Crimean-Congo hemorrhagic fever virus; a Filoviridae such as a Ebola virus, a Marburg virus; a Paramyxoviridae such as a Measles virus, a Mumps virus, a Parainfluenza virus, a Respiratory syncytial virus, a Human metapneumovirus, a Hendra virus, a Nipah virus; a Rhabdoviridae such as a Rabies virus; a Hepatitis D virus; or a Reoviridae such as a Rotavirus, a Orbivirus, a Coltivirus, a Banna virus infection. In some embodiments, the microbial infection comprises a fungal infection. In some embodiments, the microbial infection comprises a fungal infection. In some embodiments, the fungal infection comprises actinomycosis, allergic bronchopulmonary aspergillosis, aspergilloma, aspergillosis, athlete's foot, basidiobolomycosis, basidiobolus ranarum, black *piedra*, blastomycosis, *Candida krusei*, candidiasis, chronic pulmonary aspergillosis, *chrysosporium*, chytridiomycosis, coccidioidomycosis, conidiobolomycosis, cryptococcosis, *cryptococcus gattii*, deep dermatophytosis, dermatophyte, dermatophytid, dermatophytosis, endothrix, entomopathogenic fungus, epizootic lymphangitis, esophageal candidiasis, exothrix, fungal meningitis, fungemia, *geotrichum, geotrichum candidum*, histoplasmosis, lobomycosis, massospora cicadina, *microsporum gypseum*, muscardine, mycosis, myringomycosis, neozygites remaudierei, neozygites slavi, ochroconis gallopava, ophiocordyceps *arborescens*, ophiocordyceps coenomyia, ophiocordyceps macroacicularis, ophiocordyceps *nutans*, oral candidiasis, paracoccidioidomycosis, pathogenic dimorphic fungi, penicilliosis, *piedra*, piedraia, *pneumocystis* pneumonia, pseudallescheriasis, scedosporiosis, sporotrichosis, tinea, tinea barbae, tinea capitis, tinea corporis, tinea cruris, tinea faciei, tinea incognito, tinea nigra, tinea pedis, tinea *versicolor*, vomocytosis, white nose syndrome, zeaspora, or zygomycosis. In some embodiments, treatment of the microbial infection reduces one or more symptoms such as fever, diarrhea, fatigue, or pain.

Treatment of Genetic Disorders

In some embodiments, there is provided a method of treating a genetic disorder in a subject in need thereof comprising administering to the subject an effective amount of one or more glycosaminoglycan and/or heparan sulfate compositions with defined modification patterns described herein. In some embodiments, the genetic disorder comprises Achondrogenesis type IB; Atelosteogenesis type II; Diastrophic dysplasia; Multiple epiphyseal dysplasia, AR type; Spondyloepimetaphyseal dysplasia, Pakistani type (PAPSS2 type); Hyperandrogenism; Brachyolmia, AR type; Schneckenbecken dysplasia; EDS, progeroid form; Larsen-like syndrome, B3GAT3 type; Hereditary motor and sensory neuropathy, unknown type; Bell palsy; Temtamy pre-axial brachydactyly syndrome; Syndromic recessive pre-axial brachydactyly; Spondyloepiphyseal dysplasia, Omani type; Chondrodysplasia with multiple dislocations; Humerospinal dysostosis; Larsen syndrome, AR type; Desbuquois syndrome; Bipolar disorder; Depressive disorder; Diaphragmatic hernia; Microphthalmia; EDS, Kosho type; EDS, musculocontractural type; EDS, type VIB; ATCS; or other genetic disorder. In some embodiments, the method reduces symptoms of the disorder. In some embodiments, the method completely eliminates symptoms of the disorder. In some embodiments, the method cures the disorder. In some embodiments, the method eliminates the need for alternative therapies for the disorder. In some embodiments, the method delays onset of more severe symptoms of the disorder.

Treatment of Neurodegenerative Disorders

In some embodiments, there is provided a method of treating a neurodegenerative disorder in a subject in need thereof comprising administering to the subject an effective amount of one or more glycosaminoglycan and/or heparan sulfate compositions with defined modification patterns described herein. In some embodiments, the neurodegenerative disorder comprises Alzheimer's disease, Parkinson's disease, Huntington's disease, Amyotrophic lateral sclerosis, Dementia, Transmissible spongiform encephalopathy, Dentatorubropallidoluysian atrophy, Spinal and bulbar muscular atrophy, Spinocerebellar ataxia Type 1, Spinocerebellar ataxia Type 2, Spinocerebellar ataxia Type 3, Spinocerebellar ataxia Type 6, Spinocerebellar ataxia Type 7, or Spinocerebellar ataxia Type 17. In some embodiments, the method reduces symptoms of a neurodegenerative disorder such as memory loss, disorientation, confusion, mood and/or personality disorder, tremor, bradykinesia, muscle rigidity, balance impairment, speech disorder, choria, dystonia, ataxia, swallowing disorder, irritability, sadness, apathy, social withdrawal, insomnia, fatigue, suicidal thoughts, weakness, speech disorder, muscle cramping, impaired coordination, stumbling, unsteady gait, uncontrolled movements, slurred speech, vocal changes, or headache. In some embodiments, the method delays onset of more severe symptoms. In some embodiments, the delay is 1, 2, 3, 4, 5, 6 or more weeks, 1, 2, 3, 4, 5, 6, 7, 8, 9, 10, 11, 12, or more months, 1, 2, 3, 4, 5, 6, 7, 8, 9, 10, 11, 12, 13, 14, 15, 20, 25, 30, or more years.

Treatment of Wounds

In some embodiments, there is provided a method of treating a wound in a subject in need thereof comprising administering to the subject an effective amount of one or more glycosaminoglycan and/or heparan sulfate compositions with defined modification patterns described herein. In some embodiments, the wound comprises an incision, a laceration, an abrasion, an avulsion, a puncture wound, a penetration wound, a gunshot wound, a hematoma, or a crush injury. In some embodiments, the method reduces symptoms or complications related to a wound, such as drainage, pus, fever, or lymph node swelling. In some embodiments, the method speeds the healing time of a wound. In some embodiments, the method treats diabetic wounds. In some embodiments, the method treats a nerve injury. In some embodiments, the method treats a spinal cord injury.

Definitions

The term "glycosaminoglycan" or "GAG" as used herein refers to long unbranched polysaccharides consisting of a repeating disaccharide unit. The repeating unit (except for keratan) consists of an amino sugar (N-acetylglucosamine or N-acetylgalactosamine) along with a uronic sugar (glucuronic acid or iduronic acid) or galactose.

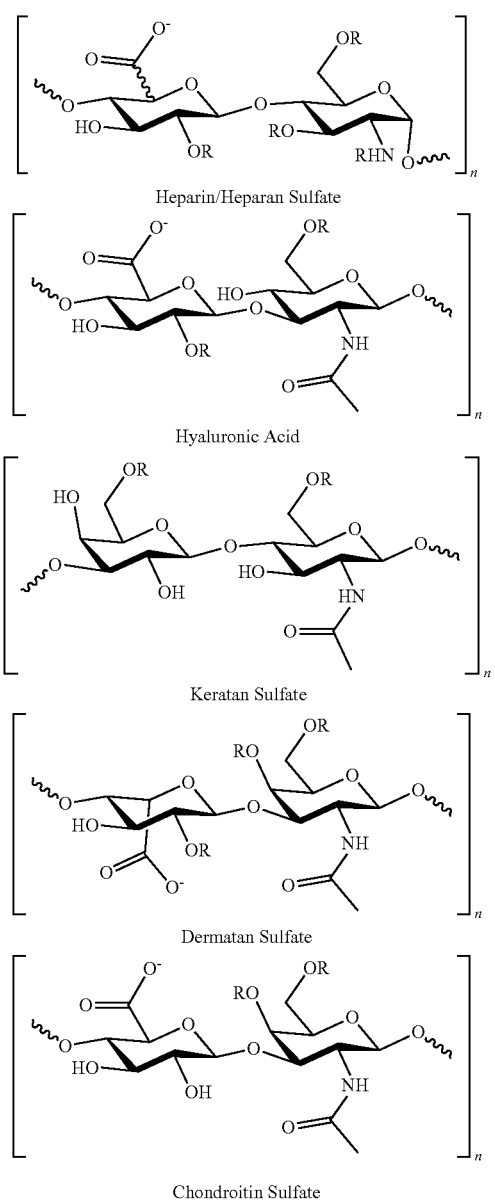

Heparin/Heparan Sulfate

Hyaluronic Acid

Keratan Sulfate

Dermatan Sulfate

Chondroitin Sulfate

The term "proteoglycan" as used herein refers to proteins that are heavily glycosylated. The basic proteoglycan unit comprises a core protein with one or more covalently attached glycosaminoglycan or GAG chains.

The term "core protein" as used herein refers to a protein component of a proteoglycan.

The term "heparan sulfate" as used herein refers to a linear polysaccharide with the structure. Heparan sulfate is made of repeating disaccharide units. The repeating disaccharide units can comprise one or more of β-D-glucuronic acid (GlcA), 2-deoxy-2-acetamido-α-D-glucopyranosyl (GlcNAc), α-L-iduronic acid (IdoA), 2-O-sulfo-α-L-iduronic acid (IdoA2S), 2-deoxy-2-sulfamido-α-D-glucopyranosyl (GlcNS), 2-deoxy-2-sulfamido-α-D-glucopyranosyl-6-O-sulfate (GcNS6S) or 2-deoxy-2-sulfamido-α-D-glucopyranosyl-3,6-O-disulfate (GlcNS3S6S) or 2-deoxy-2-sulfamido-α-D-glucopyranosyl-3-O-sulfate (GcNS3 S).

The term "chondroitin sulfate" as used herein refers to a linear polysaccharide with the structure. Chondroitin sulfate is made of repeating dissacharide units. The repeating dissacharide units can comprise one or more of N-acetylgalactosamine (GalNAc), N-acetylgalactosamine-4-sulfate (GalNAc4S), N-acetylgalactosamine-6-sulfate (GalNAc6S), N-acetylgalactosamine-4,6-disulfate (GalNAc4S6S) and β-D-glucuronic acid (GcA), D-glucuronic acid-2-sulfate (GlcA2S), D-glucuronic acid-3-sulfate (GlcA3S), L-iduronic acid (IdoA), L-iduronic acid-2-sulfate (IdoA2S).

The terms "sulfation pattern", "defined pattern of sulfation", and "defined modification pattern" as used herein refer to enzymatic modifications made to the glycosaminoglycan including but not limited to include sulfation, deacetylation, and epimerization. This also includes glycosaminoglycan compositions having a defined dissacharide composition.

The term "genetically modified cell line" as used herein refers to a cell line with specific modifications made to the genome of the cell line. In some embodiments, the cell line is mammalian. In some embodiments, the cell line is human or murine. In some embodiments, the modifications comprise genetic knockouts, whereby the cell line becomes genetically deficient for one or more genes. In some embodiments, the modifications comprise making transgenic cell lines, whereby the cell line obtains genetic material not present in the wildtype cell line or genetic material under the control of active promoter.

The term "genetically deficient" as used herein refers to a genome that is modified to be missing one or more genes of interest. In some embodiments, the modification is made using a cre/lox system, CRISPR, siRNA, shRNA, antisense oligonucleotide, miRNA, or other genetic modification or mutagenesis method known in the art.

The term "transgenic" as used herein refers to a genome that is modified to include additional genetic material encoding one or more genes of interest. In some embodiments, the modification is made using transfection, infection with a virus, cre/lox knock-in, CRISPR/cas mediated knock-in, or other method of introducing genetic material to a cell that is known in the art.

The terms "subject", "individual", "recipient", "host", and "patient", are used interchangeably herein and refer to any mammalian subject for whom diagnosis, treatment or therapy is desired, particularly humans. "Mammal" for purposes of treatment refers to any animal classified as a mammal, including humans, domestic and farm animals, and laboratory, zoo, spots, or pet animals, such as dogs, horses, cats, cows, sheep, goats, pigs, mice rats, rabbits, guinea pigs, monkeys, etc. In some embodiments, the mammal is human.

As used herein, the terms "treatment", "treating" and the like, refer to administering an agent or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment", as used herein, may include treatment of a disease in a mammal, particularly in a human and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease. Treating may refer to any indicia of success in the treatment or amelioration or prevention of a disease, including any objective or subjective parameter such as abatement; remission; diminishing of symptoms or making the disease more tolerable to the patient; slowing in the rate of degeneration or decline; or making the final point of degeneration with less debilitation. The treatment or amelioration of symptoms can be based on objective or subjective parameters; including the results of an examination by a physician. Accordingly, the term "treating" includes the administration of the compounds or agents disclosed hereinto prevent or delay, to alleviate, or to arrest or inhibit development of the symptoms of conditions associated with the disease. The term "therapeutic effect refers to the reduction, elimination, or prevention of the disease, symptoms of the disease, or side effects of the disease in the subject.

"In combination with "combination therapy" and "combination products" refer, in certain embodiments, to concurrent administration to a patient of a first therapeutic and the compounds used herein. When administered in combination, each component can be administered at the same time or sequentially in any order at different points in time. Thus, each component can be administered separately but sufficiently closely in time as to provide the desired therapeutic effect.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or in the case of an aerosol composition, gaseous.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means that the amount that, when administered to a subject for treating a disease, is sufficient to effect treatment for that disease.

The term "substantially free" as used herein means most or all of one or more of a contaminant, such as the materials with which it typically associates with in nature, is absent from the composition. Thus a glycosaminoglycan composition such as heparan sulfate, chondroitin sulfate, keratan sulfate, and hyaluronic acid composition with defined modification patterns described herein that is "substantially free" from one or more contaminating glycosaminoglycans that do not have the desired defined modification pattern and/or biological and/or therapeutic effect has no or little of the contaminant. For example, a heparan sulfate composition is "substantially free" from a contaminant such as other glycosaminoglycans such as: chondroitin sulfate, keratan sulfate and/or hyaluronic acid; nucleic acids; and/or proteins, found with the heparan sulfate composition in nature, has very little or none of the contaminant, for example less than 5%, less than 4%, less than 3%, less than 2%, less than 1%, or less than 0.5% of the composition is made up by the contaminant. In some embodiments, the composition is 60%, 70%, 80%, 85%, 90%, 95%, 96%, 97%, 98%, 99%, or 100% free from one or more of a contaminating glycosaminoglycan, nucleic acids, and or proteins. In some embodiments, the composition is at least 95% free from contaminating glycosaminoglycans, nucleic acids, and or proteins. In some embodiments, the composition is at least 99% free from contaminating glycosaminoglycans, nucleic acids, and or proteins.

The term "substantially pure" as used herein means that the composition is free of most or all of the materials with which it typically associates with in nature. Thus a "substantially pure" glycosaminoglycans such as heparan sulfate, chondroitin sulfate, keratan sulfate, and hyaluronic acid composition with defined modification patterns described herein does not include other contaminating glycosaminoglycans such as heparan sulfate, chondroitin sulfate, keratan sulfate, and hyaluronic acid compositions that do not have the desired defined modification pattern and/or biological and/or therapeutic effect. For example, a "substantially pure" heparan sulfate composition is free from most other glycosaminoglycans such as: chondroitin sulfate, keratan sulfate and/or hyaluronic acid; nucleic acids; and/or proteins, found with the heparan sulfate composition in nature. In some embodiments, the composition is 60%, 70%, 80%, 85%, 90%, 95%, 96%, 97%, 98%, 99%, or 100% free from contaminating glycosaminoglycans, nucleic acids, and or proteins. In some embodiments, the composition is at least 95% free from contaminating glycosaminoglycans, nucleic acids, and or proteins. In some embodiments, the composition is at least 99% free from contaminating glycosaminoglycans, nucleic acids, and or proteins.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Genetically Altered Cell Lines and Heparan Sulfate Compositions Therefrom Cell Culture CHO—S cells (Life Technologies) were routinely cultured in 30 ml of CD CHO Expression Medium (Life Technologies) with 8 mM GlutaMAX (Life Technologies) in 125 ml shaker culture flasks (VWR) on a rotating platform (130 rpm) at 37° C. and 5% $CO_2$. For GAG production, the cells were cultured as described. Briefly, cells were seeded at $0.2 \times 10^6$ cells/ml in CD CHO Expression medium plus 8 mM GlutaMAX. On days 3, 5 and 7 three milliliters of CD CHO EfficientFeed B were added to the flaks. The conditioned medium was harvested on day 10. The cells were spun out of the medium (5000 rpm, 10 minutes performed twice) and the supernatant was stored at −20° C. until further processing. This has been scaled up to multiple 1 liter flasks (300 ml each) to produce large batches.

CRISPR/Cas Modification of CHO—S Cells

Mutation of GAG biosynthetic genes in CHO—S cells was accomplished by transient coexpression of Cas9 with a guide RNA sequence. Guide RNA (sgRNA) sequences were designed using "CRISPy" described in the reference Rhonda C, Pedersen L E, et al. Biotechnol Bioeng. 2014 August; 111(8):1604-16. Sequences for sgRNAs are shown in Table 4. Oligonucleotides for each sgRNA were purchased (ValueGene) and ligated into pSpCas9(BB)-2A-puro (Addgene). CHO—S cells were transfected with the ligated plasmid using FreeStyle MAX Transfection Reagent (Life Technologies). After 48 hours of transfection, the medium was changed to regular growth medium and the cells were allowed to recover for 24 hours. DNA was extracted from the cells using QuickExtract DNA extraction solution (Epicentre). The targeted genomic regions were amplified by PCR using Herculase II (Aglient Technologies) and PCR primers. Genetic mutations were detected using the SURVEYOR nuclease assay (Integrated DNA Technologies).

Clonal cell lines were created by limiting dilution cloning of the transfected population. Cells were diluted to 10 cells/ml into CD FortiCHO medium (Life Technologies) with 6 mM GlutaMAX (Life Technologies) and 200 µl were plated into each well of 96-well plates. The plates were incubated at 37° C., 5% $CO_2$ in a humidified chamber. After 12 days, the plates were checked for colony formation. Colonies were transferred sequentially to 24-well plates and 6-well plates before screening by flow cytometry for cell surface chondroitin sulfate using antibody 2B6 or alteration of heparan sulfate by FGF2 binding. Colonies that were deficient in chondroitin sulfate or having altered FGF2 binding were transferred to 20 ml of CD CHO Expression medium (Life Technologies) with 8 mM GlutaMAX for further growth and analysis.

To determine the specific mutation in a clonal cell line, the targeted genomic region was PCR amplified. The purified PCR product was cloned into pUC19, which was subsequently transformed into E. coli and isolated from plated colonies for sequencing (Genewiz).

Detection of Cell Surface Chondroitin Sulfate

Cell surface chondroitin sulfate was detected by flow cytometry using the antibody 2B6 (Amsbio). This antibody is specific to the 4-O-sulfated chondroitin sulfate stub epitope revealed by chondroitinase ABC digestion. $0.2 \times 10^6$ cells were placed in each well of a V-bottom 96-well plate (Corning). For screening colonies in 6-well plates, 200 µl of culture medium was transferred to the 96-well plate. The cells were washed into fresh culture medium with 10 mU/ml chondroitinase ABC (Amsbio) and incubated for 30 minutes at 37° C. A second well was incubated with fresh culture medium alone as a control. Following digestion, the cells were washed twice with 200 µl of chilled dPBS (Lonza) and incubated with a 1:200 dilution of 2B6 in dPBS plus 0.1% BSA (Sigma) for 1 hour at 4° C. The cells were then washed again and incubated with 1:100 dilution of goat anti-mouse IgG-Cy3 (Jackson ImmunoResearch) for 1 hour at 4° C. The cells were washed again and analyzed by flow cytometry on a Guava PCA-96.

Detection of FGF2 Bound to the Cell Surface

Recombinant human FGF2 (Shenandoah Biotechnology) was bound to a heparin-Sepharose column in dPBS and biotinylated using 0.6 mg/ml sulfo-NHS-LC-biotin (Thermo) in dPBS. After 1 hour incubation at room temperature, the column was washed with dPBS and then bound biotin-FGF2 was eluted in dPBS plus 2 M NaCl. This material was subsequently used to measure FGF2 binding to the cell surface.

$0.2 \times 10^6$ cells (or 200 µl of culture medium when screening colonies) were transferred to a 96-well V-bottom plate (Corning) and washed into dPBS. The cells were incubated with a 1:500 dilution of biotin-FGF2 in PBS with 0.1% BSA for 1 hour at 4° C. The cells were washed and incubated with a 1:1000 dilution of streptavidin-phycoerythrin (eBioscience) in PBS with 0.1% BSA for 30 minutes at 4° C. After a final wash in dPBS, the cells were analyzed by flow cytometry on a Guava PCA-96.

Glycosaminoglycan Purification

Glycosaminoglycan (GAG) was purified from CHO—S conditioned medium. First, the conditioned medium was fractionated on DEAE-Sephacel, equilibrated and washed with 50 mM NaAcO, 250 mM NaCl, pH 6.0, and eluted with 50 mM NaAcO, 1 M NaCl, pH 6.0. For GAG preparation from cells with Ndst1 and Ndst2 targeted, the concentration of NaCl was lowered to 150 mM in the equilibration/wash buffer. The resulting eluate was diluted 6-fold in MilliQ water. Then, $CaCl_2$ was added to 5 mM. 60 Kunitz DNase I (Sigma) was added and allowed to incubate overnight at 37° C. The following day, Pronase (Sigma) was added to 0.5 mg/ml and allowed to incubate for 3 hours at 37° C. The preparation was again purified over DEAE as before and desalted on a PD-10 column equilibrated in 10% ethanol. The desalted GAG was dried on a SpeedVac and stored at −20° C. In some cases, the GAG was beta-eliminated by resuspending dried GAG in 0.4 M NaOH and incubating overnight at 4° C. The solution was neutralized with addition of acetic acid, desalted on PD-10 and dried on a SpeedVac.

GAG Quantification

GAG was quantified by carbazole assay as previously described. Briefly, up to 100 µl of purified GAG was incubated with 10 µl of 4 M ammonium sulfamate and 500 µl of 25 mM sodium tetraborate in $H_2SO_4$ at 95° C. for 5 minutes. After cooling to room temperature, 20 µl of 0.1% carbazole in ethanol was added and the samples were heated to 95° C. for 15 minutes. Glucuronic acid in the samples was measured by absorbance at 520 nM. Samples prepared in parallel using 0-10 µg of glucuronic acid served as the standard curve.

To measure chondroitin sulfate or heparan sulfate production specifically, purified GAG was digested exhaustively with heparin lyases or chondroitinase ABC (Amsbio) and remaining GAG was repurified and quantified by carbazole assay. Heparin lyases were produced as described previously. For chondroitin sulfate quantification, digestion was performed in 50 mM NaAcO, 5 mM CaAcO, pH 7.0 with 2.5 mU/ml each heparin lyases I, II and III, overnight at 37° C. For heparan sulfate quantification, digestion was performed in 50 mM Tris, 50 mM NaAcO, pH 8.0 with 5 mU/ml chondroitinase ABC, overnight at 37° C.

Alternatively, heparan sulfate and chondroitin sulfate in the samples were detected by lyase digestion UV absorbance. 40 µl of purified GAG was diluted 5 fold with water and transferred to a 96-well UV transparent plate. 22 µl of 10× heparin lyase (500 mM NaAcO, 5 mM CaAcO, pH 7.0) or 10× chondroitinase buffer (500 mM Tris, 500 mM NaAcO, pH 8.0) were added to the well. A baseline absorbance measurement was made at 250 nm before addition of either 1 mU each heparin lyases I, II, III or 1 mU chondroitinase ABC. The wells were sealed with parafilm and incubated at 37° C. for 30 minutes before taking another measurement at 250 nm. The measurement was repeated after 5 minutes to verify that the reaction had gone to completion.

Heparan Sulfate Disaccharide Analysis

Disaccharide composition of heparan sulfate was determined by GRIL-LC/MS as previously described. Briefly, for each analysis, 5 g of purified heparan sulfate was dried down and resuspended in 100 µl heparin lyase buffer (50 mM NaAcO, 5 mM CaAcO, pH 7.0) with 2 mU/ml each heparin lyases I, II and III. Samples were digested overnight at 37° C. and then dried on a SpeedVac. Each sample was aniline tagged by incubation with aniline and reductant. Reductant consisted on 150 mg $NaCNBH_4$ (Sigma) dissolved in 1.4 ml of DMSO (Sigma) and 0.6 ml of glacial acetic acid (Fisher). 17 µl of aniline (Sigma) was added to each sample followed immediately by 17 µl of reductant. The sample was vortexed to bring the dried heparan sulfate into solution and then incubated overnight at 37° C. The tagged sample was then dried to completion on a SpeedVac and stored at −20° C. until analysis by LC/MS by the Glycotechnology Core Resource at the University of California, San Diego.

Preparation of Extracellular Matrix (ECM)

To prepare gelatin-coated substrates, tissue culture plates were incubated with 0.1% gelatin for 30 minutes. Established procedures were used for preparing the cell-free decellularized matrix. Briefly, ChA27 derived cell lines were cultured in wells of a 24-well plate until highly confluent. Cells were washed twice with 1 ml PBS followed by two washes with 1 ml of wash buffer I (100 mM Na2HPO4, pH 9.6, 2 mM MgCl2, 2 mM EGTA). 1 ml lysis buffer (8 mM Na2HPO4, pH 9.6, 1% NP-40) was added to each well and incubated at 37° C. for 15 minutes; this was then removed and replaced with 1 ml fresh lysis buffer and incubation was continued for 40-60 minutes. Matrices were washed twice with 1 ml wash buffer II (300 mM KCl, 10 mM Na2HPO4, pH 7.5) and four times with 1 ml dH2O. Matrix could be stored in PBS at 4° C. for a few weeks.

Example 2: Chondroitin Sulfate Deficient CHO Cells

Figure 2:
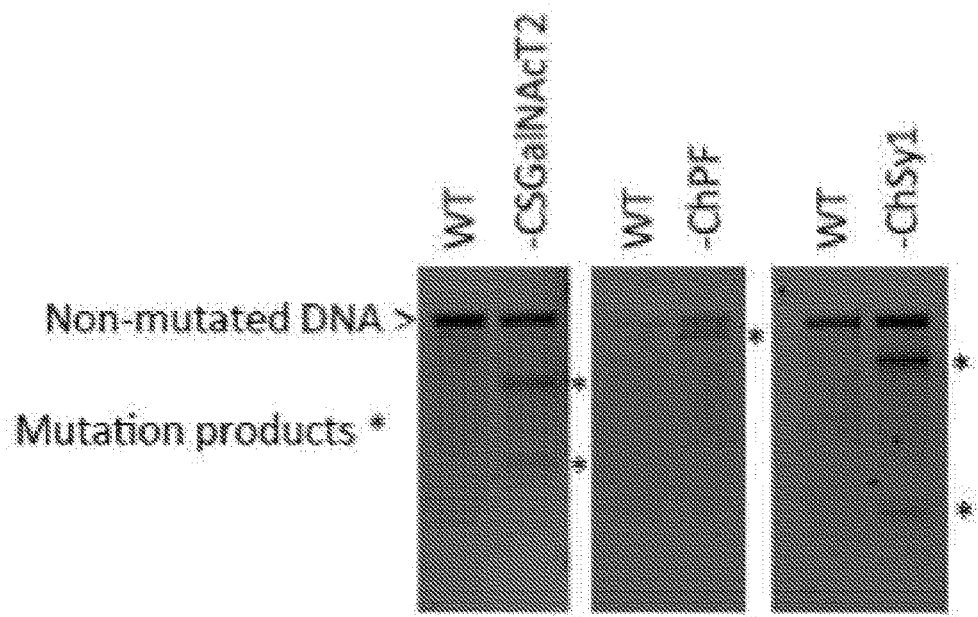
FIG. 2 shows SURVEYOR mutation assay after transfection of guide RNAs to knockout CS production. Genomic DNA was extracted from cells that had been transiently transfected with pSpCas9 and a sgRNA directed toward CSGalNAcT2, ChPF or ChSy1. The genomic locus containing the sgRNA target was PCR amplified. The PCR amplicons were purified and digested with SURVEYOR nuclease. The digest products were visualized on an agarose gel. The size of each mutation product matches the expected molecular weight based on the position of the mutation within the PCR amplicon.
Figure 3:
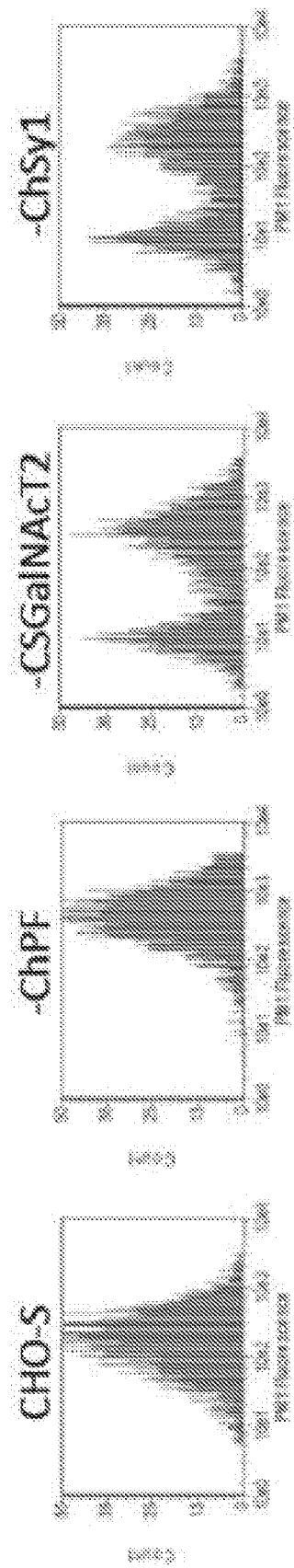
FIG. 3 shows flow cytometry to detect CS on the surface of transfected cells. CHO—S cells were transfected with pSpCas9 and with sgRNA targeting ChPF, CSGalNAcT2 or ChSy1. The cells were treated with chondroitinase ABC and then incubated with antibody 2B6 (which detects the 4-O-sulfated CS stub remaining after chondroitinase treatment) and a Cy3 conjugated secondary antibody before analysis by flow cytometry.

Tissue culture cells express proteoglycans on their surfaces and secrete proteoglycans into the medium. Secreted proteoglycans are prepared by anion exchange chromatography followed by enzymatically digesting the nucleic acid components, followed by protease digestion and beta-elimination to eliminate the core protein from the glycosaminoglycan (GAG) chains and then separating the GAG chains from the digested components on anion exchange columns. For heparan sulfate preparation, chondroitin sulfate (CS) would then be digested from wildtype CHO cell material. To avoid this digestion step, saving the cost of chondroitinase, and to eliminate any possible contamination with CS, CS expression was genetically eliminated from the CHO cells used for heparan sulfate production. Heparan sulfate and CS are synthesized from a common precursor. Heparan sulfate chains are initiated by the enzyme ExtL3 catalyzed addition of N-acetylglucosamine residues to tetrasaccharide primers extending from core proteins (see FIG. 1) in the Golgi. Heparan sulfate chains are then extended by subsequent additions of glucuronic acid and N-acetylglucosamine disaccharides catalyzed by Ext1 and Ext2. Alternatively, addition of N-acetylgalactosamine initiates CS chain synthesis. Initiation of heparan sulfate and CS is independent so eliminating the enzyme(s) responsible for CS initiation eliminated CS synthesis with no apparent heparan sulfate synthesis effects. Candidate genes for targeting were based partially on a CHO-K1 mRNA expression profile that revealed the subset of CS synthetic genes expressed in CHO cells. Three candidate genes for CS chain initiation were identified; chondroitin synthase 1 (ChSy1), chondroitin polymerizing factor (ChPF) and CS N-acetylgalatosamine transferase 2 (CSGalNAcT2). These three genes were genetically targeted separately to eliminate CS chain production. Genes were inactivated by transfection with a vector expressing Cas9 and sgRNA targeted specifically to each gene. Electrophoresis revealed that transfection produced doublet bands after SURVEYOR nuclease digestions, indicative of mismatches due to indel (insertion/deletion) mutations (FIG. 2). Flow cytometry on the targeted cell populations revealed that inactivation of ChPF did not alter CS synthesis whereas targeted mutations of ChSy1 and CSGaNAcT2 reduced CS synthesis in large fractions of the cells (FIG. 3). No differences were seen by flow cytometry when double and triple transfections were performed by mixing sgRNAs targeting the three genes (data not shown).

Figure 4:
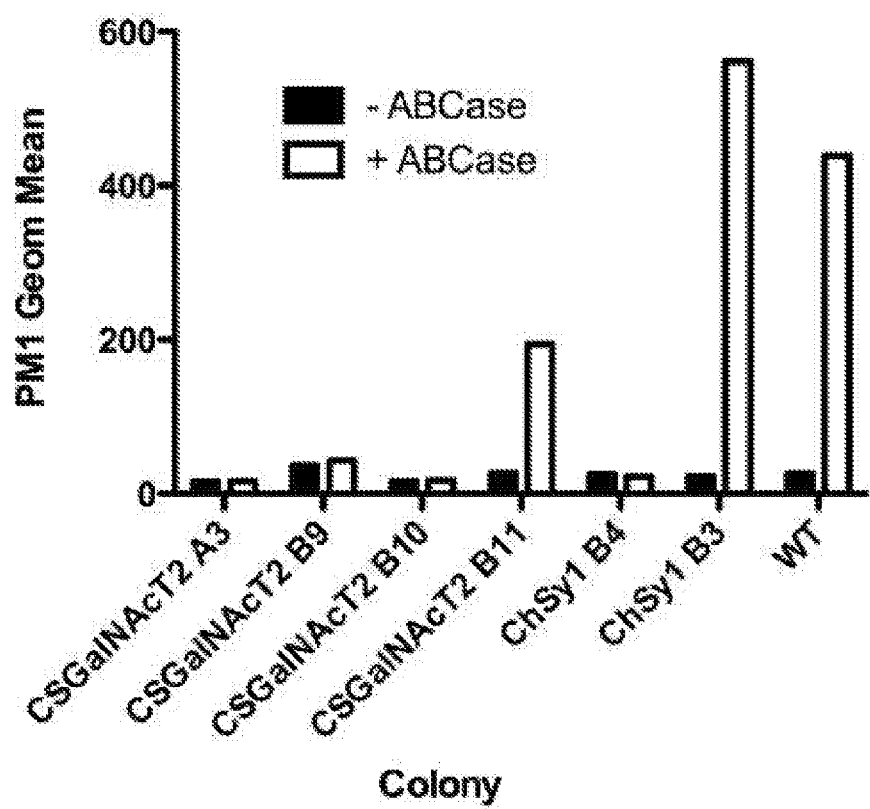
FIG. 4 shows flow cytometry to screen clonal cell lines for knockout of CS synthesis. Clonal populations derived from limiting dilution cloning were treated with chondroitinase ABC and then incubated with antibody 2B6 to identify cell lines that were deficient in CS synthesis. A representative experiment is shown. In all, more than 100 colonies were screened.
Figure 5A:
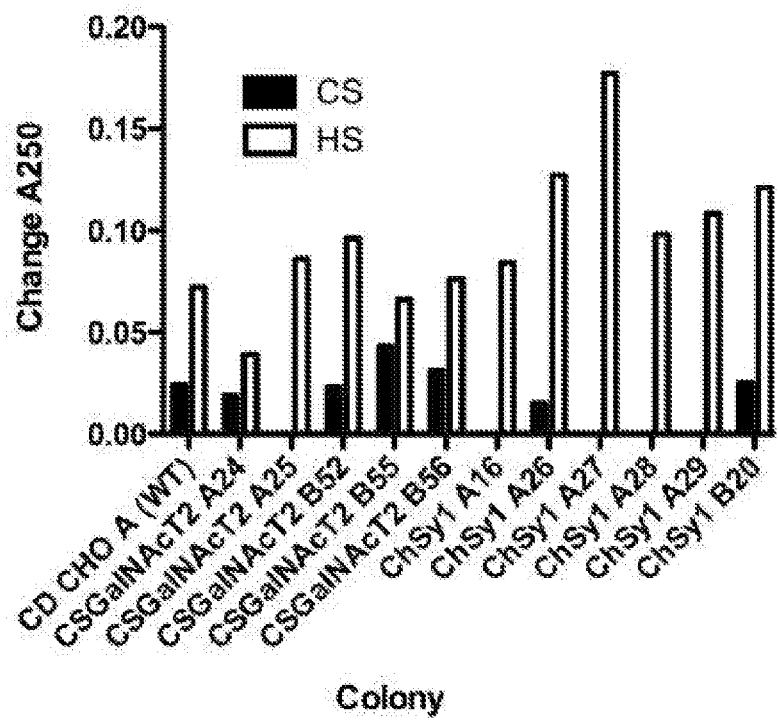
FIGS. 5A-B shows measurement of GAG production in targeted and screened cell lines. GAG was purified from the conditioned medium of screened cell lines.

Subsequent limited dilution cloning isolated cloned cell lines deficient for CS biosynthesis from populations targeted for either ChSy1 or CSGalNAcT2. Cloned cell lines were initially screened by flow cytometry (FIG. 4). CS deficiencies in individual cloned cell lines were then assessed by lyase digestion on purified GAG. GAG chains isolated from individual cloned cell lines were analyzed by changes in UV absorbance following lyase digestion. Parallel ABCase and heparin lyases 1, II and III digests of the GAG chains were incubated in UV transparent plates on a spectrophotometer. All of the clones demonstrated increased absorbance following digestion with heparin lyases. (FIG. 5A).

Figure 5B:
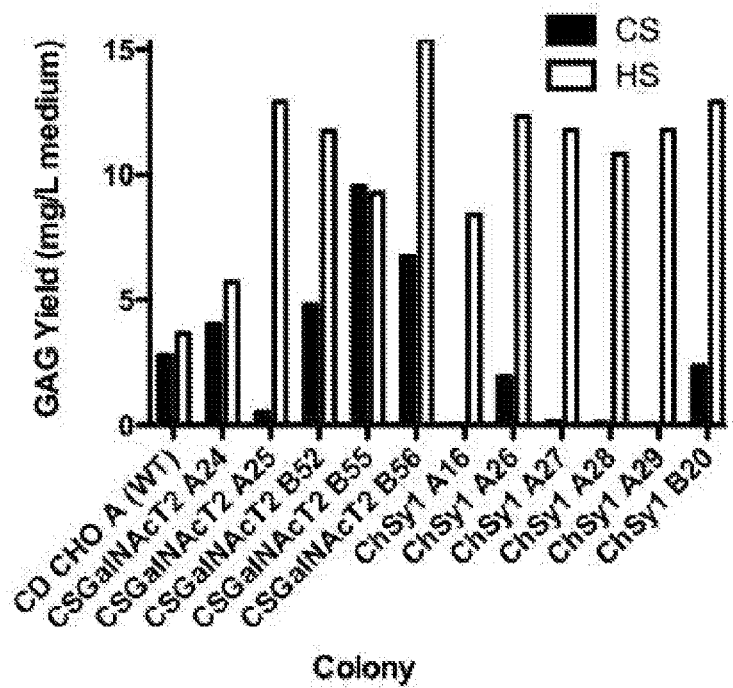
Figure 6:
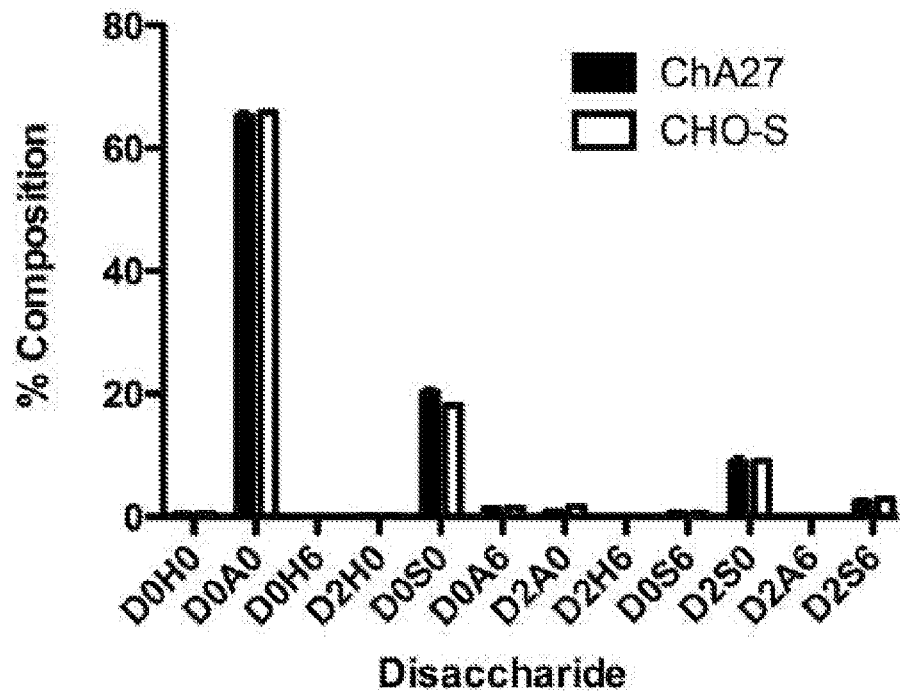
FIG. 6 shows HS disaccharide composition of CHO—S and CS knockout cells. GAG was purified from the conditioned medium of CHO—S and ChSy1 knockout clones. The HS was digested exhaustively with heparin lyases, then aniline tagged and analyzed by LC/MS. Isotopic standard disaccharides provided means for identification and quantification of each disaccharide. Data shown is mean±S.E.M.

Individual clones were chosen that showed no increase in absorbance over background following ABCase digestion. Although CS deficient cell lines resulted from inactivation of both ChSy1 and CSGalNAcT2 genes, final selection of a cell line for heparan sulfate productions was based on the absolute level of heparan sulfate production. Heparan sulfate production levels varied somewhat among the CS deficient cell lines (FIG. 5B). ChA27 (ChSy1 deficient) was chosen because the cells consistently demonstrated high heparan sulfate levels by carbazole and absorbance assays. Disaccharide analyses of the heparan sulfate produced in the cell lines revealed no differences between ChSy1 deficient cell lines (data not shown) or between CHO—S cells and the ChSy1 deficient cell lines (FIG. 6).

For final verification of selected clones, GAG preparations were quantified by carbazole assays and then either digested with chondroitinase ABC (ABCase) or heparin lyases I, II and III. In the selected clones, quantification was unchanged by digestion with ABCase whereas GAG chains were entirely eliminated by digestion with the heparin lyases demonstrating the absence of CS and therefor the absence of CS synthesis in these cells (FIG. 5B). In 125 ml shaker flasks, heparan sulfate production yielded 10-12 mg/liter.

Figure 7:
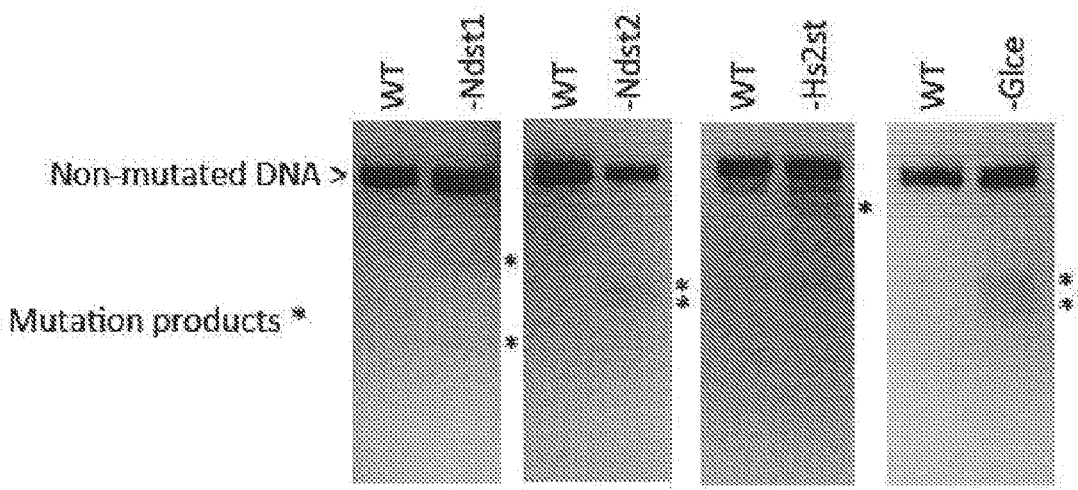
FIG. 7 shows SURVEYOR mutation assay after transfection to alter HS production. Genomic DNA was extracted from cells that had been transiently transfected with pSpCas9 and a sgRNA directed toward Ndst1, Ndst2, Hs2st or Glce. The genomic locus containing the sgRNA target was PCR amplified. The PCR amplicons were purified and digested with SURVEYOR nuclease. The digest products were visualized on an agarose gel. The size of each mutation product matches the expected molecular weight based on the position of the mutation within the PCR amplicon.

Example 3: ChA27 Cells with Altered Heparan Sulfate Modification Enzyme Expression: Engineering ChA27 Cell Heparan Sulfate Expression ChA27 cell lines producing heparan sulfate with different biological properties were engineered by altering the expression of specific heparan sulfate modification enzymes. Selection of genes to target for knockout was guided by expression data for heparan sulfate biosynthesis genes in CHO-K1 (unpublished data) and heparan sulfate disaccharide composition (FIG. 6). Genes encoding N-deacetylase/N-sulfotransferase 1 (Ndst1), N-deacetylase/N-sulfotransferase 2 (Ndst2), heparan sulfate 2-O sulfotransferase (Hs2st) and heparan sulfate C5-epimerase (Glce) were separately inactivated. Blocking the expression of these enzymes will change the composition of the heparan sulfate chains by reducing or preventing N-sulfation of N-acetylglucosamine residues, 2-O-sulfation of glucuronic and iduronic residues and epimerization of glucuronic acid residues to iduronic acid. Since these modifications are important components of various ligand binding sites, heparan sulfate from the engineered cell lines will have unique ligand binding profiles relative to the unmodified ChA27 cells and therefore different biological properties. Genes of interest were knocked out by transfection of a vector that expresses Cas9 and the sgRNA targeted to a specific biosynthetic gene. Electrophoresis revealed that transfection produced doublet bands after SURVEYOR nuclease digestions (FIG. 7).

Figure 8:
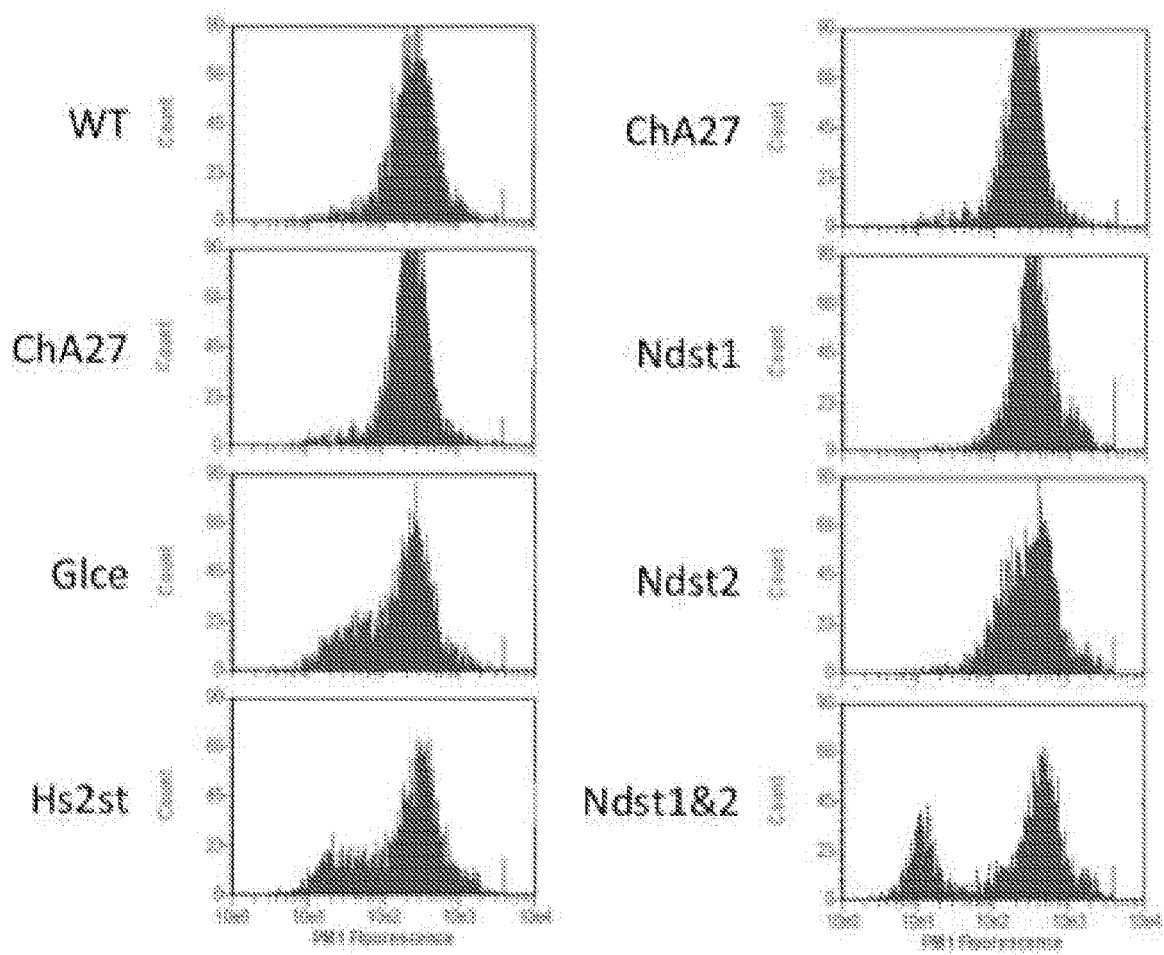
FIG. 8 shows flow cytometry to detect changes in FGF2 binding to HS on the surface of transfected cells. ChA27 cells were transfected with pSpCas9 with sgRNA targeting Ndst1, Ndst2, Hs2st, Glce, Hs6st1 and Ndst1/Ndst2. The cells were incubated with biotinylated-FGF2 and streptavidin-phycoerythrin before analysis by flow cytometry.

Decreased FGF2 cell surface binding identified cells deficient for Hs2st, Glce and Ndst1/Ndst2 double knock out of these genes by flow cytometry (FIG. 8). Single mutations with Ndst1 or Ndst2 did not produce a distinct population by FGF2 binding and flow cytometry. Subsequent limiting dilution cloning isolated cloned cell lines deficient for the various heparan sulfate modifications (decreased FGF2 binding) by flow cytometry FIG. 9. A series of engineered cell lines is planned with a wide variety of genetic modifications (see Table 1 for some of the modifications).

Example 4: Structural Properties

Figure 11:
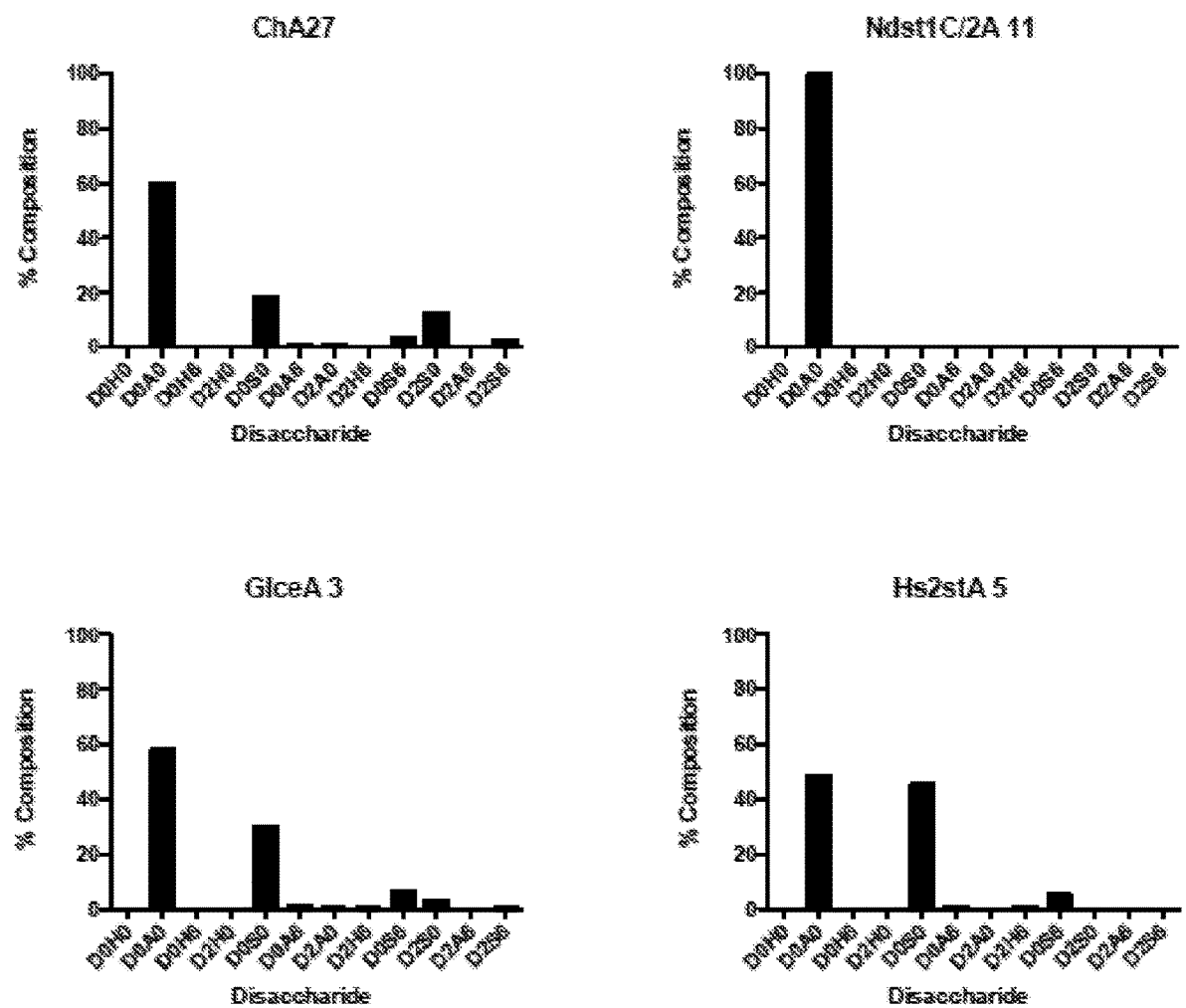
FIG. 11 shows HS disaccharide compositions of clone ChA27 before and after various gene knockouts using CRISPR/Cas. GAG was purified from the conditioned medium of cloned cell lines. The HS was digested exhaustively with heparin lyases, then aniline tagged and analyzed by LC/MS. Isotopic standard disaccharides provided means for identification and quantification of each disaccharide. Data shown is a single analysis of HS from a single cloned cell line. Gene knockout is indicated for each panel.

To demonstrate that the isolated cell lines were deficient for the various enzyme activities, the targeted genes were sequenced (FIG. 10). Heparan sulfate was then prepared from the cell lines and analyzed by disaccharide analyses (FIG. 11).

Example 5: Heparan Sulfate Ligand Binding Properties

Biological activities of the heparan sulfate from the various cell lines are characterized as the heparan sulfate is tested in various biological systems. Since the biological activities of heparan sulfate largely result from the ligand binding properties, heparan sulfate produced by the various cell lines is tested for binding to a panel of ligands by flow cytometry by binding heparan sulfate that is immobilized on a 96-w plate. (see Table 3).

Example 6: Heparan Sulfate Biological Properties

Mutations in the heparan sulfate modification enzymes cause a variety of developmental defects in mice and in vitro differentiation of embryonic stem cells. ESCs exhibit different developmental defects depending on which enzymes are mutated and an even more complex array of developmental effects may result from targeting specific genes, as many of the modification enzymes are members of multi-isoform families with potentially different but overlapping functions.

For example Hs2st-/- ESC lines completely lack 2-O-sulfate groups but the decrease in sulfation appears to be compensated for by increases in N-sulfation and 6-O-sulfation. The cells show marked defects in proliferation and development under neuronal differentiation conditions, whereas hematopoietic differentiation appears to proceed normally. Alternatively, when 6-O-sulfation is increased through inactivation of sulfatase genes (Sulf1/2-/-) developmental defects appear to a lesser degree under neuronal differentiation conditions but defects in hematopoietic differentiation appear. Thus expression levels of the various heparan sulfate modification enzymes appear to exert a very tight control on 6-O-sulfation levels and perhaps on the levels of other modifications and therefore on the heparan sulfate chain compositions that determine the structures of the oligosaccharides and their protein binding specificities.

Due to the adhesion and ligand binding properties of heparan sulfate, heparan sulfate proteoglycans and GAGs in the extracellular matrix (ECM) also play important roles in cell and tissue growth and differentiation. Decellularized matrix derived from genetically modified cell lines will contain heparan sulfate with different growth factor binding properties and thus can be used to characterize the expressed heparan sulfate structures biologically with respect to ESC differentiation. This characterization will aid in selecting the important heparan sulfate structures for particular cell physiological and pathophysiological studies.

Tissue culture cell derived ECMs have been used to analyze the influence of ECM components under a variety of differentiation conditions. Here, ECM prepared from the various engineered cell lines was used to test the influence of the different heparan sulfate compositions in directing mouse embryonic stem cell (ESC) differentiation.

Example 7: Treatment of Cancer

A subject with a tumor, such as a hepatocellular carcinoma is administered an effective dose of a heparan sulfate composition with a defined pattern of sulfation. After administration of this treatment, the subject shows a decrease in the size of the tumor and an improved prognosis and survival time. When this treatment is administered to a group of subjects, for example 10, 20, 30 or more patients and the results are compared to another group of subjects, for example 10, 20, 30 or more patients who receive a different treatment, the patients receiving the heparan sulfate treatment have a better prognosis than patients receiving the other treatment.

Example 8: Treatment of Neurodegenerative Disease

A subject with a neurodegenerative disease, such as Alzheimer's Disease is administered an effective dose of a heparan sulfate composition with a defined pattern of sulfation. After administration of this treatment, the subject shows an decrease symptoms, slower disease progression, and increased survival time. When this treatment is administered to a group of subjects, for example 10, 20, 30 or more patients and the results are compared to another group of subjects, for example 10, 20, 30 or more patients who receive a different treatment, the patients receiving the heparan sulfate treatment have a better prognosis than patients receiving the other treatment.

Example 9: Treatment of Microbial Infection

A subject with a microbial infection, such as MRSA is administered an effective dose of a heparan sulfate composition with a defined pattern of sulfation. After administration of this treatment, the subject shows an improvement in symptoms and the infection is resolved. When this treatment is administered to a group of subjects, for example 10, 20, 30 or more patients and the results are compared to another group of subjects, for example 10, 20, 30 or more patients who receive a different treatment, the patients receiving the heparan sulfate treatment have recover more quickly than patients receiving the other treatment.

TABLE 1

| Cell lines producing modified heparan sulfate ||||
| Cell Line ID | Gene KO | Gene KI | Enzymes |
| --- | --- | --- | --- |
| CHA27 | Chsy1 | | CS deficient |
| CHA27 – 2S | Chsy1 Hs2st | | CS deficient HS 2O-sulfation deficient |
| CHA27 – GLCE | ChSy1 Glce | | CS deficient HS epimerization deficient |
| CHA27 – NS1 | Chsy1 Hsndst1 | | CS deficient HS NDST1-sulfation deficient |
| CHA27 – NS2 | Chsy1 Hsndst2 | | CS deficient HS NDST2-sulfation deficient |
| CHA27 – NS1/2 | Chsy1 Hsndst1 Hsndst2 | | CS deficient HS NDST1-sulfation deficient HS NDST2-sulfation deficient |
| CHA27 – NS3 | Chsy1 Hsndst3 | | CS deficient HS NDST3-sulfation deficient |
| CHA27 – NS4 | Chsy1 Hsndst4 | | CS deficient HS NDST4-sulfation deficient |
| CHA27 – Sulf1 | Chsy1 Sulf1 | | CS deficient Sulfatase 1 deficient |
| CHA27 – Sulf2 | Chsy1 Sulf2 | | CS deficient Sulfatase 2 deficient |
| CHA27 – Sulf1/2 | Chsy1 Sulf1/2 | | CS deficient Sulfatase 1 deficient Sulfatase 2 deficient |
| CHA27 – N1/2 + NS3 | Chsy1 Hsndst1 Hsndst2 | Hsndst3 | CS deficient HS NDST1-sulfation deficient HS NDST2-sulfation deficient HS NDST3-sulfation Added |
| CHA27 – NS1/2 + N4 | Chsy1 Hsndst1 Hsndst2 | Hsndst4 | CS deficient HS NDST1-sulfation deficient HS NDST2-sulfation deficient HS NDST4-sulfation Added |
| CHA27 + 6S1 | Chsy1 | Hs6stβ1 | CS deficient HS 6OST1-sulfation Added |
| CHA27 + 6S2 | Chsy1 | Hs6st2 | CS deficient HS 6OST2-sulfation Added |
| CHA27 + 6S3 | Chsy1 | Hs6st3 | CS deficient HS 6OST3-sulfation Added |
| CHA27 + 6S1/2 | Chsy1 | Hs6st1 Hs6st2 | CS deficient HS 6OST1-sulfation Added HS 6OST2-sulfation Added |
| CHA27 + 3S1 | Chsy1 | Hs3st1 | CS deficient HS 3OST1-sulfation Added |
| CHA27 + 3S2 | Chsy1 | Hs3st2 | CS deficient HS 3OST-2sulfation Added |
| CHA27 + 3S3a | Chsy1 | Hs3st3a | CS deficient HS 3OST3a-sulfation Added |
| CHA27 + 3S3b | Chsy1 | Hs3st3b | CS deficient HS 3OST3b-sulfation Added |
| CHA27 + 3S4 | Chsy1 | Hs3st4 | CS deficient HS 3OST4-sulfation Added |
| CHA27 + 3S5 | Chsy1 | Hs3st5 | CS deficient HS 3OST5-sulfation Added |
| CHA27 + 3S6 | Chsy1 | Hs3st6 | CS deficient HS 3OST6-sulfation Added |
| CHA27 + 6S1/2 + 3S1 | Chsy1 | Hs6st1 Hs6st2 Hs3st1 | CS deficient HS 6OST1-sulfation Added HS 6OST2-sulfation Added HS 3OST1-sulfation Added |
| CHA27 + 6S1/2 + 3S2 | Chsy1 | Hs6st1 Hs6st2 Hs3st2 | CS deficient HS 6OST1-sulfation Added HS 6OST2-sulfation Added HS 3OST2-sulfation Added |

TABLE 1-continued

Cell lines producing modified heparan sulfate

| Cell Line ID | Gene KO | Gene KI | Enzymes |
|---|---|---|---|
| CHA27 + 6S1/2 + 3S3a or 3b | Chsy1 | Hs6st1 Hs6st2 Hs3st3a or 3b | CS deficient<br>HS 6OST1-sulfation Added<br>HS 6OST2-sulfation Added<br>HS 3OST3-sulfation Added |
| CHA27 + 6S1/2 + 3S4 | Chsy1 | Hs6st1 Hs6st2 Hs3st4 | CS deficient<br>HS 6OST1-sulfation Added<br>HS 6OST2-sulfation Added<br>HS 3OST4-sulfation Added |
| CHA27 + 6S1/2 + 3S5 | Chsy1 | Hs6st1 Hs6st2 Hs3st5 | CS deficient<br>HS 6OST1-sulfation Added<br>HS 6OST2-sulfation Added<br>HS 3OST5-sulfation Added |
| CHA27 + 6S1/2 + 3S6 | Chsy1 | Hs6st1 Hs6st2 Hs3st6 | CS deficient<br>HS 6OST1-sulfation Added<br>HS 6OST2-sulfation Added<br>HS 3OST6-sulfation Added |
| CHA27 − N1/2 + NS3 + 6S1 | Chsy1 Hsndst1 Hsndst2 | Hsndst3 Hs6st1 | CS deficient<br>HS NDST1-sulfation deficient<br>HS NDST2-sulfation deficient<br>HS NDST3-sulfation Added<br>HS 6OST1-sulfation Added |
| CHA27 − N1/2 + NS3 + 6S2 | Chsy1 Hsndst1 Hsndst2 | Hsndst3 Hs6st2 | CS deficient<br>HS NDST1-sulfation deficient<br>HS NDST2-sulfation deficient<br>HS NDST3-sulfation Added<br>HS 6OST2-sulfation Added |
| CHA27 − N1/2 + NS3 + 6S3 | Chsy1 Hsndst1 Hsndst2 | Hsndst3 Hs6st3 | CS deficient<br>HS NDST1-sulfation deficient<br>HS NDST2-sulfation deficient<br>HS NDST3-sulfation Added<br>HS 6OST3-sulfation Added |
| CHA27 − N1/2 + NS4 + 6S1 | Chsy1 Hsndst1 Hsndst2 | Hsndst4 Hs6st1 | CS deficient<br>HS NDST1-sulfation deficient<br>HS NDST2-sulfation deficient<br>HS NDST4-sulfation Added<br>HS 6OST1-sulfation Added |
| CHA27 − N1/2 + NS4 + 6S2 | Chsy1 Hsndst1 Hsndst2 | Hsndst4 Hs6st2 | CS deficient<br>HS NDST1-sulfation deficient<br>HS NDST2-sulfation deficient<br>HS NDST4-sulfation Added<br>HS 6OST2-sulfation Added |
| CHA27 − N1/2 + NS4 + 6S3 | Chsy1 Hsndst1 Hsndst2 | Hsndst4 Hs6st3 | CS deficient<br>HS NDST1-sulfation deficient<br>HS NDST2-sulfation deficient<br>HS NDST4-sulfation Added<br>HS 6OST3-sulfation Added |
| CHA27 − N1/2 + NS3 + 3S1 | Chsy1 Hsndst1 Hsndst2 | Hsndst3 Hs3st1 | CS deficient<br>HS NDST1-sulfation deficient<br>HS NDST2-sulfation deficient<br>HS NDST3-sulfation Added<br>HS 3OST1-sulfation Added |
| CHA27 − N1/2 + NS3 + 3S2 | Chsy1 Hsndst1 Hsndst2 | Hsndst3 Hs3st2 | CS deficient<br>HS NDST1-sulfation deficient<br>HS NDST2-sulfation deficient<br>HS NDST3-sulfation Added<br>HS 3OST2-sulfation Added |
| CHA27 − N1/2 + NS3 + 3S3a or b | Chsy1 Hsndst1 Hsndst2 | Hsndst3 3a or 3b | CS deficient<br>HS NDST1-sulfation deficient<br>HS NDST2-sulfation deficient<br>HS NDST3-sulfation Added<br>HS 3OST3-sulfation Added |
| CHA27 − N1/2 + NS3 + 3S4 | Chsy1 Hsndst1 Hsndst2 | Hsndst3 Hs3st4 | CS deficient<br>HS NDST1-sulfation deficient<br>HS NDST2-sulfation deficient<br>HS NDST3-sulfation Added<br>HS 3OST4-sulfation Added |
| CHA27 − N1/2 + NS3 + 3S5 | Chsy1 Hsndst1 Hsndst2 | Hsndst3 Hs3st5 | CS deficient<br>HS NDST1-sulfation deficient<br>HS NDST2-sulfation deficient<br>HS NDST3-sulfation Added<br>HS 3OST5-sulfation Added |
| CHA27 − N1/2 + NS3 + 3S6 | Chsy1 Hsndst1 Hsndst2 | Hsndst3 Hs3st6 | CS deficient<br>HS NDST1-sulfation deficient<br>HS NDST2-sulfation deficient<br>HS NDST3-sulfation Added<br>HS 3OST6-sulfation Added |
| CHA27 − N1/2 + NS4 + 3S1 | Chsy1 Hsndst1 Hsndst2 | Hsndst4 Hs3st1 | CS deficient<br>HS NDST1-sulfation deficient<br>HS NDST2-sulfation deficient<br>HS NDST4-sulfation Added<br>HS 3OST1-sulfation Added |
| CHA27 − N1/2 + NS4 + 3S2 | Chsy1 Hsndst1 Hsndst2 | Hsndst4 Hs3st2 | CS deficient<br>HS NDST1-sulfation deficient<br>HS NDST2-sulfation deficient<br>HS NDST4-sulfation Added<br>HS 3OST2-sulfation Added |
| CHA27 − N1/2 + NS4 + 3S3a or 3b | Chsy1 Hsndst1 Hsndst2 | Hsndst4 Hs3st3a or 3b | CS deficient<br>HS NDST1-sulfation deficient<br>HS NDST2-sulfation deficient<br>HS NDST4-sulfation Added<br>HS 3OST3-sulfation Added |
| CHA27 − N1/2 + NS4 + 3S4 | Chsy1 Hsndst1 Hsndst2 | Hsndst4 Hs3st4 | CS deficient<br>HS NDST1-sulfation deficient<br>HS NDST2-sulfation deficient<br>HS NDST4-sulfation Added<br>HS 3OST4-sulfation Added |
| CHA27 − N1/2 + NS4 + 3S5 | Chsy1 Hsndst1 Hsndst2 | Hsndst4 Hs3st5 | CS deficient<br>HS NDST1-sulfation deficient<br>HS NDST2-sulfation deficient<br>HS NDST4-sulfation Added<br>HS 3OST5-sulfation Added |
| CHA27 − N1/2 + NS4 + 3S6 | Chsy1 Hsndst1 Hsndst2 | Hsndst4 Hs3st6 | CS deficient<br>HS NDST1-sulfation deficient<br>HS NDST2-sulfation deficient<br>HS NDST4-sulfation Added<br>HS 3OST6-sulfation Added |

TABLE 1-continued

Cell lines producing modified heparan sulfate

| Cell Line ID | Gene KO | Gene KI | Enzymes |
|---|---|---|---|
| CHA27 – N1/2 + NS3 + 6ST1/2 + 3S1 | Chsy1 Hsndst1 Hsndst2 | Hsndst3 Hs6st1/2 Hs3st1 | CS deficient<br>HS NDST1-sulfation deficient<br>HS NDST2-sulfation deficient<br>HS NDST3-sulfation Added<br>HS 6OST1/2-sulfation Added<br>HS 3OST1-sulfation Added |
| CHA27 – N1/2 + NS3 + 6ST1/2 + 3S2 | Chsy1 Hsndst1 Hsndst2 | Hsndst3 Hs6st1/2 Hs3st2 | CS deficient<br>HS NDST1-sulfation deficient<br>HS NDST2-sulfation deficient<br>HS NDST3-sulfation Added<br>HS 6OST1/2-sulfation Added<br>HS 3OST2-sulfation Added |
| CHA27 – N1/2 + NS3 + 6ST1/2 + 3S3a or 3b | Chsy1 Hsndst1 Hsndst2 | Hsndst3 Hs6st1/2 Hs3st3a or 3b | CS deficient<br>HS NDST1-sulfation deficient<br>HS NDST2-sulfation deficient<br>HS NDST3-sulfation Added<br>HS 6OST1/2-sulfation Added<br>HS 3OST3-sulfation Added |
| CHA27 – N1/2 + NS3 + 6ST1/2 + 3S4 | Chsy1 Hsndst1 Hsndst2 | Hsndst3 Hs6st1/2 Hs3stT4 | CS deficient<br>HS NDST1-sulfation deficient<br>HS NDST2-sulfation deficient<br>HS NDST3-sulfation Added<br>HS 6OST1/2-sulfation Added<br>HS 3OST4-sulfation Added |
| CHA27 – N1/2 + NS3 + 6ST1/2 + 3S5 | Chsy1 Hsndst1 Hsndst2 | Hsndst3 Hs6st1/2 Hs3st5 | CS deficient<br>HS NDST1-sulfation deficient<br>HS NDST2-sulfation deficient<br>HS NDST3-sulfation Added<br>HS 6OST1/2-sulfation Added<br>HS 3OST5-sulfation Added |
| CHA27 – N1/2 + NS3 + 6ST1/2 + 3S6 | Chsy1 Hsndst1 Hsndst2 | Hsndst3 Hs6st1/2 Hs3st6 | CS deficient<br>HS NDST1-sulfation deficient<br>HS NDST2-sulfation deficient<br>HS NDST3-sulfation Added<br>HS 6OST1/2-sulfation Added<br>HS 3OST6-sulfation Added |
| CHA27 – N1/2 + NS4 + 6ST1/2 + 3S1 | Chsy1 Hsndst1 Hsndst2 | Hsndst4 Hs6stT1/2 Hs3st1 | CS deficient<br>HS NDST1-sulfation deficient<br>HS NDST2-sulfation deficient<br>HS NDST4-sulfation Added<br>HS 6OST1/2-sulfation Added<br>HS 3OST1-sulfation Added |
| CHA27 – N1/2 + NS4 + 6ST1/2 + 3S2 | Chsy1 Hsndst1 Hsndst2 | Hsndst4 Hs6st1/2 Hs3st2 | CS deficient<br>HS NDST1-sulfation deficient<br>HS NDST2-sulfation deficient<br>HS NDST4-sulfation Added<br>HS 6OST1/2-sulfation Added<br>HS 3OST2-sulfation Added |
| CHA27 – N1/2 + NS4 + 6ST1/2 + 3S3a or 3b | Chsy1 Hsndst1 Hsndst2 | Hsndst4 Hs6st1/2 Hs3st3a or 3b | CS deficient<br>HS NDST1-sulfation deficient<br>HS NDST2-sulfation deficient<br>HS NDST4-sulfation Added<br>HS 6OST1/2-sulfation Added<br>HS 3OST3-sulfation Added |
| CHA27 – N1/2 + NS4 + 6ST1/2 + 3S4 | Chsy1 Hsndst1 Hsndst2 | Hsndst4 Hs6st1/2 HSs3st4 | CS deficient<br>HS NDST1-sulfation deficient<br>HS NDST2-sulfation deficient<br>HS NDST4-sulfation Added<br>HS 6OST1/2-sulfation Added<br>HS 3OST4-sulfation Added |
| CHA27 – N1/2 + NS4 + 6ST1/2 + 3S5 | Chsy1 Hsndst1 Hsndst2 | Hsndst4 Hs6st1/2 Hs3st5 | CS deficient<br>HS NDST1-sulfation deficient<br>HS NDST2-sulfation deficient<br>HS NDST4-sulfation Added<br>HS 6OST1/2-sulfation Added<br>HS 3OST5-sulfation Added |
| CHA27 – N1/2 + NS4 + 6ST1/2 + 3S6 | Chsy1 Hsndst1 Hsndst2 | Hsndst4 Hs6st1/2 Hs3st6 | CS deficient<br>HS NDST1-sulfation deficient<br>HS NDST2-sulfation deficient<br>HS NDST4-sulfation Added<br>HS 6OST1/2-sulfation Added<br>HS 3OST6-sulfation Added |

TABLE 2

Enzymes for Genetically Modified Cells Lines Producing Modified HS

| Gene(s) | Enzyme |
|---|---|
| GUSB | Beta-glucuronidase |
| GALNS | Galactosamine-6 sulfatase |
| IDUA | Alpha-L-iduronidase |
| SGSH | Sulfamidase |
| HGSNAT4 | Glucosamine N-acetyltransferase |
| IDS | Uronate-2-sulfatase |
| NAGLU | Alpha-N-acetylglucosaminidase |
| PAPSS1, PAPSS2 | PAPS synthase |
| FAM20B | Xylose kinase |
| XYLT1 | Xylosyltransferase 1 |
| XYLT2 | Xylosyltransferase 2 |
| B4galt7 | Galactosyltransferase 1 |
| B3galt6 | Galactosyltransferase 2 |
| B3gat3 | Glucuronyltransferase 1 |
| EXTL3 | Exostosin-Like Glycosyltransferase 3 |
| EXT1 | Exostosin Glycosyltransferase 1 |
| EXT2 | Exostosin Glycosyltransferase 2 |
| HPSE | Heparanase |
| GPC1 | Glypican 1 |
| GPC2 | Glypican 2 |
| GPC3 | Glypican 3 |
| GPC4 | Glypican 4 |
| GPC5 | Glypican 5 |
| GPC6 | Glypican 6 |
| SDC1 | Syndecan 1 |
| SDC2 | Syndecan 2 |
| SDC3 | Syndecan 3 |
| SDC4 | Syndecan 4 |
| BGCAN/TGFBR3 | Betaglycan |
| CD47 | CD47 |
| CD44V3 | CD44V3 |
| NRP1 | Neuropillin 1 |
| SRGN | Serglycin |
| PLC | Perlecan |
| AGRN | Agrin |
| COL18A1 | Collagen 18 |
| NDST1 | N-deacetylase and N-sulfotransferase 1 |
| NDST2 | N-deacetylase and N-sulfotransferase 2 |
| NDST3 | N-deacetylase and N-sulfotransferase 3 |
| NDST4 | N-deacetylase and N-sulfotransferase 4 |

TABLE 2-continued

Enzymes for Genetically Modified
Cells Lines Producing Modified HS

| Gene(s) | Enzyme |
| --- | --- |
| Glce | Glucuronyl C5-epimerase |
| Hs2st | Heparan sulfate uronyl 2-O-sulfotransferase |
| Hs3st1 | Heparan sulfate glucosaminyl 3-O-sulfotransferase |
| Hs3st2 | Heparan sulfate-glucosamine 3-sulfotransferase 2 |
| Hs3st3a1 | Heparan sulfate-glucosamine 3-sulfotransferase 3A1 |
| Hs3st3b1 | Heparan sulfate-glucosamine 3-sulfotransferase 3B1 |
| Hs3st4 | Heparan sulfate-glucosamine 3-sulfotransferase 4 |
| Hs3st5 | Heparan sulfate-glucosamine 3-sulfotransferase 5 |
| Hs3st6 | Heparan sulfate-glucosamine 3-sulfotransferase 6 |
| Hs6st1 | Heparan sulfate 6-O-sulfotransferase 1 |
| Hs6st2 | Heparan sulfate 6-O-sulfotransferase 2 |
| Hs6st3 | Heparan sulfate 6-O-sulfotransferase 3 |
| Hpse | Heparanase (Hpse) |
| Sulf1 | Sulfatase-1 |
| Sulf2 | Sulfatase-2 |

TABLE 3

Cell surface ligand binding to cell lines producing modified HS

Ligands

Fibroblast Growth Factors
Bone morphogenetic proteins (BMP)
Macrophage inflammatory protein 1 Alpha, (MIP1alpha, CCL3)
Stromal derived factor 1, (SDF-1, CXCL12)
Platelet Factor 4, (CXCL4)
Interleukin 8, (IL-8)
Interferon beta (IFN-beta)
Interferon gamma (IFN-gamma)
Hepatocyte growth factor (HGF)
Vascular endothelia growth factor (VEGF)
Antithrombin/thrombin
Neuropillin-1
Amyloid precursor-like protein 1 (APLP-1)
Endostatin and Angiostatin
Heparin-binding EGF-like growth factor(HB-EGF)
Platelet-derived growth factor (PDGF)
WNT
Hedgehogs (HH)

TABLE 4

Enzymes for Genetically Modified Cells
Lines Producing Modified CS/DS

| Gene(s) | Enzyme |
| --- | --- |
| CsGalNAcT1 | GalNAc transferase 1 |
| CSGalNAcT2 | GalNAc transferase 2 |
| Chsy1 | Chondroitin sulfate synthase 1 (GlcAT and GalNAcT activities) |
| Chsy3 | Chondroitin sulfate synthase 3 |
| Chpf | Chondroitin sulfate polymerizing factor |
| Chpf2 | Chondroitin sulfate polymerizing factor |
| Chst11 | Chondroitn 4-O-sulfotransferase 1 |
| Chst12 | Chondroitin 4-O-sulfotransferase 2 |
| Chst13 | Chondroitin 4-O-sulfotransferase 3 |
| Chst15 | Chondroitin 4-sulfate 6-O-sulfotransferase |
| Chst3 | Chondroitin 6 sulfotransferase-1 |
| Chst7 | Chondroitin 6-O-sulfotransferase 2 |
| Dse | Dermatan sulfate glucuronyl C5 epimerase 1 |
| Dsel | Dermatan sulfate glucuronyl C5 epimerase-like |

TABLE 4-continued

Enzymes for Genetically Modified Cells
Lines Producing Modified CS/DS

| Gene(s) | Enzyme |
| --- | --- |
| Chst14 | Dermatan sulfate 4-O-sulfotransferase |
| Agc1 | Aggrecan (CSPG1) |
| Vcan | Versican/PG-M (CSPG2) |
| Ncan | Neurocan (CSPG3) |
| Bcan | Brevican (BCAN) |
| Epyc | Epiphycan (Dspg3) |
| Col9a2 | Procollagen, type IX, alpha 2 |
| Ptprz1 | DSD-1-proteoglycan, Phosphacan |
| Thbd | Thrombomodulin |
| Esm1 | Endocan |
| Lepre1 | Leprecan (Prolyl 3-hydroxylase 1) |
| Dcn | Decorin |
| Bgn | Biglycan |
| Spock1 | Testican 1 (Spock1; osteonectin1) |
| Spock2 | Testican 2 (Spock2, osteonectin2 |
| Spock3 | Testican 2 (Spock3; osteonectn3) |
| Prg4 | Proteoglycan-4 (Lubricin) |
| Cspg4 | NG2 (CSPG4) |
| Cd74 | Invariant chain |
| Cd44 | CD44 |

TABLE 5

Enzymes for Genetically Modified Cell
Lines for Glycosaminoglycan Synthesis

| Gene | Proteoglycan |
| --- | --- |
| Bpnt1 | BPNT1 (3'-nucleotidase) |
| Entpd4 | ENTPD4 (ectonucleoside triphosphate diphosphohydrolase 4) |
| Impad1 | GPAPP (Golgi PAP phosphatase) |
| Papss1 | PAPS synthetase-1 (ATP sulfurylase/APS kinase 1)) |
| Papss2 | PAPS synthetase-2 (ATP sulfurylase/APS kinase 2) |
| Slc35b2 | PAPS transporter (PAPST-1) |
| Slc35b3 | PAPS transporter-2 (PAPST-2) |
| Slc26a1 | Sulfate transporter |
| Slc26a2 | Sulfate transporter (DTDST) |
| Ugdh | UDP-Glc Dehydrogenase |
| Uxs1 | UDP-Glc decarboxylase |
| Gale | UDP-Glc/UDP-Gal 4' epimerase |
| Slc35b4 | UDP-Xylose/GlcNAc transporter |
| Slc35a2 | UDP-Gal transporter) |
| Slc35b1 | UDP-Gal transporter-2 |
| Slc35d1 | UDP-GlcA/GalNAc transporter |
| Slc35d2 | UDP-Glc/UDP-GlcNAc transporter) |
| Slc35a3 | UDP-GlcNAc transporter |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition comprising a heparan sulfate having reduced FGF2 binding compared to a heparan sulfate derived from a wild-type Chinese Hamster Ovary (CHO) cell, wherein the heparan sulfate is derived from a cell line comprising: (i) a genetic modification selected from the group consisting of deficiency in Heparan sulfate 2-O-sulfotransferase (HS2ST), deficiency in heparan sulfate N-deacetylase/sulfotransferase-1 (HSNDST1) and heparan sulfate N-deacetylase/sulfotransferase-2 (HSNDST2), and transgenic for Sulfatase 2 (Sulf2), and (ii) a genetic modification selected from the group consisting of deficiency in chondroitin sulfate synthase 1 (ChSy), Chondroitin Sulfate N-Acetylgalactosaminyltransferase 2 (CSGalNAcT2), and Chondroitin Polymerizing Factor (ChPF), and wherein the composition is at least 95% free from chondroitin sulfate.

2. The composition of claim 1, wherein the cell line is further genetically modified to be deficient for one or more of chondroitin sulfate synthase 1 (ChSy), Chondroitin Sulfate N-Acetylgalactosaminyltransferase 2 (CSGalNAcT2), Chondroitin Polymerizing Factor (ChPF), heparan sulfate 2-O-sulfotransferase (HS2ST), glucuronic acid epimerase (GLCE), heparan sulfate N-deacetylase/sulfotransferase-1 (HSNDST1), heparan sulfate N-deacetylase/sulfotransferase-2 (HSNDST2), Sulfatase 1 (Sulf1), Beta-glucuronidase (GUSB), Galactosamine-6 sulfatase (GALNS), Alpha-L-iduronidase (IDUA), Sulfamidase (SGSH), N-acetyltransferase (AANAT, ARD1A, GNPNAT1, HGSNAT, MAK10, NAT1, NAT2, NAT5, NAT6, NAT8, NAT8L, NAT9, NAT 10, NAT 11, NAT12, NAT13, NAT14, NAT14), Uronate-2-sulfatase (IDS), Alpha-N-acetylglucosaminidase (NAGLU), PAPS synthase (PAPSS1, PAPSS2), Xylosyltransferase 1 (XYLT1), Xylosyltransferase 2 (XYLT2), Galactosyltransferase 1 (B4GALT1), Galactosyltransferase 2 (B4GALT2), Glucuronyltransferase 1 (UDPGT), Exostosin-Like Glycosyltransferase 3 (EXTL3), Exostosin Glycosyltransferase 1 (EXT1), Exostosin Glycosyltransferase 2 (EXT2), Heparanase (HPSE), Glypican 1 (GPC1), Glypican 2 (GPC2), Glypican 3 (GPC3), Glypican 4 (GPC4), Glypican 5 (GPC5), Glypican 6 (GPC6), Syndecan 1 (SDC1), Syndecan 2 (SDC2), Syndecan 3 (SDC3), Syndecan 4 (SDC4), Betaglycan (BGCAN/TGFBR3), CD44V3 (CD44V3), Neuropillin 1 (NRP1), Serglycin (SRGN), Perlecan (PLC), Agrin (AGRN), or Collagen 18 (COL18A1).

3. The composition of claim 1, wherein the composition is derived from a cell line genetically modified to be deficient for chondroitin sulfate synthase 1 (ChSy).

4. The composition of claim 1, wherein the composition is derived from cells that do not produce chondroitin sulfate.

5. The composition of claim 1, wherein the cell line is further genetically modified to be transgenic for one or more of heparan sulfate N-deacetylase/sulfotransferase-3 (HSNDST3), heparan sulfate N-deacetylase/sulfotransferase-4 (HSNDST4), heparan sulfate 6-O-sulfotransferase 1 (HS6ST1), heparan sulfate 6-O-sulfotransferase 2 (HS6ST2), heparan sulfate 6-O-sulfotransferase 3 (HS6ST3), heparan sulfate 6-O-sulfotransferase (HS6ST4), heparan sulfate (glucosamine) 3-O-sulfotransferase 1 a (HS3ST1A), heparan sulfate (glucosamine) 3-O-sulfotransferase 1 b (HS3ST1B), heparan sulfate (glucosamine) 3-O-sulfotransferase 1 2 (HS3ST2), heparan sulfate (glucosamine) 3-O-sulfotransferase 3a or 3b (HS3ST3a or 3b), heparan sulfate (glucosamine) 3-O-sulfotransferase 3 (HS3ST4), heparan sulfate (glucosamine) 3-O-sulfotransferase 5 (HS3ST5), heparan sulfate (glucosamine) 3-O-sulfotransferase 6 (HS3ST6), Beta-glucuronidase (GUSB), Galactosamine-6 sulfatase (GALNS), Alpha-L-iduronidase (IDUA), Sulfamidase (SGSH), N-acetyltransferase (HGSNAT), Uronate-2-sulfatase (IDS), Alpha-N-acetylglucosaminidase (NAGLU), PAPS synthase (PAPSS1, PAPSS2), Xylosyltransferase 1 (XYLT1), Xylosyltransferase 2 (XYLT2), Galactosyltransferase 1 (B4GALT1), Galactosyltransferase 2 (B4GALT2), Glucuronyltransferase 1 (UDPGT), Exostosin-Like Glycosyltransferase 3 (EXTL3), Exostosin Glycosyltransferase 1 (EXT1), Exostosin Glycosyltransferase 2 (EXT2), Heparanase (HPSE), Glypican 1 (GPC1), Glypican 2 (GPC2), Glypican 3 (GPC3), Glypican 4 (GPC4), Glypican 5 (GPCS), Glypican 6 (GPC6), Syndecan 1 (SDC1), Syndecan 2 (SDC2), Syndecan 3 (SDC3), Syndecan 4 (SDC4), Betaglycan (BGCAN/TGFBR3), CD44V3 (CD44V3), Neuropillin 1 (NRP1), Serglycin (SRGN), Perlecan (PLC), Agrin (AGRN), or Collagen 18 (COL18A1).

6. The composition of claim 1, wherein the composition comprises a heparan sulfate with decreased heparan sulfate polymerization, decreased heparan sulfate sulfation, decreased epimerization of uronic acid in heparan sulfate, decreased N-sulfation of heparan sulfate, and/or deccreased O-sulfation of heparan sulfate compared to a heparan sulfate from a wild-type CHO cell.

7. The composition of claim 1, wherein the heparan sulfate is at least 95% free of protein and nucleic acid contamination.

8. A method of treating a thrombosis, an inflammation, a cancer, a microbial infection, a neurodegenerative disorder, or a wound in an individual in need thereof comprising administering an effective amount of the composition claim 1.

9. A composition comprising a heparan sulfate having increased FGF2 cell surface binding or FGF2 signaling compared to a heparan sulfate derived from a wild-type Chinese Hamster Ovary (CHO) cell, wherein the heparan sulfate is derived from a cell line comprising a genetic modification to (i) overexpress a gene selected from the group consisting of heparan sulfate N-deacetylase/sulfotransferase-1 (HSNDST1), heparan sulfate N-deacetylase/sulfotransferase-2 (HSNDST2), heparan sulfate 6-O-sulfotransferase 1 (HS6ST1), and heparan sulfate 6-O-sulfotransferase 2 (HS6ST2), and (ii) be deficient in a gene selected from the group consisting of chondroitin sulfate synthase 1 (ChSy), Chondroitin Sulfate N-Acetylgalactosaminyltransferase 2 (CSGalNAcT2), and Chondroitin Polymerizing Factor (ChPF), and wherein the composition is at least 95% free from chondroitin sulfate.

10. The composition of claim 9, wherein the heparan sulfate has increased heparan sulfate polymerization, increased heparan sulfate sulfation, increased epimerization of uronic acid in heparan sulfate, increased N-sulfation of heparan sulfate, and/or increased O-sulfation of heparan sulfate compared to a heparan sulfate from a wild-type CHO cell.

* * * * *